United States Patent [19]

Weiner et al.

[11] Patent Number: 5,670,152

[45] Date of Patent: Sep. 23, 1997

[54] IMMUNOREACTIVE POLYPEPTIDE COMPOSITIONS

[75] Inventors: Amy J. Weiner, Benicia; Michael Houghton, Danville, both of Calif.

[73] Assignee: Chiron Corporation, Emeryville, Calif.

[21] Appl. No.: 440,103

[22] Filed: May 12, 1995

Related U.S. Application Data

[62] Division of Ser. No. 231,368, Apr. 19, 1994, which is a continuation of Ser. No. 759,575, Sep. 13, 1991.

[51] Int. Cl.$^6$ .............................. A61K 39/29; C12Q 1/70; C07K 14/18
[52] U.S. Cl. ................................. 424/189.1; 424/228.1; 530/350; 435/5
[58] Field of Search .......................... 435/5; 530/350; 424/189.1, 228.1

[56] References Cited

U.S. PATENT DOCUMENTS

| 5,350,671 | 9/1994 | Houghton et al. ........................ 435/5 |
| 5,372,928 | 12/1994 | Miyamura et al. ........................ 435/5 |

FOREIGN PATENT DOCUMENTS

| 318216 | 5/1989 | European Pat. Off. . |
| 0388232 | 9/1990 | European Pat. Off. . |
| 0 149 182 A1 | 3/1992 | European Pat. Off. . |
| 8904669 | 6/1989 | WIPO . |
| 9011089 | 10/1990 | WIPO . |
| 9014436 | 11/1990 | WIPO . |

OTHER PUBLICATIONS

Takeuchi et al., "The Putative Nucleocapsid and Envelope Protein . . .," J. Gen Virol. 71:3027–3033 (1990).
Farci et al., "Lack of Protective Immunity . . .," Science 258:135–140 (1992).
Hijikata et al., "Hypervariable Regions . . .," Biochem. Biophys. Res Comm 175:220–228 (1991).
Kubo et al., 1989, *Japan Nucl. Acids Res* 17(24):10367–10372.
Choo et al. 1990, *Brit. Med. Bull.* 46:423–442.
Kato et al., 1990, *Proc. Natl. Acad. Sci. USA* 87:9524–9528.
Takeuchi et al., 1990, *Gene* 91:287–291.
Takeuchi et al., 1990, *J. Gen. Virol.* 71:3027–3033.
Takeuchi et al., 1990, *Nucl. Acids Res.* 18(5):4626.
Choo et al., 1991, *Proc. Natl. Acad. Sci. USA* 88:2451–2455.
Han et al., 1991, *Proc. Natl. Acad. Sci. USA* 88:2451–2455.
Okamoto et al., 1991, *Japan J. Exp. Med.* 60(3):167–177.
Takamizawa et al., 1991, *J. Virol.* 65:1105–1113.
Weiner et al., 1991, *Virol.* 180:842–848.
Houghton et al., 1991, *Hepatology* 14(2):381–388.
Goodenow, M., et al., "HIV-1 isolates are rapidly evolving quasispecies: Evidence for viral mixtures and preferred nucleotide substitutions" *Journal of Acquired Immune Deficiency Syndromes* (1989) 2(4):344–352.
Weiner et al., "Evidence for immune selection of hepatitis C virus (HCV) putative envelope glycoprotein variants: potential role in chronic HCV infections" *Proc. Natl. Acad. Sci. USA* (1992) 89:3468–3472.
Okamoto et al., "Nucleotide sequence of the genomic RNA of hepatitis C virus isolated from a human carrier: comparison with reported isolates for conserved and divergent regions" *Journal of General Virology* (1991) 72(11):2697–2704.
Kremsdorf et al., "Partial nucleotide sequence analysis of a French hepatitis C virus: implications for HCV genetic variability in the E2/NS1 protein" *Journal of General Virology* (1991) 72:2557–2561.

*Primary Examiner*—Michael P. Woodward
*Attorney, Agent, or Firm*—Alisa A. Harbin; Susan A. Wolffe; Robert P. Blackburn

[57] ABSTRACT

This invention relates generally to immunoreactive polypeptide compositions comprising hepatitis type C viral epitopes, methods of using the compositions in immunological applications, and materials and methods for making the compositions

9 Claims, 32 Drawing Sheets

192

```
          VREGNASRCWVAMTPTVATRDGKLPATQLRRHIDLLVGSATLCSALYVGDLCGSVFLVGQ    YQVRNSTGLYHVTNDCPNSSIVYEAADAILHTPGCVPC
HCV-1     ------------------------------------------------------------    -------------------------------------
HCT18     -H---V-------V-------------T------------------------I-------    H------------------------------A-----
Th        ---------------------------A---R---T------------------I-----    ---------------S-I-----------------A-
HCT23     ---D-V-------V-------------A-------T------------------------    ---------------S-I-------------T-T-S-
HCT27     ---K--PVA----------------N---------T------------------------    ---------------S-I-------------T-T-S-
HC-J1     ---V--------------------------------------------------------    -----------------H-------------------
          ----*-----------------------*-------*----------*-----------*    ------*------------*-----------*----*
HC-J4     ---D-S-----------L-A-NASV-T-TI---V------A-AF-----M----------    -----------E---VS-I----------S---M-M-
HCV-J     ---S-F-----------L-A-NSSI-T-TI---V------A--A-----M----------    -----------E---VS-I----------S---M-M-
HCV J1    ---N-S-----------L-A-NASV-T-T----V------T-AF-----M----------    -----------E---VS-I----------S---M-M-
BK        ---S-------------L-A-NVTI-T-TI---V------A-AF-----M----------    -----------E-H-VS-I----------S-A-V-M-A
                                                                                                           -L-M-
```

230

```
          LFTFSPRRHWTTQGCNCSIYPGHITGHRMAWDMMMNWSPTTALVMAQLLRIPQAILDMIA
HCV-1     ------------------------------------------------------------
HCT18     ------------------------------------------------------------
Th        ------------------------------------------------------------
HCT23     ---D--------------------------------------------------------
HCT27     ---D--------------------------------------------------------
HC-J1     ----------------------------------------------I-------------
          -**------------------------------------*-----*-------------*
HC-J4     --E-V-D----------LS--------------A--V-----VS----------M---S
HCV-J     --YE-V-D---------VS----------A----A------------------------VV--V-
HCV J1    --E-V-D----------VS--------------A--V-----VS---------------VV--V-
BK        --V-L-D----------VS----------A------------VM----------------VM--V-
                                                                        VV--V-
```

```
         GAHWGVLAGIAYFSMVGNWAKVLVVLLLFAGVDA
HCV-1    350
HCT18    ---------------------------------
Th       ---------------------------------
HCT23    ----------------M----------------
HCT27    ---------------------------------
HC-J1    ---------------------------------
                        *      *         *
HC-J4    ----------L--Y----------I-A----G
HCV-J    ----------L--Y----------I-M----G
HCV J1   ----------L--Y----------I-M----G
BK       ----------L--A----------I-M----G
```

FIG. 2B

Comparative Amino Acid Sequence of the Putative E2/NS1 Region of HCV Isolates

```
HCV-1    370    KVLVVLLLFAGVDAETHVTGGSAGHTVSGFVSLLAPGAKQNVQLINTNGSWHLNSTALNC
HCT27           --------------T-YT---N-AR-TQALT-FFS-----DI----------I-R-----
HCVE1           ---L------------YT----TAR-TQ-L---FSR----DI----------I-R-----
H77             ------------------------R-TA-L-G--T------I----------I-------
H90             ------------------------RS-L-IA-F-TR-P---I---K------I-------
Th              ----------------T------A-GAL-IA--FNQ--R--I----------I-------
HC-J1           ----------------I-S--Q-ARAM--L---FT------I----------I-------
HC-J4           ---I-A-------G--YTS--A-S--T-TLA--FS---S-RI--V-------I-R-----
HCV-J           ---I-M-------GH------RVASSTQSL--W-SQ-PS-KI--V-------I-R-----
JH-1            ---I-M-------GH-R----VQ--VT-TLT--FR---S-KI--V-------I-R-----
BK              ---I-M-------GD------AQAK-TNRL--MF-S-PS-KI----------I-R-----

HCV-1    430    NDSLNTGWLAGLFYHHKFNSSGCPERLASCRPLTDFDQGWGPISYANGSGPDQRPYCWHY
HCT27           -G--D---V-----Y-----------M------A--Q--------------EH-------
HCVE1           -E--D---V-----Y-----------M------A--------------T--EH-------
H77             -E-----------------------------R----A-------------L-E-------
H90             -----A--I-------G--------------R--------------------E-------
Th       ****   ----h---I-----Y---------------------------------------------
HC-J1           -E----------I-Q----------------R------------H---------------
HC-J4           ----H--F--A---T-R---------M-----IDW-A------T-TEPDS----------
HCV-J           ----Q--FI-A---A-R--A------M-----IDE-A------THDMPESS---------
JH-1            ----Q--F--A---T----A------M----SIDK--------T--QPDNS---------
BK              ----Q--F--A---T-S---------M-Q--TIDK--------T--ES-RS---------

HCV-1    490    PPKPCGIVPAKSVCGPVYCFTPSPVVVGTTDRSGAPTYSWGENDTDVFVLNNTRPPLGNW
HCT27           ----------QN------------------NKL-----N--S-E----------------
HCVE1           ----------QT------------------NKL-----N--C------------------
H77             --R---------------------------------------A-----------------
H90             --R-----------------------------------N--------LI-----------
Th              --------------------------------------N--A------------------
HC-J1           ------------------------
HC-J4           A-R-------SQ------------
HCV-J           A-R-------SQ--------------------F----------E---LL-S-----Q---
JH-1            A-RQ------SQ--------------------F-----N--D-E---LL-------H---
BK              --PQ-T----SE--------------------F-V---R----E---LL-------Q---
```

FIG. 3A

```
550
HCV-1   FGCTWMNSTGFTKVCGAPPCVIGGAGNNTLHCPTDCFRKHPDATYSRCGSGPWITPRCLV
HCT27   ----S-------------------------------Q-----------------AA---
HCVE1   ---V-S-----------------------------Y----E------------------
H77    ------------------------V----------L----E------------------
H90    ------------------------V----------R----E------M-----------
Th     ------------------------V---------------------------M------
HC-J1   --------------------T--G---N--V----V-------E---TK----L---M-
HC-J4   --------------------T--G---N--V----T-------E---TK----L---M-
HCV-J   --------------------T--G---N--V----T-------E---TK----L---M-
JH-1    -----------------------------------------------------------
BK     -----------------------------------------------------------

610
HCV-1   DYPYRLWHYPCTINYTIFKIRMYVGGVEHRLEAACNWTRGERCDLEDRDRSELSPLLLTT
HCT27   H-------------V--VQ--------D--V-----------D----RL-S--------
HCVE1   G-------------V--L-V-------------QV-----------N-D---S------
H77    ------------------V--------------------------------S-------
H90    H-----------------V--------I-------------------------S-----
Th     N-----------------V----------------------------------S-----
HC-J1   --------------V-F-V--V--------------------------------S----
HC-J4   --------------V-F---V--------------------------------S-----
HCV-J   --------------V-F---V--------------------------------S-----
JH-1    ---------------------------------N-------------P-----------
BK     ---------------------------------N-----------------------S-
```

FIG. 3B

```
670   TQWQVLPCSFTTLPALSTGLIHIHQNIVDVQYLYGVGSSIASWAIKWEYVVLLFLLLADA
HCV-1
HCT27             -T-------------------------V-----------I-------N-
HCVE1             -T-----------------------------V-------I---------
H77                                                      -V-
H90                                                      -V-
Th                                     -T-
HC-J1
HC-J4
HCV-J    -E--I----------------R-----------I--AVV--F---------IL-------
HCV-J
JH-1     -E------------------------------I--AVV--F------L-----------
BK

730   RVCSCLWMMLLISQAEAALENLVILNAASLAGTHGLVSFLVFFCFAWYLKGKWVPGAVYT
HCV-1
HCT27    -I----------------------------L------A-AVA-----------R-----A-A
HCVE1
H77
H90                                          -A-
Th
HC-J1    ---A------------A-------T-----V-----V--A----L------A---I--RL----A-A
HC-J4
HCV-J    ---A------------A----------------V-S-V--A--IL------A---I--RL----T-A
HCV-J
JH-1
BK

790   FYGMWPLLLLLLLALPQRAYALDTEVAASCGGVVLVGLMALTLSPYYKRYISWCLWWLQYF
HCV-1
HCT27                    ----M
Th
HC-J1
HC-J4
HCV-J
HCV-J    L--V--------P-----M-R-M-----A-F----VL-------VFLARLI------
JH-1     L--V--------P-----M-R-M-----A-F----VL-------VFLARLI------
BK
```

```
              M
              ┌─┐
HCV J1.1  384 HTRVIGGVQGHVTSTLTSLFRPGASQKIQLVNTNGSWHINRTALNCNDSLQTGFLAALFY
HCV J1.2      N-H-----GAFG----Q-------------------------------K---------
                   R  A

HCV J1.1  444 THKFNASGCPERMASCRSIDKFDQGWPITYAQPDNSDQRPYCWHYAPRQCGIVPASQVC
HCV J1.2      ---R--------------------------------------T---------------
                        VG                R*

HCV J1.1  504 GPVYCFTPSPVVVGTTDRSGAPTYNWGDNETDVLLLNNTRPPHGNWFGCTWMNSTGFTKT
HCV J1.2      ------------------------------------------------------------
                        F V

HCV J1.1  564 CGGPPCNIGGVGNNTLTCPTDCFRKHPDATYTKCGSGPWLTPRCLVDYPYRLWHYPCTVN
HCV J1.2      ------------------------------------------------------------
                      A  I           E                   R

HCV J1.1  624 FTIFKVRMYGGVEHRLDAACNWTRGER  651
HCV J1.2      ---------------------------
                   K    E
```

FIG. 8A

```
              E2 HV
          ┌─────────┐
HCT27  384 TTYTTGGNAARTTQALTSFFSPGAKQDIQLINTNGSWHINRTALNCNGSLDTGWVAGLFY
HCVE1      E------ST-----G-V-L--R---------------------E--------------

HCT27  444 YHKFNSSGCPERMASCRPLADFQQGWGPISYANGSGPEHRPYCWHYPPKPCGIVPAQNVC
HCVE1      ----------------------D----------T-----------------T--------

HCT27  504 GPVYCFTPSPVVVGTNKLGAPTYNWGSNETDVFVLNNTRPPLGNWFGCTWMNSSGFTKV
HCVE1      -------------A------Y--------C-D------------------V---------

HCT27  564 CGAPPCVIGGVGNNTLQCPTDCFRKHPDATYSRCAAGPWITPRCLVHYPYRLWHYPCTVN
HCVE1      -------------A------Y--------E------GS--------G-------------

HCT27  624 YTIVQIRMYVGGVDHRLEVACNWTRGERCDLDDRDRSELRLLLLSTTQWQVLPCSFTTLP
HCVE1      --LFKV-------------E---Q-------N---------SP-----------------

HCT27  684 ALTTGLIHLHQNIVDVQYLYGVGSSIVSWAIKWEYVILLFLLLANARICSCLW
HCVE1      ------------------------------------------D--V------
```

```
Met Ser Thr Asn Pro Lys Lys Asn Lys Arg Asn Thr Asn
 1               5                  10              15

Arg Arg Pro Gln Asp Val Lys Phe Pro Gly Gly Gln Ile Val Gly
         20                  25                  30

Gly Val Tyr Leu Leu Pro Arg Arg Gly Pro Arg Leu Gly Val Arg Ala
     35                  40                  45

Thr Arg Lys Thr Ser Glu Arg Ser Gln Pro Arg Gly Arg Arg Gln Pro
         50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
             85                  90                  95

Leu Leu Ser Pro Arg Gly Ser Arg Pro Ser Trp Gly Pro Thr Asp Pro
            100                 105                 110

Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
    145                 150                 155                 160

Gly Val Asn Tyr Ala Thr Gly Asn Leu Pro Gly Cys Ser Phe Ser Ile
            165                 170                 175
```

FIG. 9B

```
Phe Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
            195                 200                 205

Asn Ser Ser Ile Val Tyr Glu Ala Ala Asp Ala Ile Leu His Thr Pro
            210                 215                 220

Gly Cys Val Pro Cys Val Arg Glu Gly Asn Ala Ser Arg Cys Trp Val
            225                 230                 235                 240

Ala Met Thr Pro Thr Val Ala Thr Arg Asp Gly Lys Leu Pro Ala Thr
            245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Gly Cys
            290                 295                 300

Asn Cys Ser Ile Tyr Pro Gly His Ile Thr Gly His Arg Met Ala Trp
            305                 310                 315                 320

Asp Met Met Asn Trp Ser Pro Thr Thr Ala Leu Val Met Ala Gln
            325                 330                 335

Leu Leu Arg Ile Pro Gln Ala Ile Leu Asp Met Ile Ala Gly Ala His
            340                 345                 350
```

FIG. 9C

```
Trp Gly Val Leu Ala Gly Ile Ala Tyr Phe Ser Met Val Gly Asn Trp
        355                 360                 365
Ala Lys Val Leu Val Val Leu Leu Phe Ala Gly His Thr Val Ser Gly Phe Val
        370                 375                 380
Thr His Val Thr Gly Gly Ser Ala Gly His Thr Val Ser Gly Phe Val
        385                 390                 395                 400
Ser Leu Ala Pro Gly Ala Lys Gln Asn Val Gln Leu Ile Asn Thr
        405                 410                 415
Asn Gly Ser Trp His Leu Asn Ser Thr Ala Leu Asn Cys Asn Asp Ser
        420                 425                 430
Leu Asn Thr Gly Trp Leu Ala Gly Leu Phe Tyr His His Lys Phe Asn
        435                 440                 445
Ser Ser Gly Cys Pro Glu Arg Leu Ala Ser Cys Arg Pro Leu Thr Asp
        450                 455                 460
Phe Asp Gln Gly Trp Gly Pro Ile Ser Tyr Ala Asn Gly Ser Gly Pro
        465                 470                 475                 480
Asp Gln Arg Pro Tyr Cys Trp His Tyr Pro Pro Lys Pro Cys Gly Ile
        485                 490                 495
Val Pro Ala Lys Ser Val Cys Gly Pro Val Tyr Cys Phe Thr Pro Ser
        500                 505                 510
Pro Val Val Gly Thr Thr Asp Arg Ser Gly Ala Pro Thr Tyr Ser
        515                 520                 525
```

FIG. 9D

| | | | | | | | | |
|---|---|---|---|---|---|---|---|---|
| Trp | Gly | Glu | Asn | Asp | Thr | Asp | Val | Phe | Val | Leu | Asn | Asn | Thr | Arg | Pro |
| 530 | | | | 535 | | | | | 540 | | | | | | |
| Pro | Leu | Gly | Asn | Trp | Phe | Gly | Cys | Thr | Trp | Met | Asn | Ser | Thr | Gly | Phe |
| 545 | | | | 550 | | | | | 555 | | | | | | 560 |
| Thr | Lys | Val | Cys | Gly | Ala | Pro | Pro | Cys | Val | Ile | Gly | Gly | Ala | Gly | Asn |
| | | 565 | | | | | 570 | | | | | | | 575 | |
| Asn | Thr | Leu | His | Cys | Pro | Thr | Asp | Cys | Phe | Arg | Lys | His | Pro | Asp | Ala |
| | | 580 | | | | | 585 | | | | | | 590 | | |
| Thr | Tyr | Ser | Arg | Cys | Gly | Ser | Gly | Pro | Trp | Ile | Thr | Pro | Arg | Cys | Leu |
| | | 595 | | | | 600 | | | | | | 605 | | | |
| Val | Asp | Tyr | Pro | Tyr | Arg | Leu | Trp | His | Tyr | Pro | Cys | Thr | Ile | Asn | Tyr |
| | 610 | | | | | 615 | | | | | 620 | | | | |
| Thr | Ile | Phe | Lys | Ile | Arg | Met | Tyr | Val | Gly | Gly | Val | Glu | His | Arg | Leu |
| 625 | | | | | 630 | | | | | 635 | | | | | 640 |
| Glu | Ala | Ala | Cys | Asn | Trp | Thr | Arg | Gly | Glu | Arg | Cys | Asp | Leu | Glu | Asp |
| | | | 645 | | | | | 650 | | | | | | 655 | |
| Arg | Asp | Arg | Ser | Glu | Leu | Ser | Pro | Leu | Leu | Leu | Thr | Thr | Thr | Gln | Trp |
| | | 660 | | | | | 665 | | | | | | 670 | | |
| Gln | Val | Leu | Pro | Cys | Ser | Phe | Thr | Thr | Leu | Pro | Ala | Leu | Ser | Thr | Gly |
| | | 675 | | | | 680 | | | | | | 685 | | | |
| Leu | Ile | His | Leu | His | Gln | Asn | Ile | Val | Asp | Val | Gln | Tyr | Leu | Tyr | Gly |
| | 690 | | | | | 695 | | | | | 700 | | | | |

```
Val Gly Ser Ser Ile Ala Ser Trp Ala Ile Lys Trp Glu Tyr Val Val
705                 710                 715                 720
Leu Leu Phe Leu Leu Ala Asp Ala Arg Val Cys Ser Cys Leu Trp
        725                 730                 735
Met Met Leu Leu Ile Ser Gln Ala Ala Glu Ala Ala Leu Glu Asn Leu Val
            740                 745                 750
Ile Leu Asn Ala Ala Ser Leu Ala Gly Thr His Gly Leu Val Ser Phe
        755                 760                 765
Leu Val Phe Phe Cys Phe Ala Trp Tyr Leu Lys Gly Lys Trp Val Pro
        770                 775                 780
Gly Ala Val Tyr Thr Phe Tyr Gly Met Trp Pro Leu Leu Leu Leu
785                 790                 795                 800
Leu Ala Leu Pro Gln Arg Ala Tyr Ala Leu Asp Thr Glu Val Ala Ala
            805                 810                 815
Ser Cys Gly Gly Val Val Leu Val Gly Leu Met Ala Leu Thr Leu Ser
        820                 825                 830
Pro Tyr Tyr Lys Arg Tyr Ile Ser Trp Cys Leu Trp Trp Leu Gln Tyr
        835                 840                 845
Phe Leu Thr Arg Val Glu Ala Gln Leu His Val Trp Ile Pro Pro Leu
        850                 855                 860
Asn Val Arg Gly Gly Arg Asp Ala Val Ile Leu Met Cys Ala Val
865                 870                 875                 880
```

His Pro Thr Leu Val Phe Asp Ile Thr Lys Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ile Gly Gly His Tyr Val Gln Met Val Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
            965                 970                 975

Ser Gln Met Glu Thr Lys Leu Ile Thr Trp Gly Ala Asp Thr Ala Ala
        980                 985                 990

Cys Gly Asp Ile Ile Asn Gly Leu Pro Val Ser Ala Arg Arg Gly Arg
    995                 1000                1005

Glu Ile Leu Leu Gly Pro Ala Asp Gly Met Val Ser Lys Gly Trp Arg
1010                1015                1020

Leu Leu Ala Pro Ile Thr Ala Tyr Ala Gln Gln Thr Arg Gly Leu Leu
            1025                1030                1035                1040

Gly Cys Ile Ile Thr Ser Leu Thr Gly Arg Asp Lys Asn Gln Val Glu
        1045                1050                1055

Gly Glu Val Gln Ile Val Ser Thr Ala Ala Gln Thr Phe Leu Ala Thr
1060                    1065                    1070

Cys Ile Asn Gly Val Cys Trp Thr Val Tyr His Gly Ala Gly Thr Arg
1075                    1080                    1085

Thr Ile Ala Ser Pro Lys Gly Pro Val Ile Gln Met Tyr Thr Asn Val
1090                    1095                    1100

Asp Gln Asp Leu Val Gly Trp Pro Ala Pro Gln Gly Ser Arg Ser Leu
1105                    1110                    1115                    1120

Thr Pro Cys Thr Cys Gly Ser Ser Asp Leu Tyr Leu Val Thr Arg His
1125                    1130                    1135

Ala Asp Val Ile Pro Val Arg Arg Arg Gly Asp Ser Arg Gly Ser Leu
1140                    1145                    1150

Leu Ser Pro Arg Pro Ile Ser Tyr Leu Lys Gly Ser Ser Gly Gly Pro
1155                    1160                    1165

Leu Leu Cys Pro Ala Gly His Ala Val Gly Ile Phe Arg Ala Ala Val
1170                    1175                    1180

Cys Thr Arg Gly Val Ala Lys Ala Val Asp Phe Ile Pro Val Glu Asn
1185                    1190                    1195                    1200

Leu Glu Thr Thr Met Arg Ser Pro Val Phe Thr Asp Asn Ser Ser Pro
1205                    1210                    1215

Pro Val Val Pro Gln Ser Phe Gln Val Ala His Leu His Ala Pro Thr
1220                    1225                    1230

FIG. 9G

Gly Ser Gly Lys Ser Thr Lys Val Pro Ala Ala Tyr Ala Ala Gln Gly
                1235                1240                1245

Tyr Lys Val Leu Val Leu Asn Pro Ser Val Ala Ala Thr Leu Gly Phe
                1250                1255                1260

Gly Ala Tyr Met Ser Lys Ala His Gly Ile Asp Pro Asn Ile Arg Thr
                1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
                1300                1305                1310

Ile Ile Cys Asp Glu Cys His Ser Thr Asp Ala Thr Ser Ile Leu Gly
                1315                1320                1325

Ile Gly Thr Val Leu Asp Gln Ala Glu Thr Ala Gly Ala Arg Leu Val
                1330                1335                1340

Val Leu Ala Thr Ala Thr Pro Pro Gly Ser Val Thr Val Pro His Pro
                1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
                1380                1385                1390

Phe Cys His Ser Lys Lys Lys Cys Asp Glu Leu Ala Ala Lys Leu Val
                1395                1400                1405

FIG. 9H

Ala Leu Gly Ile Asn Ala Val Ala Tyr Tyr Arg Gly Leu Asp Val Ser
1410                     1415                    1420

Val Ile Pro Thr Ser Gly Asp Val Val Val Ala Thr Asp Ala Leu
1425                    1430                    1435         1440

Met Thr Gly Tyr Thr Gly Asp Phe Asp Ser Val Ile Asp Cys Asn Thr
1445                    1450                    1455

Cys Val Thr Gln Thr Val Asp Phe Ser Leu Asp Pro Thr Phe Thr Ile
1460                    1465                    1470

Glu Thr Ile Thr Leu Pro Gln Asp Ala Val Ser Arg Thr Gln Arg Arg
1475                    1480                    1485

Gly Arg Thr Gly Arg Gly Lys Pro Gly Ile Tyr Arg Phe Val Ala Pro
1490                    1495                    1500

Gly Glu Arg Pro Ser Gly Met Phe Asp Ser Ser Val Leu Cys Glu Cys
1505                    1510                    1515         1520

Tyr Asp Ala Gly Cys Ala Trp Tyr Glu Leu Thr Pro Ala Glu Thr Thr
1525                    1530                    1535

Val Arg Leu Arg Ala Tyr Met Asn Thr Pro Gly Leu Pro Val Cys Gln
1540                    1545                    1550

Asp His Leu Glu Phe Trp Glu Gly Val Phe Thr Gly Leu Thr His Ile
1555                    1560                    1565

Asp Ala His Phe Leu Ser Gln Thr Lys Gln Ser Gly Glu Asn Leu Pro
1570                    1575                    1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
        1620                1625                1630

Asn Glu Ile Thr Leu Thr His Pro Val Thr Lys Tyr Ile Met Thr Cys
    1635                1640                1645

Met Ser Ala Asp Leu Glu Val Val Thr Ser Thr Trp Val Leu Val Gly
1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
            1685                1690                1695

Asp Arg Glu Val Leu Tyr Arg Glu Phe Asp Glu Met Glu Glu Cys Ser
        1700                1705                1710

Gln His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala Glu
1730                1735                1740

Val Ile Ala Pro Ala Val Gln Thr Asn Trp Gln Lys Leu Glu Thr Phe
1745                1750                1755                1760

FIG. 9K

Trp Ala Lys His Met Trp Asn Phe Ile Ser Gly Ile Gln Tyr Leu Ala
              1765                1770                1775

Gly Leu Ser Thr Leu Pro Gly Asn Pro Ala Ile Ala Ser Leu Met Ala
              1780                1785                1790

Phe Thr Ala Val Thr Ser Pro Leu Thr Ser Gln Thr Leu Leu
              1795                1800            1805

Phe Asn Ile Leu Gly Gly Trp Val Ala Ala Gln Leu Ala Ala Pro Gly
              1810                1815                1820

Ala Ala Thr Ala Phe Val Gly Ala Gly Leu Ala Gly Ala Ala Ile Gly
              1825                1830                1835            1840

Ser Val Gly Leu Gly Lys Val Leu Ile Asp Ile Leu Ala Gly Tyr Gly
              1845                1850                1855

Ala Gly Val Ala Gly Ala Leu Val Ala Phe Lys Ile Met Ser Gly Glu
              1860                1865                1870

Val Pro Ser Thr Glu Asp Leu Val Asn Leu Leu Pro Ala Ile Leu Ser
              1875                1880                1885

Pro Gly Ala Leu Val Val Gly Val Val Cys Ala Ala Ile Leu Arg Arg
              1890                1895                1900

His Val Gly Pro Gly Glu Gly Ala Val Gln Trp Met Asn Arg Leu Ile
              1905                1910                1915            1920

Ala Phe Ala Ser Arg Gly Asn His Val Ser Pro Thr His Tyr Val Pro
              1925                1930                1935

FIG. 9L

```
Glu Ser Asp Ala Ala Ala Arg Val Thr Ala Ile Leu Ser Ser Leu Thr
           1940                1945                1950
Val Thr Gln Leu Leu Arg Arg Leu His Gln Trp Ile Ser Ser Glu Cys
           1955                1960                1965
Thr Thr Pro Cys Ser Gly Ser Trp Leu Arg Asp Ile Trp Asp Trp Ile
           1970                1975                1980
Cys Glu Val Leu Ser Asp Phe Lys Thr Trp Leu Lys Ala Lys Leu Met
           1985                1990                1995            2000
Pro Gln Leu Pro Gly Ile Pro Phe Val Ser Cys Gln Arg Gly Tyr Lys
           2005                2010                2015
Gly Val Trp Arg Val Asp Gly Ile Met His His Thr Arg Cys His Cys Gly
           2020                2025                2030
Ala Glu Ile Thr Gly His Val Lys Asn Gly Thr Met Arg Ile Val Gly
           2035                2040                2045
Pro Arg Thr Cys Arg Asn Met Trp Ser Gly Thr Phe Pro Ile Asn Ala
           2050                2055                2060
Tyr Thr Thr Gly Pro Cys Thr Pro Leu Pro Ala Pro Asn Tyr Thr Phe
           2065                2070                2075            2080
Ala Leu Trp Arg Val Ser Ala Glu Glu Tyr Val Glu Ile Arg Gln Val
           2085                2090                2095
Gly Asp Phe His Tyr Val Thr Gly Met Thr Thr Asp Asn Leu Lys Cys
           2100                2105                2110
```

Pro Cys Gln Val Pro Ser Pro Glu Phe Phe Thr Glu Leu Asp Gly Val
2115                    2120                    2125

Arg Leu His Arg Phe Ala Pro Pro Cys Lys Pro Leu Leu Arg Glu Glu
2130                    2135                    2140

Val Ser Phe Arg Val Gly Leu His Glu Tyr Pro Val Gly Ser Gln Leu
2145                    2150                    2155                2160

Pro Cys Glu Pro Asp Val Ala Val Leu Thr Ser Met Leu Thr
2165                    2170                    2175

Asp Pro Ser His Ile Thr Ala Glu Ala Ala Gly Arg Arg Leu Ala Arg
2180                    2185                    2190

Gly Ser Pro Pro Ser Val Ala Ser Ser Ser Ala Ser Gln Leu Ser Ala
2195                    2200                    2205

Pro Ser Leu Lys Ala Thr Cys Thr Ala Asn His Asp Ser Pro Asp Ala
2210                    2215                    2220

Glu Leu Ile Glu Ala Asn Leu Leu Trp Arg Gln Glu Met Gly Gly Asn
2225                    2230                    2235                2240

Ile Thr Arg Val Glu Ser Glu Asn Lys Val Val Ile Leu Asp Ser Phe
2245                    2250                    2255

Asp Pro Leu Val Ala Glu Glu Asp Glu Arg Glu Ile Ser Val Pro Ala
2260                    2265                    2270

Glu Ile Leu Arg Lys Ser Arg Arg Phe Ala Gln Ala Leu Pro Val Trp
2275                    2280                    2285

FIG. 9M

```
Ala Arg Pro Asp Tyr Asn Pro Pro Leu Val Glu Thr Trp Lys Lys Pro
        2290                2295                2300

Asp Tyr Glu Pro Pro Val Val His Gly Cys Pro Leu Pro Pro Pro Lys
        2305                2310                2315            2320

Ser Pro Pro Val Pro Pro Arg Lys Lys Arg Thr Val Val Leu Thr
        2325                2330                2335

Glu Ser Thr Leu Ser Thr Ala Leu Ala Glu Leu Ala Thr Arg Ser Phe
        2340                2345                2350

Gly Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Ala Glu Ser
        2370                2375                2380

Tyr Ser Ser Met Pro Pro Leu Glu Gly Glu Pro Gly Asp Pro Asp Leu
        2385                2390                2395            2400

Ser Asp Gly Ser Trp Ser Thr Val Ser Ser Gly Ala Asn Ala Glu Asp
        2405                2410                2415

Val Val Cys Cys Ser Met Ser Tyr Ser Trp Thr Gly Ala Leu Val Thr
        2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
        2450                2455                2460
```

FIG. 9N

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
2485                2490                2495

Lys Val Lys Ala Asn Leu Leu Ser Val Glu Glu Ala Cys Ser Leu Thr
2500                2505                2510

Pro Pro His Ser Ala Lys Ser Lys Phe Gly Tyr Gly Ala Lys Asp Val
2515                2520                2525

Arg Cys His Ala Arg Lys Ala Val Thr His Ile Asn Ser Val Trp Lys
2530                2535                2540

Asp Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
2565                2570                2575

Ala Arg Leu Ile Val Phe Pro Asp Leu Gly Val Arg Val Cys Glu Lys
2580                2585                2590

Met Ala Leu Tyr Asp Val Val Thr Lys Leu Pro Leu Ala Val Met Gly
2595                2600                2605

Ser Ser Tyr Gly Phe Gln Tyr Ser Pro Gly Gln Arg Val Glu Phe Leu
2610                2615                2620

Val Gln Ala Trp Lys Ser Lys Lys Thr Pro Met Gly Phe Ser Tyr Asp
2625                2630                2635                2640

```
Thr Arg Cys Phe Asp Ser Thr Val Thr Glu Ser Asp Ile Arg Thr Glu
            2645                2650                2655
Glu Ala Ile Tyr Gln Cys Cys Asp Pro Leu Asp Pro Gln Ala Arg Val Ala
            2660                2665                2670
Ile Lys Ser Leu Thr Glu Arg Leu Tyr Val Gly Gly Pro Leu Thr Asn
            2675                2680                2685
Ser Arg Gly Glu Asn Cys Gly Tyr Arg Arg Cys Arg Ala Ser Gly Val
            2690                2695                2700
Leu Thr Thr Ser Cys Gly Asn Thr Leu Thr Cys Tyr Ile Lys Ala Arg
            2705                2710                2715                2720
Ala Ala Cys Arg Ala Ala Gly Leu Gln Asp Cys Thr Met Leu Val Cys
            2725                2730                2735
Gly Asp Asp Leu Val Val Ile Cys Glu Ser Ala Gly Val Gln Glu Asp
            2740                2745                2750
Ala Ala Ser Leu Arg Ala Phe Thr Glu Ala Met Thr Arg Tyr Ser Ala
            2755                2760                2765
Pro Pro Gly Asp Pro Pro Gln Pro Glu Tyr Asp Leu Glu Leu Ile Thr
            2770                2775                2780
Ser Cys Ser Ser Asn Val Ser Val Ala His Asp Gly Ala Gly Lys Arg
            2785                2790                2795                2800
Val Tyr Tyr Leu Thr Arg Asp Pro Thr Thr Pro Leu Ala Arg Ala Ala
            2805                2810                2815
```

Trp Glu Thr Ala Arg His Thr Pro Val Asn Ser Trp Leu Gly Asn Ile
2820                                2825                    2830

Ile Met Phe Ala Pro Thr Leu Trp Ala Arg Met Ile Leu Met Thr His
    2835                    2840                    2845

Phe Phe Ser Val Leu Ile Ala Arg Asp Gln Leu Glu Gln Ala Leu Asp
2850                    2855                    2860

Cys Glu Ile Tyr Gly Ala Cys Tyr Ser Ile Glu Pro Leu Asp Leu Pro
2865                    2870                    2875                2880

Pro Ile Ile Gln Arg Leu His Gly Leu Ser Ala Phe Ser Leu His Ser
            2885                    2890                    2895

Tyr Ser Pro Gly Glu Ile Asn Arg Val Ala Ala Cys Leu Arg Lys Leu
2900                    2905                    2910

Gly Val Pro Pro Leu Arg Ala Trp Arg His Arg Ala Arg Ser Val Arg
            2915                    2920                    2925

Ala Arg Leu Leu Ala Arg Gly Gly Arg Ala Ala Ile Cys Gly Lys Tyr
2930                    2935                    2940

Leu Phe Asn Trp Ala Val Arg Thr Lys Leu Lys Leu Thr Pro Ile Ala
2945                    2950                    2955                2960

Ala Ala Gly Gln Leu Asp Leu Ser Gly Trp Phe Thr Ala Gly Tyr Ser
            2965                    2970                    2975

Gly Gly Asp Ile Tyr His Ser Val Ser His Ala Arg Pro Arg Trp Ile
2980                    2985                    2990

FIG. 9Q

Trp Phe Cys Leu Leu Leu Leu Ala Ala Gly Val Gly Ile Tyr Leu Leu
             2995                3000                3005

Pro Asn Arg
    3010

FIG. 9R

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GGTGCTCACT GGGGAGTCCT 20

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CATTGCAGTT CAGGGCCGTG CTA 23

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

TCCATGGTGG GGAACTGGGC 20

( 2 ) INFORMATION FOR SEQ ID NO:4:

-continued ( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

TGCCAACTGC CATTGGTGTT                                     20

( 2 ) INFORMATION FOR SEQ ID NO:5:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

TAACGGGCTG AGCTCGGA                                      18

( 2 ) INFORMATION FOR SEQ ID NO:6:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

CAATTGGTTC GGTTGTACC                                     19

( 2 ) INFORMATION FOR SEQ ID NO:7:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

CGTCCAGTTC GGAGGCAGCT TC                               22

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

CAGGGCAGTA TCTGCCACTC                                     20

( 2 ) INFORMATION FOR SEQ ID NO:9:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear (i i) MOLECULE TYPE: DNA (genomic)

(x i) SEQUENCE DESCRIPTION: SEQ ID NO:9:

TGAGACGGAC GTGCTGCTCC T                                              21

(2) INFORMATION FOR SEQ ID NO:10:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:10:

TTTGATGTAC CAGGCGGCGC A                                              21

(2) INFORMATION FOR SEQ ID NO:11:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:11:

GGATCCGCTA GCCATACCCG CGTGACGGGG GGGGTGCAA                            39

(2) INFORMATION FOR SEQ ID NO:12:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:12:

GGATCCTCTA GATTACTCTT CTGACCTATC CCTGTCCTCC AAGTC                     45

(2) INFORMATION FOR SEQ ID NO:13:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:13:

CAACTGGTTC GGCTGTACA                                                  19

(2) INFORMATION FOR SEQ ID NO:14:

(i) SEQUENCE CHARACTERISTICS:
      (A) LENGTH: 480 amino acids
      (B) TYPE: amino acid
      (C) STRANDEDNESS: single
      (D) TOPOLOGY: linear (i i) MOLECULE TYPE: protein (x i) SEQUENCE DESCRIPTION: SEQ ID NO:14:

| | | | | | | | | | | | | | | |
|---|---|---|---|---|---|---|---|---|---|---|---|---|---|---|
| Lys 1 | Val | Leu | Val | Val 5 | Leu | Leu | Leu | Phe | Ala 10 | Gly | Val | Asp | Ala | Glu Thr 15 |
| His | Val | Thr | Gly 20 | Gly | Ser | Ala | Gly | His 25 | Thr | Val | Ser | Gly | Phe 30 | Val Ser |
| Leu | Leu | Ala 35 | Pro | Gly | Ala | Lys | Gln 40 | Asn | Val | Gln | Leu | Ile 45 | Asn | Thr Asn |
| Gly | Ser 50 | Trp | His | Leu | Asn | Ser 55 | Thr | Ala | Leu | Asn | Cys 60 | Asn | Asp | Ser Leu |
| Asn 65 | Thr | Gly | Trp | Leu | Ala 70 | Gly | Leu | Phe | Tyr | His 75 | His | Lys | Phe | Asn Ser 80 |
| Ser | Gly | Cys | Pro | Glu 85 | Arg | Leu | Ala | Ser | Cys 90 | Arg | Pro | Leu | Thr | Asp Phe 95 |
| Asp | Gln | Gly | Trp 100 | Gly | Pro | Ile | Ser | Tyr 105 | Ala | Asn | Gly | Ser | Gly 110 | Pro Asp |
| Gln | Arg | Pro 115 | Tyr | Cys | Trp | His | Tyr 120 | Pro | Pro | Lys | Pro | Cys 125 | Gly | Ile Val |
| Pro | Ala 130 | Lys | Ser | Val | Cys | Gly 135 | Pro | Val | Tyr | Cys | Phe 140 | Thr | Pro | Ser Pro |
| Val 145 | Val | Val | Gly | Thr | Thr 150 | Asp | Arg | Ser | Gly | Ala 155 | Pro | Thr | Tyr | Ser Trp 160 |
| Gly | Glu | Asn | Asp | Thr 165 | Asp | Val | Phe | Val | Leu 170 | Asn | Asn | Thr | Arg | Pro Pro 175 |
| Leu | Gly | Asn | Trp 180 | Phe | Gly | Cys | Thr | Trp 185 | Met | Asn | Ser | Thr | Gly 190 | Phe Thr |
| Lys | Val | Cys 195 | Gly | Ala | Pro | Pro | Cys 200 | Val | Ile | Gly | Gly | Ala 205 | Gly | Asn Asn |
| Thr | Leu 210 | His | Cys | Pro | Thr | Asp 215 | Cys | Phe | Arg | Lys | His 220 | Pro | Asp | Ala Thr |
| Tyr 225 | Ser | Arg | Cys | Gly | Ser 230 | Gly | Pro | Trp | Ile | Thr 235 | Pro | Arg | Cys | Leu Val 240 |
| Asp | Tyr | Pro | Tyr | Arg 245 | Leu | Trp | His | Tyr | Pro 250 | Cys | Thr | Ile | Asn | Tyr Thr 255 |
| Ile | Phe | Lys | Ile 260 | Arg | Met | Tyr | Val | Gly 265 | Gly | Val | Glu | His | Arg 270 | Leu Glu |
| Ala | Ala | Cys 275 | Asn | Trp | Thr | Arg | Gly 280 | Glu | Arg | Cys | Asp | Leu 285 | Glu | Asp Arg |
| Asp | Arg 290 | Ser | Glu | Leu | Ser | Pro 295 | Leu | Leu | Leu | Thr | Thr 300 | Thr | Gln | Trp Gln |
| Val 305 | Leu | Pro | Cys | Ser | Phe 310 | Thr | Thr | Leu | Pro | Ala 315 | Leu | Ser | Thr | Gly Leu 320 |
| Ile | His | Leu | His | Gln 325 | Asn | Ile | Val | Asp | Val 330 | Gln | Tyr | Leu | Tyr | Gly Val 335 |
| Gly | Ser | Ser | Ile 340 | Ala | Ser | Trp | Ala | Ile 345 | Lys | Trp | Glu | Tyr | Val 350 | Val Leu |
| Leu | Phe | Leu 355 | Leu | Leu | Ala | Asp | Ala 360 | Arg | Val | Cys | Ser | Cys 365 | Leu | Trp Met |
| Met | Leu 370 | Leu | Ile | Ser | Gln | Ala 375 | Glu | Ala | Ala | Leu | Glu 380 | Asn | Leu | Val Ile |
| Leu 385 | Asn | Ala | Ala | Ser | Leu 390 | Ala | Gly | Thr | His | Gly 395 | Leu | Val | Ser | Phe Leu 400 |
| Val | Phe | Phe | Cys | Phe 405 | Ala | Trp | Tyr | Leu | Lys 410 | Gly | Lys | Trp | Val | Pro Gly 415 |
| Ala | Val | Tyr | Thr 420 | Phe | Tyr | Gly | Met | Trp 425 | Pro | Leu | Leu | Leu | Leu 430 | Leu Leu |

Ala Leu Pro Gln Arg Ala Tyr Ala Leu Asp Thr Glu Val Ala Ala Ser
        435                 440                 445

Cys Gly Gly Val Val Leu Gly Leu Met Ala Leu Thr Leu Ser Pro
    450                 455                 460

Tyr Tyr Lys Arg Tyr Ile Ser Trp Cys Leu Trp Trp Leu Gln Tyr Phe
465                 470                 475                 480

( 2 ) INFORMATION FOR SEQ ID NO:15:

( i ) SEQUENCE CHARACTERISTICS:
         ( A ) LENGTH: 278 amino acids
         ( B ) TYPE: amino acid
         ( C ) STRANDEDNESS: single
         ( D ) TOPOLOGY: linear ( i i ) MOLECULE TYPE: protein ( x i ) SEQUENCE DESCRIPTION: SEQ ID NO:15:

Lys Val Leu Val Val Leu Leu Leu Phe Ala Gly Val Asp Ala Glu Thr
1               5                   10                  15

Thr Val Thr Gly Gly Ser Ala Ala His Gly Ala Leu Gly Ile Ala Ser
            20                  25                  30

Leu Phe Asn Gln Gly Ala Arg Gln Asn Ile Gln Leu Ile Asn Thr Asn
        35                  40                  45

Gly Ser Trp His Ile Asn Ser Thr Ala Leu Asn Cys Asn Asp Ser Leu
    50                  55                  60

Asn Thr Gly Trp Ile Ala Gly Leu Phe Tyr Tyr His Lys Phe Asn Ser
65                  70                  75                  80

Ser Gly Cys Pro Glu Arg Leu Ala Ser Cys Arg Pro Leu Thr Asp Phe
                    85                  90                  95

Asp Gln Gly Trp Gly Pro Ile Ser Tyr Ala Asn Gly Ser Gly Pro Asp
                100                 105                 110

Gln Arg Pro Tyr Cys Trp His Tyr Pro Pro Lys Pro Cys Gly Ile Val
            115                 120                 125

Pro Ala Lys Ser Val Cys Gly Pro Val Tyr Cys Phe Thr Pro Ser Pro
    130                 135                 140

Val Val Val Gly Thr Thr Asp Arg Ser Gly Ala Pro Thr Tyr Asn Trp
145                 150                 155                 160

Gly Ala Asn Asp Thr Asp Val Phe Val Leu Asn Asn Thr Arg Pro Pro
                165                 170                 175

Leu Gly Asn Trp Phe Gly Cys Thr Trp Met Asn Ser Thr Gly Phe Thr
                180                 185                 190

Lys Val Cys Gly Ala Pro Pro Cys Val Ile Gly Gly Val Gly Asn Asn
            195                 200                 205

Thr Leu His Cys Pro Thr Asp Cys Phe Arg Lys His Pro Asp Ala Thr
    210                 215                 220

Tyr Ser Arg Cys Gly Ser Gly Pro Trp Ile Thr Pro Arg Cys Leu Val
225                 230                 235                 240

Asn Tyr Pro Tyr Arg Leu Trp His Tyr Pro Cys Thr Ile Asn Tyr Thr
                245                 250                 255

Ile Phe Lys Val Arg Met Tyr Val Gly Gly Val Glu His Arg Leu Glu
            260                 265                 270

Ala Ala Cys Asn Trp Thr
            275

( 2 ) INFORMATION FOR SEQ ID NO:16:

( i ) SEQUENCE CHARACTERISTICS:
  ( A ) LENGTH: 269 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:16:

```
Lys Val Leu Ile Val Met Leu Leu Phe Ala Gly Val Asp Gly His Thr
1               5                   10                  15

Arg Val Thr Gly Gly Val Gln Gly His Val Thr Ser Thr Leu Thr Ser
            20                  25                  30

Leu Phe Arg Pro Gly Ala Ser Gln Lys Ile Gln Leu Val Asn Thr Asn
        35                  40                  45

Gly Ser Trp His Ile Asn Arg Thr Ala Leu Asn Cys Asn Asp Ser Leu
    50                  55                  60

Gln Thr Gly Phe Leu Ala Ala Leu Phe Tyr Thr His Lys Phe Asn Ala
65                  70                  75                  80

Ser Gly Cys Pro Glu Arg Met Ala Ser Cys Arg Ser Ile Asp Lys Phe
                85                  90                  95

Asp Gln Gly Trp Gly Pro Ile Thr Tyr Ala Gln Pro Asp Asn Ser Asp
            100                 105                 110

Gln Arg Pro Tyr Cys Trp His Tyr Ala Pro Arg Gln Cys Gly Ile Val
        115                 120                 125

Pro Ala Ser Gln Val Cys Gly Pro Val Tyr Cys Phe Thr Pro Ser Pro
    130                 135                 140

Val Val Val Gly Thr Thr Asp Arg Phe Gly Ala Pro Thr Tyr Asn Trp
145                 150                 155                 160

Gly Asp Asn Glu Thr Asp Val Leu Leu Leu Asn Asn Thr Arg Pro Pro
                165                 170                 175

His Gly Asn Trp Phe Gly Cys Thr Trp Met Asn Ser Thr Gly Phe Thr
            180                 185                 190

Lys Thr Cys Gly Gly Pro Pro Cys Asn Ile Gly Gly Val Gly Asn Asn
        195                 200                 205

Thr Leu Thr Cys Pro Thr Asp Cys Phe Arg Lys His Pro Glu Ala Thr
    210                 215                 220

Tyr Thr Lys Cys Gly Ser Gly Pro Trp Leu Thr Pro Arg Cys Leu Val
225                 230                 235                 240

Asp Tyr Pro Tyr Arg Leu Trp His Tyr Pro Cys Thr Val Asn Phe Thr
                245                 250                 255

Ile Phe Lys Val Arg Met Tyr Val Gly Gly Val Glu His
            260                 265
```

( 2 ) INFORMATION FOR SEQ ID NO:17:

( i ) SEQUENCE CHARACTERISTICS:
    ( A ) LENGTH: 367 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:17:

```
Lys Val Leu Leu Val Leu Leu Leu Phe Ala Gly Val Asp Ala Glu Thr
1               5                   10                  15

Tyr Thr Thr Gly Gly Ser Thr Ala Arg Thr Thr Gln Gly Leu Val Ser
            20                  25                  30
```

```
Leu Phe Ser Arg Gly Ala Lys Gln Asp Ile Gln Leu Ile Asn Thr Asn
         35                  40                  45

Gly Ser Trp His Ile Asn Arg Thr Ala Leu Asn Cys Asn Glu Ser Leu
         50                  55                  60

Asp Thr Gly Trp Val Ala Gly Leu Phe Tyr Tyr His Lys Phe Asn Ser
 65                  70                  75                   80

Ser Gly Cys Pro Glu Arg Met Ala Ser Cys Arg Pro Leu Ala Asp Phe
                 85                  90                   95

Asp Gln Gly Trp Gly Pro Ile Ser Tyr Ala Asn Gly Thr Gly Pro Glu
             100                 105                 110

His Arg Pro Tyr Cys Trp His Tyr Pro Pro Lys Pro Cys Gly Ile Val
         115                 120                 125

Pro Ala Gln Thr Val Cys Gly Pro Val Tyr Cys Phe Thr Pro Ser Pro
     130                 135                 140

Val Val Val Gly Thr Thr Asn Lys Leu Gly Ala Pro Thr Tyr Asn Trp
145                 150                 155                 160

Gly Cys Asn Asp Thr Asp Val Phe Val Leu Asn Asn Thr Arg Pro Pro
                 165                 170                 175

Leu Gly Asn Trp Phe Gly Cys Thr Trp Val Asn Ser Ser Gly Phe Thr
             180                 185                 190

Lys Val Cys Gly Ala Pro Pro Cys Val Ile Gly Gly Ala Gly Asn Asn
         195                 200                 205

Thr Leu Tyr Cys Pro Thr Asp Cys Phe Arg Lys His Pro Glu Ala Thr
     210                 215                 220

Tyr Ser Arg Cys Gly Ser Gly Pro Trp Ile Thr Pro Arg Cys Leu Val
225                 230                 235                 240

Gly Tyr Pro Tyr Arg Leu Trp His Tyr Pro Cys Thr Val Asn Tyr Thr
                 245                 250                 255

Leu Phe Lys Val Arg Met Tyr Val Gly Gly Val Glu His Arg Leu Gln
             260                 265                 270

Val Ala Cys Asn Trp Thr Arg Gly Glu Arg Cys Asn Leu Asp Asp Arg
         275                 280                 285

Asp Arg Ser Glu Leu Ser Pro Leu Leu Leu Ser Thr Thr Gln Trp Gln
     290                 295                 300

Val Leu Pro Cys Ser Phe Thr Thr Leu Pro Ala Leu Thr Thr Gly Leu
305                 310                 315                 320

Ile His Leu His Gln Asn Ile Val Asp Val Gln Tyr Leu Tyr Gly Val
                 325                 330                 335

Gly Ser Ser Ile Val Ser Trp Ala Ile Lys Trp Glu Tyr Val Ile Leu
             340                 345                 350

Leu Phe Leu Leu Leu Ala Asp Ala Arg Val Cys Ser Cys Leu Trp
         355                 360                 365
```

(2) INFORMATION FOR SEQ ID NO:18:

(i) SEQUENCE CHARACTERISTICS:
        (A) LENGTH: 480 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Lys Val Leu Ile Val Met Leu Leu Phe Ala Gly Val Asp Gly His Thr
 1                   5                  10                  15

His Val Thr Gly Gly Arg Val Ala Ser Ser Thr Gln Ser Leu Val Ser
```

```
                            20                        25                        30
    Trp  Leu  Ser  Gln  Gly  Pro  Ser  Gln  Lys  Ile  Gln  Leu  Val  Asn  Thr  Asn
              35                        40                        45
    Gly  Ser  Trp  His  Ile  Asn  Arg  Thr  Ala  Leu  Asn  Cys  Asn  Asp  Ser  Leu
         50                        55                        60
    Gln  Thr  Gly  Phe  Ile  Ala  Ala  Leu  Phe  Tyr  Ala  His  Arg  Phe  Asn  Ala
    65                        70                        75                        80
    Ser  Gly  Cys  Pro  Glu  Arg  Met  Ala  Ser  Cys  Arg  Pro  Ile  Asp  Glu  Phe
                        85                        90                        95
    Ala  Gln  Gly  Trp  Gly  Pro  Ile  Thr  His  Asp  Met  Pro  Glu  Ser  Ser  Asp
                   100                       105                       110
    Gln  Arg  Pro  Tyr  Cys  Trp  His  Tyr  Ala  Pro  Arg  Pro  Cys  Gly  Ile  Val
                   115                       120                       125
    Pro  Ala  Ser  Gln  Val  Cys  Gly  Pro  Val  Tyr  Cys  Phe  Thr  Pro  Ser  Pro
         130                       135                       140
    Val  Val  Val  Gly  Thr  Thr  Asp  Arg  Phe  Gly  Ala  Pro  Thr  Tyr  Ser  Trp
    145                       150                       155                       160
    Gly  Glu  Asn  Glu  Thr  Asp  Val  Leu  Leu  Leu  Ser  Asn  Thr  Arg  Pro  Pro
                        165                       170                       175
    Gln  Gly  Asn  Trp  Phe  Gly  Cys  Thr  Trp  Met  Asn  Ser  Thr  Gly  Phe  Thr
                   180                       185                       190
    Lys  Thr  Cys  Gly  Gly  Pro  Pro  Cys  Asn  Ile  Gly  Gly  Val  Gly  Asn  Asn
              195                       200                       205
    Thr  Leu  Val  Cys  Pro  Thr  Asp  Cys  Phe  Arg  Lys  His  Pro  Glu  Ala  Thr
         210                       215                       220
    Tyr  Thr  Lys  Cys  Gly  Ser  Gly  Pro  Trp  Leu  Thr  Pro  Arg  Cys  Met  Val
    225                       230                       235                       240
    Asp  Tyr  Pro  Tyr  Arg  Leu  Trp  His  Tyr  Pro  Cys  Thr  Val  Asn  Phe  Thr
                        245                       250                       255
    Val  Phe  Lys  Val  Arg  Met  Tyr  Val  Gly  Gly  Val  Glu  His  Arg  Leu  Asn
                   260                       265                       270
    Ala  Ala  Cys  Asn  Trp  Thr  Arg  Gly  Glu  Arg  Cys  Asp  Leu  Glu  Asp  Arg
              275                       280                       285
    Asp  Arg  Ser  Glu  Leu  Ser  Pro  Leu  Leu  Leu  Ser  Thr  Thr  Glu  Trp  Gln
         290                       295                       300
    Ile  Leu  Pro  Cys  Ser  Phe  Thr  Thr  Leu  Pro  Ala  Leu  Ser  Thr  Gly  Leu
    305                       310                       315                       320
    Ile  His  Leu  His  Arg  Asn  Ile  Val  Asp  Val  Gln  Tyr  Leu  Tyr  Gly  Ile
                        325                       330                       335
    Gly  Ser  Ala  Val  Val  Ser  Phe  Ala  Ile  Lys  Trp  Glu  Tyr  Ile  Leu  Leu
                   340                       345                       350
    Leu  Phe  Leu  Leu  Leu  Ala  Asp  Ala  Arg  Val  Cys  Ala  Cys  Leu  Trp  Met
              355                       360                       365
    Met  Leu  Leu  Ile  Ala  Gln  Ala  Glu  Ala  Thr  Leu  Glu  Asn  Leu  Val  Val
         370                       375                       380
    Leu  Asn  Ala  Ala  Ser  Val  Ala  Gly  Ala  His  Gly  Leu  Leu  Ser  Phe  Leu
    385                       390                       395                       400
    Val  Phe  Phe  Cys  Ala  Ala  Trp  Tyr  Ile  Lys  Gly  Arg  Leu  Val  Pro  Gly
                        405                       410                       415
    Ala  Ala  Tyr  Ala  Leu  Tyr  Gly  Val  Trp  Pro  Leu  Leu  Leu  Leu  Leu  Leu
                   420                       425                       430
    Ala  Leu  Pro  Pro  Arg  Ala  Tyr  Ala  Met  Asp  Arg  Glu  Met  Ala  Ala  Ser
              435                       440                       445
```

```
          Cys   Gly   Gly   Ala   Val   Phe   Val   Gly   Leu   Val   Leu   Leu   Thr   Leu   Ser   Pro
                450                     455                     460

Tyr   Tyr   Lys   Val   Phe   Leu   Ala   Arg   Leu   Ile   Trp   Trp   Leu   Gln   Tyr   Phe
          465                     470                     475                     480
```

( 2 ) INFORMATION FOR SEQ ID NO:19:

( i ) SEQUENCE CHARACTERISTICS:
        ( A ) LENGTH: 144 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
          Lys   Val   Leu   Ile   Val   Ala   Leu   Leu   Phe   Ala   Gly   Val   Asp   Gly   Glu   Thr
          1                       5                       10                      15

Tyr   Thr   Ser   Gly   Gly   Ala   Ala   Ser   His   Thr   Thr   Ser   Thr   Leu   Ala   Ser
                            20                      25                      30

Leu   Phe   Ser   Pro   Gly   Ala   Ser   Gln   Arg   Ile   Gln   Leu   Val   Asn   Thr   Asn
                      35                      40                      45

Gly   Ser   Trp   His   Ile   Asn   Arg   Thr   Ala   Leu   Asn   Cys   Asn   Asp   Ser   Leu
                50                      55                      60

His   Thr   Gly   Phe   Leu   Ala   Ala   Leu   Phe   Tyr   Thr   His   Arg   Phe   Asn   Ser
          65                      70                      75                            80

Ser   Gly   Cys   Pro   Glu   Arg   Met   Ala   Ser   Cys   Arg   Pro   Ile   Asp   Trp   Phe
                            85                      90                      95

Ala   Gln   Gly   Trp   Gly   Pro   Ile   Thr   Tyr   Thr   Glu   Pro   Asp   Ser   Pro   Asp
                            100                     105                     110

Gln   Arg   Pro   Tyr   Cys   Trp   His   Tyr   Ala   Pro   Arg   Pro   Cys   Gly   Ile   Val
                      115                     120                     125

Pro   Ala   Ser   Gln   Val   Cys   Gly   Pro   Val   Tyr   Cys   Phe   Thr   Pro   Ser   Pro
                130                     135                     140
```

( 2 ) INFORMATION FOR SEQ ID NO:20:

( i ) SEQUENCE CHARACTERISTICS:
        ( A ) LENGTH: 144 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
          Lys   Val   Leu   Val   Val   Leu   Leu   Leu   Phe   Ala   Gly   Val   Asp   Ala   Glu   Thr
          1                       5                       10                      15

Ile   Val   Ser   Gly   Gly   Gln   Ala   Ala   Arg   Ala   Met   Ser   Gly   Leu   Val   Ser
                            20                      25                      30

Leu   Phe   Thr   Pro   Gly   Ala   Lys   Gln   Asn   Ile   Gln   Leu   Ile   Asn   Thr   Asn
                      35                      40                      45

Gly   Ser   Trp   His   Ile   Asn   Ser   Thr   Ala   Leu   Asn   Cys   Asn   Glu   Ser   Leu
                50                      55                      60

Asn   Thr   Gly   Trp   Leu   Ala   Gly   Leu   Ile   Tyr   Gln   His   Lys   Phe   Asn   Ser
          65                      70                      75                            80

Ser   Gly   Cys   Pro   Glu   Arg   Leu   Ala   Ser   Cys   Arg   Arg   Leu   Thr   Asp   Phe
                            85                      90                      95

Asp   Gln   Gly   Trp   Gly   Pro   Ile   Ser   His   Ala   Asn   Gly   Ser   Gly   Pro   Asp
                            100                     105                     110
```

```
Gln  Arg  Pro  Tyr  Cys  Trp  His  Tyr  Pro  Pro  Lys  Pro  Cys  Gly  Ile  Val
          115                      120                     125

Pro  Ala  Lys  Ser  Val  Cys  Gly  Pro  Val  Tyr  Cys  Phe  Thr  Pro  Ser  Pro
     130                      135                     140
```

( 2 ) INFORMATION FOR SEQ ID NO:21:

( i ) SEQUENCE CHARACTERISTICS:
        ( A ) LENGTH: 409 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Lys  Val  Leu  Val  Val  Leu  Leu  Leu  Phe  Ala  Gly  Val  Asp  Ala  Glu  Thr
1                   5                        10                      15

His  Val  Thr  Gly  Gly  Ser  Ala  Gly  Arg  Thr  Thr  Ala  Gly  Leu  Val  Gly
               20                      25                      30

Leu  Leu  Thr  Pro  Gly  Ala  Lys  Gln  Asn  Ile  Gln  Leu  Ile  Asn  Thr  Asn
               35                      40                      45

Gly  Ser  Trp  His  Ile  Asn  Ser  Thr  Ala  Leu  Asn  Cys  Asn  Glu  Ser  Leu
     50                      55                      60

Asn  Thr  Gly  Trp  Leu  Ala  Gly  Leu  Phe  Tyr  His  His  Lys  Phe  Asn  Ser
65                      70                      75                      80

Ser  Gly  Cys  Pro  Glu  Arg  Leu  Ala  Ser  Cys  Arg  Arg  Leu  Thr  Asp  Phe
               85                      90                      95

Ala  Gln  Gly  Trp  Gly  Pro  Ile  Ser  Tyr  Ala  Asn  Gly  Ser  Gly  Leu  Asp
               100                     105                     110

Glu  Arg  Pro  Tyr  Cys  Trp  His  Tyr  Pro  Pro  Arg  Pro  Cys  Gly  Ile  Val
          115                      120                     125

Pro  Ala  Lys  Ser  Val  Cys  Gly  Pro  Val  Tyr  Cys  Phe  Thr  Pro  Ser  Pro
     130                      135                     140

Val  Val  Val  Gly  Thr  Thr  Asp  Arg  Ser  Gly  Ala  Pro  Thr  Tyr  Ser  Trp
145                     150                     155                     160

Gly  Ala  Asn  Asp  Thr  Asp  Val  Phe  Val  Leu  Asn  Asn  Thr  Arg  Pro  Pro
               165                     170                     175

Leu  Gly  Asn  Trp  Phe  Gly  Cys  Thr  Trp  Met  Asn  Ser  Thr  Gly  Phe  Thr
               180                     185                     190

Lys  Val  Cys  Gly  Ala  Pro  Pro  Cys  Val  Ile  Gly  Gly  Val  Gly  Asn  Asn
          195                     200                     205

Thr  Leu  Leu  Cys  Pro  Thr  Asp  Cys  Phe  Arg  Lys  His  Pro  Glu  Ala  Thr
     210                     215                     220

Tyr  Ser  Arg  Cys  Gly  Ser  Gly  Pro  Trp  Ile  Thr  Pro  Arg  Cys  Met  Val
225                     230                     235                     240

Asp  Tyr  Pro  Tyr  Arg  Leu  Trp  His  Tyr  Pro  Cys  Thr  Ile  Asn  Tyr  Thr
               245                     250                     255

Ile  Phe  Lys  Val  Arg  Met  Tyr  Val  Gly  Gly  Val  Glu  His  Arg  Leu  Glu
               260                     265                     270

Ala  Ala  Cys  Asn  Trp  Thr  Arg  Gly  Glu  Arg  Cys  Asp  Leu  Glu  Asp  Arg
          275                     280                     285

Asp  Arg  Ser  Glu  Leu  Ser  Pro  Leu  Leu  Leu  Ser  Thr  Thr  Gln  Trp  Gln
     290                     295                     300

Val  Leu  Pro  Cys  Ser  Phe  Thr  Thr  Leu  Pro  Ala  Leu  Ser  Thr  Gly  Leu
305                     310                     315                     320

Ile  His  Leu  His  Gln  Asn  Ile  Val  Asp  Val  Gln  Tyr  Leu  Tyr  Gly  Val
```

325                           330                              335
Gly  Ser  Ser  Ile  Ala  Ser  Trp  Ala  Ile  Lys  Trp  Glu  Tyr  Val  Val  Leu
                    340                      345                350

Leu  Phe  Leu  Leu  Leu  Ala  Asp  Ala  Arg  Val  Cys  Ser  Cys  Leu  Trp  Met
          355                     360                     365

Met  Leu  Leu  Ile  Ser  Gln  Ala  Glu  Ala  Ala  Leu  Glu  Asn  Leu  Val  Ile
     370                      375                     380

Leu  Asn  Ala  Ala  Ser  Leu  Ala  Gly  Thr  His  Gly  Leu  Val  Ser  Phe  Leu
385                      390                     395                          400

Val  Phe  Phe  Cys  Phe  Ala  Trp  Tyr  Leu
                    405

( 2 ) INFORMATION FOR SEQ ID NO:22:

( i ) SEQUENCE CHARACTERISTICS:
      ( A ) LENGTH: 480 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:22:

Lys  Val  Leu  Ile  Val  Met  Leu  Leu  Phe  Ala  Gly  Val  Asp  Gly  Asp  Thr
1                   5                    10                          15

His  Val  Thr  Gly  Gly  Ala  Gln  Ala  Lys  Thr  Thr  Asn  Arg  Leu  Val  Ser
               20                   25                        30

Met  Phe  Ala  Ser  Gly  Pro  Ser  Gln  Lys  Ile  Gln  Leu  Ile  Asn  Thr  Asn
          35                   40                        45

Gly  Ser  Trp  His  Ile  Asn  Arg  Thr  Ala  Leu  Asn  Cys  Asn  Asp  Ser  Leu
     50                        55                   60

Gln  Thr  Gly  Phe  Leu  Ala  Ala  Leu  Phe  Tyr  Thr  His  Ser  Phe  Asn  Ser
65                       70                    75                          80

Ser  Gly  Cys  Pro  Glu  Arg  Met  Ala  Gln  Cys  Arg  Thr  Ile  Asp  Lys  Phe
                    85                   90                        95

Asp  Gln  Gly  Trp  Gly  Pro  Ile  Thr  Tyr  Ala  Glu  Ser  Ser  Arg  Ser  Asp
               100                      105                       110

Gln  Arg  Pro  Tyr  Cys  Trp  His  Tyr  Pro  Pro  Pro  Gln  Cys  Thr  Ile  Val
          115                      120                       125

Pro  Ala  Ser  Glu  Val  Cys  Gly  Pro  Val  Tyr  Cys  Phe  Thr  Pro  Ser  Pro
     130                      135                       140

Val  Val  Val  Gly  Thr  Thr  Asp  Arg  Phe  Gly  Val  Pro  Thr  Tyr  Arg  Trp
145                      150                       155                      160

Gly  Glu  Asn  Glu  Thr  Asp  Val  Leu  Leu  Leu  Asn  Asn  Thr  Arg  Pro  Pro
                    165                       170                  175

Gln  Gly  Asn  Trp  Phe  Gly  Cys  Thr  Trp  Met  Asn  Ser  Thr  Gly  Phe  Thr
               180                       185                 190

Lys  Thr  Cys  Gly  Gly  Pro  Pro  Cys  Asn  Ile  Gly  Gly  Val  Gly  Asn  Asn
          195                      200                       205

Thr  Leu  Thr  Cys  Pro  Thr  Asp  Cys  Phe  Arg  Lys  His  Pro  Glu  Ala  Thr
     210                      215                       220

Tyr  Thr  Lys  Cys  Gly  Ser  Gly  Pro  Trp  Leu  Thr  Pro  Arg  Cys  Met  Val
225                      230                       235                      240

Asp  Tyr  Pro  Tyr  Arg  Leu  Trp  His  Tyr  Pro  Cys  Thr  Val  Asn  Phe  Thr
                    245                       250                      255

Ile  Phe  Lys  Val  Arg  Met  Tyr  Val  Gly  Gly  Val  Glu  His  Arg  Leu  Asn
               260                       265                       270

```
Ala  Ala  Cys  Asn  Trp  Thr  Arg  Gly  Glu  Arg  Cys  Asp  Leu  Glu  Asp  Arg
          275                 280                      285

Asp  Arg  Pro  Glu  Leu  Ser  Pro  Leu  Leu  Leu  Ser  Thr  Thr  Glu  Trp  Gln
290                           295                      300

Val  Leu  Pro  Cys  Ser  Phe  Thr  Thr  Leu  Pro  Ala  Leu  Ser  Thr  Gly  Leu
305                           310                      315                      320

Ile  His  Leu  His  Gln  Asn  Ile  Val  Asp  Val  Gln  Tyr  Leu  Tyr  Gly  Ile
                    325                      330                      335

Gly  Ser  Ala  Val  Val  Ser  Phe  Ala  Ile  Lys  Trp  Glu  Tyr  Val  Leu  Leu
               340                      345                      350

Leu  Phe  Leu  Leu  Leu  Ala  Asp  Ala  Arg  Val  Cys  Ala  Cys  Leu  Trp  Met
          355                      360                 365

Met  Leu  Leu  Ile  Ala  Gln  Ala  Glu  Ala  Ala  Leu  Glu  Asn  Leu  Val  Val
     370                      375                      380

Leu  Asn  Ser  Ala  Ser  Val  Ala  Gly  Ala  His  Gly  Ile  Leu  Ser  Phe  Leu
385                      390                      395                      400

Val  Phe  Phe  Cys  Ala  Ala  Trp  Tyr  Ile  Lys  Gly  Arg  Leu  Val  Pro  Gly
               405                      410                      415

Ala  Thr  Tyr  Ala  Leu  Tyr  Gly  Val  Trp  Pro  Leu  Leu  Leu  Leu  Leu  Leu
               420                      425                      430

Ala  Leu  Pro  Pro  Arg  Ala  Tyr  Ala  Met  Asp  Arg  Glu  Met  Ala  Ala  Ser
          435                      440                      445

Cys  Gly  Gly  Ala  Val  Phe  Val  Gly  Leu  Val  Leu  Leu  Thr  Leu  Ser  Pro
     450                      455                      460

Tyr  Tyr  Lys  Val  Phe  Leu  Ala  Arg  Leu  Ile  Trp  Trp  Leu  Gln  Tyr  Phe
465                      470                      475                      480
```

(2) INFORMATION FOR SEQ ID NO:23:

(i) SEQUENCE CHARACTERISTICS:
        (A) LENGTH: 445 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Lys  Val  Leu  Val  Val  Leu  Leu  Leu  Phe  Ala  Gly  Val  Asp  Ala  Thr  Thr
1                   5                        10                      15

Tyr  Thr  Thr  Gly  Gly  Asn  Ala  Ala  Arg  Thr  Thr  Gln  Ala  Leu  Thr  Ser
               20                      25                      30

Phe  Phe  Ser  Pro  Gly  Ala  Lys  Gln  Asp  Ile  Gln  Leu  Ile  Asn  Thr  Asn
          35                      40                      45

Gly  Ser  Trp  His  Ile  Asn  Arg  Thr  Ala  Leu  Asn  Cys  Asn  Gly  Ser  Leu
     50                      55                      60

Asp  Thr  Gly  Trp  Val  Ala  Gly  Leu  Phe  Tyr  Tyr  His  Lys  Phe  Asn  Ser
65                       70                      75                      80

Ser  Gly  Cys  Pro  Glu  Arg  Met  Ala  Ser  Cys  Arg  Pro  Leu  Ala  Asp  Phe
               85                      90                      95

Gln  Gln  Gly  Trp  Gly  Pro  Ile  Ser  Tyr  Ala  Asn  Gly  Ser  Gly  Pro  Glu
               100                     105                     110

His  Arg  Pro  Tyr  Cys  Trp  His  Tyr  Pro  Pro  Lys  Pro  Cys  Gly  Ile  Val
          115                     120                     125

Pro  Ala  Gln  Asn  Val  Cys  Gly  Pro  Val  Tyr  Cys  Phe  Thr  Pro  Ser  Pro
130                     135                     140
```

```
Val  Val  Val  Gly  Thr  Thr  Asn  Lys  Leu  Gly  Ala  Pro  Thr  Tyr  Asn  Trp
145            150                      155                      160

Gly  Ser  Asn  Glu  Thr  Asp  Val  Phe  Val  Leu  Asn  Asn  Thr  Arg  Pro  Pro
               165                      170                      175

Leu  Gly  Asn  Trp  Phe  Gly  Cys  Thr  Trp  Met  Asn  Ser  Ser  Gly  Phe  Thr
               180                      185                 190

Lys  Val  Cys  Gly  Ala  Pro  Pro  Cys  Val  Ile  Gly  Gly  Val  Gly  Asn  Asn
          195                      200                      205

Thr  Leu  Gln  Cys  Pro  Thr  Asp  Cys  Phe  Arg  Lys  His  Pro  Asp  Ala  Thr
          210                      215                 220

Tyr  Ser  Arg  Cys  Ala  Ala  Gly  Pro  Trp  Ile  Thr  Pro  Arg  Cys  Leu  Val
225                      230                      235                      240

His  Tyr  Pro  Tyr  Arg  Leu  Trp  His  Tyr  Pro  Cys  Thr  Val  Asn  Tyr  Thr
                    245                      250                      255

Ile  Val  Gln  Ile  Arg  Met  Tyr  Val  Gly  Gly  Val  Asp  His  Arg  Leu  Glu
               260                      265                 270

Val  Ala  Cys  Asn  Trp  Thr  Arg  Gly  Glu  Arg  Cys  Asp  Leu  Asp  Asp  Arg
          275                      280                 285

Asp  Arg  Ser  Glu  Leu  Arg  Leu  Leu  Leu  Ser  Thr  Thr  Gln  Trp  Gln
290                      295                      300

Val  Leu  Pro  Cys  Ser  Phe  Thr  Thr  Leu  Pro  Ala  Leu  Thr  Thr  Gly  Leu
305                      310                      315                      320

Ile  His  Leu  His  Gln  Asn  Ile  Val  Asp  Val  Gln  Tyr  Leu  Tyr  Gly  Val
               325                      330                      335

Gly  Ser  Ser  Ile  Val  Ser  Trp  Ala  Ile  Lys  Trp  Glu  Tyr  Val  Ile  Leu
               340                      345                 350

Leu  Phe  Leu  Leu  Leu  Ala  Asn  Ala  Arg  Ile  Cys  Ser  Cys  Leu  Trp  Met
          355                      360                 365

Met  Leu  Leu  Ile  Ser  Gln  Ala  Glu  Ala  Ala  Leu  Glu  Asn  Leu  Val  Leu
          370                      375                 380

Leu  Asn  Ala  Ala  Ser  Leu  Ala  Gly  Ala  His  Ala  Val  Ala  Ser  Phe  Leu
385                      390                      395                      400

Val  Phe  Phe  Cys  Phe  Ala  Trp  Tyr  Leu  Lys  Gly  Arg  Trp  Val  Pro  Gly
                    405                      410                      415

Ala  Ala  Tyr  Ala  Phe  Tyr  Gly  Met  Trp  Pro  Leu  Leu  Leu  Leu  Leu  Leu
               420                      425                 430

Ala  Leu  Pro  Gln  Arg  Ala  Tyr  Ala  Leu  Asp  Thr  Glu  Met
          435                      440                 445
```

( 2 ) INFORMATION FOR SEQ ID NO:24:

( i ) SEQUENCE CHARACTERISTICS:
        ( A ) LENGTH: 409 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

```
Lys  Val  Leu  Val  Val  Leu  Leu  Leu  Phe  Ala  Gly  Val  Asp  Ala  Glu  Thr
1                   5                        10                      15

His  Val  Thr  Gly  Gly  Ser  Ala  Gly  Arg  Thr  Thr  Ala  Gly  Leu  Val  Gly
               20                      25                      30

Leu  Leu  Thr  Pro  Gly  Ala  Lys  Gln  Asn  Ile  Gln  Leu  Ile  Asn  Thr  Asn
               35                      40                      45

Gly  Ser  Trp  His  Ile  Asn  Ser  Thr  Ala  Leu  Asn  Cys  Asn  Glu  Ser  Leu
```

```
              50                      55                      60
    Asn  Thr  Gly  Trp  Leu  Ala  Gly  Leu  Phe  Tyr  His  His  Lys  Phe  Asn  Ser
    65                      70                      75                      80

Ser  Gly  Cys  Pro  Glu  Arg  Leu  Ala  Ser  Cys  Arg  Arg  Leu  Thr  Asp  Phe
                        85                      90                      95

Ala  Gln  Gly  Trp  Gly  Pro  Ile  Ser  Tyr  Ala  Asn  Gly  Ser  Gly  Leu  Asp
                   100                     105                     110

Glu  Arg  Pro  Tyr  Cys  Trp  His  Tyr  Pro  Pro  Arg  Pro  Cys  Gly  Ile  Val
              115                     120                     125

Pro  Ala  Lys  Ser  Val  Cys  Gly  Pro  Val  Tyr  Cys  Phe  Thr  Pro  Ser  Pro
         130                     135                     140

Val  Val  Val  Gly  Thr  Thr  Asp  Arg  Ser  Gly  Ala  Pro  Thr  Tyr  Ser  Trp
    145                     150                     155                     160

Gly  Ala  Asn  Asp  Thr  Asp  Val  Phe  Val  Leu  Asn  Asn  Thr  Arg  Pro  Pro
                        165                     170                     175

Leu  Gly  Asn  Trp  Phe  Gly  Cys  Thr  Trp  Met  Asn  Ser  Thr  Gly  Phe  Thr
                   180                     185                     190

Lys  Val  Cys  Gly  Ala  Pro  Pro  Cys  Val  Ile  Gly  Gly  Val  Gly  Asn  Asn
              195                     200                     205

Thr  Leu  Leu  Cys  Pro  Thr  Asp  Cys  Phe  Arg  Lys  His  Pro  Glu  Ala  Thr
         210                     215                     220

Tyr  Ser  Arg  Cys  Gly  Ser  Gly  Pro  Trp  Ile  Thr  Pro  Arg  Cys  Met  Val
    225                     230                     235                     240

Asp  Tyr  Pro  Tyr  Arg  Leu  Trp  His  Tyr  Pro  Cys  Thr  Ile  Asn  Tyr  Thr
                        245                     250                     255

Ile  Phe  Lys  Val  Arg  Met  Tyr  Val  Gly  Gly  Val  Glu  His  Arg  Leu  Glu
                   260                     265                     270

Ala  Ala  Cys  Asn  Trp  Thr  Arg  Gly  Glu  Arg  Cys  Asp  Leu  Glu  Asp  Arg
              275                     280                     285

Asp  Arg  Ser  Glu  Leu  Ser  Pro  Leu  Leu  Leu  Ser  Thr  Thr  Gln  Trp  Gln
         290                     295                     300

Val  Leu  Pro  Cys  Ser  Phe  Thr  Thr  Leu  Pro  Ala  Leu  Ser  Thr  Gly  Leu
    305                     310                     315                     320

Ile  His  Leu  His  Gln  Asn  Ile  Val  Asp  Val  Gln  Tyr  Leu  Tyr  Gly  Val
                        325                     330                     335

Gly  Ser  Ser  Ile  Ala  Ser  Trp  Ala  Ile  Lys  Trp  Glu  Tyr  Val  Val  Leu
                   340                     345                     350

Leu  Phe  Leu  Leu  Leu  Ala  Asp  Ala  Arg  Val  Cys  Ser  Cys  Leu  Trp  Met
              355                     360                     365

Met  Leu  Leu  Ile  Ser  Gln  Ala  Glu  Ala  Ala  Leu  Glu  Asn  Leu  Val  Ile
         370                     375                     380

Leu  Asn  Ala  Ala  Ser  Leu  Ala  Gly  Thr  His  Gly  Leu  Val  Ser  Phe  Leu
    385                     390                     395                     400

Val  Phe  Phe  Cys  Phe  Ala  Trp  Tyr  Leu
                        405
```

( 2 ) INFORMATION FOR SEQ ID NO:25:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Glu  Thr  Tyr  Val  Ser  Gly  Gly  Ser  Ala  Ala  Gln  Thr  Thr  Ala  Gly  Phe
  1              5                        10                        15

Val  Arg  Leu  Phe  Glu  Thr  Gly  Pro  Lys  Gln  Asn  Ile  Gln  Leu  Ile
               20                       25                      30
```

( 2 ) INFORMATION FOR SEQ ID NO:26:

( i ) SEQUENCE CHARACTERISTICS:
        ( A ) LENGTH: 88 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

```
Trp  Met  Asn  Ser  Thr  Gly  Phe  Thr  Glu  Val  Cys  Gly  Ala  Pro  Pro  Cys
  1              5                        10                       15

Val  Ile  Gly  Gly  Ala  Gly  Asn  Asn  Thr  Leu  His  Cys  Pro  Thr  Asp  Cys
               20                       25                       30

Phe  Arg  Lys  His  Pro  Asp  Ala  Thr  Tyr  Ser  Arg  Cys  Gly  Ser  Gly  Pro
               35                       40                       45

Trp  Ile  Thr  Pro  Arg  Cys  Leu  Val  Asp  Tyr  Pro  Tyr  Arg  Leu  Trp  His
          50                       55                      60

Tyr  Pro  Cys  Thr  Ile  Asn  Tyr  Thr  Ile  Phe  Lys  Ile  Arg  Met  Tyr  Val
 65                           70                      75                      80

Gly  Gly  Val  Glu  His  Arg  Leu  Glu
                    85
```

( 2 ) INFORMATION FOR SEQ ID NO:27:

( i ) SEQUENCE CHARACTERISTICS:
        ( A ) LENGTH: 88 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

```
Trp  Met  Asn  Ser  Thr  Gly  Phe  Thr  Lys  Val  Cys  Gly  Ala  Pro  Pro  Cys
  1              5                        10                       15

Val  Ile  Gly  Gly  Ala  Gly  Asn  Asn  Thr  Leu  His  Cys  Pro  Thr  Asp  Cys
               20                       25                       30

Phe  Arg  Lys  His  Pro  Asp  Ala  Thr  Tyr  Ser  Arg  Cys  Gly  Ser  Gly  Pro
               35                       40                       45

Trp  Ile  Thr  Pro  Arg  Cys  Leu  Val  Asp  Tyr  Pro  Tyr  Arg  Leu  Trp  His
          50                       55                      60

Tyr  Pro  Cys  Thr  Ile  Asn  Tyr  Thr  Ile  Phe  Lys  Ile  Arg  Met  Tyr  Val
 65                           70                      75                      80

Gly  Gly  Val  Glu  His  Arg  Leu  Glu
                    85
```

( 2 ) INFORMATION FOR SEQ ID NO:28:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

| Glu | Thr | Tyr | Val | Ser | Gly | Gly | Ala | Ala | Ala | Gln | Thr | Thr | Ala | Arg | Phe |
| 1 | | | | 5 | | | | | 10 | | | | | 15 | |

| Ala | Gly | Phe | Phe | Gln | Ser | Gly | Ala | Lys | Gln | Asn | Ile | Gln | Leu | Ile |
| | | | 20 | | | | | 25 | | | | | 30 | |

( 2 ) INFORMATION FOR SEQ ID NO:29:

( i ) SEQUENCE CHARACTERISTICS:
       ( A ) LENGTH: 268 amino acids
       ( B ) TYPE: amino acid
       ( C ) STRANDEDNESS: single
       ( D ) TOPOLOGY: linear ( i i ) MOLECULE TYPE: protein ( i x ) FEATURE:
       ( A ) NAME/KEY: Duplication
       ( B ) LOCATION: 3
       ( D ) OTHER INFORMATION: /label=heterogeneity
             / note= "Amino acid #3 can also be Arg."

( i x ) FEATURE:
       ( A ) NAME/KEY: Duplication
       ( B ) LOCATION: 7
       ( D ) OTHER INFORMATION: /label=Heterogeneity
             / note= "Amino Acid #5 can also be Ala."

( x i ) SEQUENCE DESCRIPTION: SEQ ID NO:29:

| Asn | Thr | His | Val | Thr | Gly | Ala | Val | Gln | Gly | His | Gly | Ala | Phe | Gly | Leu |
| 1 | | | | 5 | | | | | 10 | | | | | 15 | |

| Thr | Ser | Leu | Phe | Gln | Pro | Gly | Ala | Ser | Gln | Lys | Ile | Gln | Leu | Val | Asn |
| | | | 20 | | | | | 25 | | | | | 30 | | |

| Thr | Asn | Gly | Ser | Trp | His | Ile | Asn | Arg | Thr | Ala | Leu | Asn | Cys | Asn | Asp |
| | | 35 | | | | | 40 | | | | | 45 | | | |

| Ser | Leu | Lys | Thr | Gly | Phe | Leu | Ala | Ala | Leu | Phe | Tyr | Thr | His | Arg | Phe |
| | 50 | | | | | 55 | | | | | 60 | | | | |

| Asn | Ala | Ser | Gly | Cys | Pro | Glu | Arg | Met | Ala | Ser | Cys | Arg | Ser | Ile | Asp |
| 65 | | | | 70 | | | | | 75 | | | | | 80 | |

| Lys | Phe | Asp | Gln | Gly | Trp | Gly | Pro | Ile | Thr | Tyr | Ala | Gln | Pro | Asp | Asn |
| | | | 85 | | | | | 90 | | | | | 95 | | |

| Ser | Asp | Gln | Arg | Pro | Tyr | Cys | Trp | His | Tyr | Thr | Pro | Arg | Gln | Cys | Gly |
| | | | 100 | | | | | 105 | | | | | 110 | | |

| Ile | Val | Pro | Ala | Ser | Gln | Val | Cys | Gly | Pro | Val | Tyr | Cys | Phe | Thr | Pro |
| | | 115 | | | | | 120 | | | | | 125 | | | |

| Ser | Pro | Val | Val | Val | Gly | Thr | Thr | Asp | Arg | Ser | Gly | Ala | Pro | Thr | Tyr |
| | 130 | | | | | 135 | | | | | 140 | | | | |

| Asn | Trp | Gly | Asp | Asn | Glu | Thr | Asp | Val | Leu | Leu | Leu | Asn | Asn | Thr | Arg |
| 145 | | | | | 150 | | | | | 155 | | | | | 160 |

| Pro | Pro | His | Gly | Asn | Trp | Phe | Gly | Cys | Thr | Trp | Met | Asn | Ser | Thr | Gly |
| | | | | 165 | | | | | 170 | | | | | 175 | |

| Phe | Thr | Lys | Thr | Cys | Gly | Gly | Pro | Pro | Cys | Asn | Ile | Gly | Gly | Val | Gly |
| | | | 180 | | | | | 185 | | | | | 190 | | |

| Asn | Asn | Thr | Leu | Thr | Cys | Pro | Thr | Asp | Cys | Phe | Arg | Lys | His | Pro | Asp |
| | | | 195 | | | | 200 | | | | | 205 | | | |

| Ala | Thr | Tyr | Thr | Lys | Cys | Gly | Ser | Gly | Pro | Trp | Leu | Thr | Pro | Arg | Cys |
| | 210 | | | | | 215 | | | | | 220 | | | | |

| Leu | Val | Asp | Tyr | Pro | Tyr | Arg | Leu | Trp | His | Tyr | Pro | Cys | Thr | Val | Asn |
| 225 | | | | | 230 | | | | | 235 | | | | | 240 |

| Phe | Thr | Ile | Phe | Lys | Val | Arg | Met | Tyr | Val | Gly | Gly | Val | Glu | His | Arg |
| | | | | 245 | | | | | 250 | | | | | 255 | |

Leu Asp Ala Ala Cys Asn Trp Thr Arg Gly Glu Arg
              260                      265

( 2 ) INFORMATION FOR SEQ ID NO:30:

( i ) SEQUENCE CHARACTERISTICS:
        ( A ) LENGTH: 268 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Duplication
        ( B ) LOCATION: 5
        ( D ) OTHER INFORMATION: /label=Heterogeneity
            / note= "This amino acid can also be Met."

( i x ) FEATURE:
        ( A ) NAME/KEY: Duplication
        ( B ) LOCATION: 79
        ( D ) OTHER INFORMATION: /label=Heterogeneity
            / note= "This amino acid can also be Val."

( i x ) FEATURE:
        ( A ) NAME/KEY: Duplication
        ( B ) LOCATION: 80
        ( D ) OTHER INFORMATION: /label=Heterogeneity
            / note= "This amino acid can also be Gly."

( i x ) FEATURE:
        ( A ) NAME/KEY: Duplication
        ( B ) LOCATION: 93
        ( D ) OTHER INFORMATION: /label=Heterogeneity
            / note= "This amino acid can also be Gln."

( i x ) FEATURE:
        ( A ) NAME/KEY: Duplication
        ( B ) LOCATION: 139
        ( D ) OTHER INFORMATION: /label=Heterogeneity
            / note= "This amino acid can only be Phe."

( i x ) FEATURE:
        ( A ) NAME/KEY: Duplication
        ( B ) LOCATION: 141
        ( D ) OTHER INFORMATION: /label=Heterogeneity
            / note= "This amino acid can also be Val."

( i x ) FEATURE:
        ( A ) NAME/KEY: Duplication
        ( B ) LOCATION: 191
        ( D ) OTHER INFORMATION: /label=Heterogeneity
            / note= "This amino acid can also be Ala."

( i x ) FEATURE:
        ( A ) NAME/KEY: Duplication
        ( B ) LOCATION: 197
        ( D ) OTHER INFORMATION: /label=Heterogeneity
            / note= "This amino acid can also be Thr."

( i x ) FEATURE:
        ( A ) NAME/KEY: Duplication
        ( B ) LOCATION: 208
        ( D ) OTHER INFORMATION: /label=Heterogeneity
            / note= "This amino acid can also be Arg and Asp."

( i x ) FEATURE:
        ( A ) NAME/KEY: Duplication
        ( B ) LOCATION: 233
        ( D ) OTHER INFORMATION: /label=Heterogeneity
            / note= "This amino acid can also be Trp."

( i x ) FEATURE:
        ( A ) NAME/KEY: Duplication
        ( B ) LOCATION: 247
        ( D ) OTHER INFORMATION: /label=Heterogeneity
            / note= "This amino acid can also be Lys."

(ix) FEATURE:
   (A) NAME/KEY: Duplication
   (B) LOCATION: 251
   (D) OTHER INFORMATION: /label=Heterogeneity
        / note= "This amino acid can also be Gly."

(xi) SEQUENCE DESCRIPTION: SEQ ID NO:30:

| His | Thr | Arg | Val | Met | Gly | Gly | Val | Gln | Gly | His | Val | Thr | Ser | Thr | Leu |
|---|---|---|---|---|---|---|---|---|---|---|---|---|---|---|---|
| 1 | | | | 5 | | | | | 10 | | | | | 15 | |
| Thr | Ser | Leu | Phe | Arg | Pro | Gly | Ala | Ser | Gln | Lys | Ile | Gln | Leu | Val | Asn |
| | | | 20 | | | | | 25 | | | | | 30 | | |
| Thr | Asn | Gly | Ser | Trp | His | Ile | Asn | Arg | Thr | Ala | Leu | Asn | Cys | Asn | Asp |
| | | 35 | | | | | 40 | | | | | 45 | | | |
| Ser | Leu | Gln | Thr | Gly | Phe | Leu | Ala | Ala | Leu | Phe | Tyr | Thr | His | Lys | Phe |
| | 50 | | | | | 55 | | | | | 60 | | | | |
| Asn | Ala | Ser | Gly | Cys | Pro | Glu | Arg | Met | Ala | Ser | Cys | Arg | Ser | Ile | Asp |
| 65 | | | | | 70 | | | | | 75 | | | | | 80 |
| Lys | Phe | Asp | Gln | Gly | Trp | Gly | Pro | Ile | Thr | Tyr | Ala | Arg | Pro | Asp | Asn |
| | | | | 85 | | | | | 90 | | | | | 95 | |
| Ser | Asp | Gln | Arg | Pro | Tyr | Cys | Trp | His | Tyr | Ala | Pro | Arg | Gln | Cys | Gly |
| | | | 100 | | | | | 105 | | | | | 110 | | |
| Ile | Val | Pro | Ala | Ser | Gln | Val | Cys | Gly | Pro | Val | Tyr | Cys | Phe | Thr | Pro |
| | | 115 | | | | | 120 | | | | | 125 | | | |
| Ser | Pro | Val | Val | Val | Gly | Thr | Thr | Asp | Arg | Ser | Gly | Ala | Pro | Thr | Tyr |
| | 130 | | | | | 135 | | | | | 140 | | | | |
| Asn | Trp | Gly | Asp | Asn | Glu | Thr | Asp | Val | Leu | Leu | Leu | Asn | Asn | Thr | Arg |
| 145 | | | | | 150 | | | | | 155 | | | | | 160 |
| Pro | Pro | His | Gly | Asn | Trp | Phe | Gly | Cys | Thr | Trp | Met | Asn | Ser | Thr | Gly |
| | | | | 165 | | | | | 170 | | | | | 175 | |
| Phe | Thr | Lys | Thr | Cys | Gly | Gly | Pro | Pro | Cys | Asn | Ile | Gly | Gly | Val | Gly |
| | | | 180 | | | | | 185 | | | | | 190 | | |
| Asn | Asn | Thr | Leu | Ile | Cys | Pro | Thr | Asp | Cys | Phe | Arg | Lys | His | Pro | Glu |
| | | 195 | | | | | 200 | | | | | 205 | | | |
| Ala | Thr | Tyr | Thr | Lys | Cys | Gly | Ser | Gly | Pro | Trp | Leu | Thr | Pro | Arg | Cys |
| | 210 | | | | | 215 | | | | | 220 | | | | |
| Leu | Val | Asp | Tyr | Pro | Tyr | Arg | Leu | Arg | His | Tyr | Pro | Cys | Thr | Val | Asn |
| 225 | | | | | 230 | | | | | 235 | | | | | 240 |
| Phe | Thr | Ile | Phe | Lys | Val | Arg | Met | Tyr | Val | Glu | Gly | Val | Glu | His | Arg |
| | | | | 245 | | | | | 250 | | | | | 255 | |
| Leu | Asp | Ala | Ala | Cys | Asn | Trp | Thr | Arg | Gly | Glu | Arg |
| | | | | 260 | | | | | 265 | | |

(2) INFORMATION FOR SEQ ID NO:31:

(i) SEQUENCE CHARACTERISTICS:
   (A) LENGTH: 353 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:31:

| Glu | Thr | Tyr | Thr | Thr | Gly | Gly | Ser | Thr | Ala | Arg | Thr | Thr | Gln | Gly | Leu |
|---|---|---|---|---|---|---|---|---|---|---|---|---|---|---|---|
| 1 | | | | 5 | | | | | 10 | | | | | 15 | |
| Val | Ser | Leu | Phe | Ser | Arg | Gly | Ala | Lys | Gln | Asp | Ile | Gln | Leu | Ile | Asn |
| | | | 20 | | | | | 25 | | | | | 30 | | |
| Thr | Asn | Gly | Ser | Trp | His | Ile | Asn | Arg | Thr | Ala | Leu | Asn | Cys | Asn | Glu |

|  |  |  | 35 |  |  |  | 40 |  |  |  | 45 |  |  |  |
|---|---|---|---|---|---|---|---|---|---|---|---|---|---|---|
| Ser | Leu | Asp | Thr | Gly | Trp | Val | Ala | Gly | Leu | Phe | Tyr | Tyr | His | Lys | Phe |
|  |  | 50 |  |  |  | 55 |  |  |  | 60 |  |  |  |  |
| Asn | Ser | Ser | Gly | Cys | Pro | Glu | Arg | Met | Ala | Ser | Cys | Arg | Pro | Leu | Ala |
| 65 |  |  |  | 70 |  |  |  | 75 |  |  |  |  |  | 80 |  |
| Asp | Phe | Asp | Gln | Gly | Trp | Gly | Pro | Ile | Ser | Tyr | Ala | Asn | Gly | Thr | Gly |
|  |  |  |  | 85 |  |  |  |  | 90 |  |  |  |  | 95 |  |
| Pro | Glu | His | Arg | Pro | Tyr | Cys | Trp | His | Tyr | Pro | Pro | Lys | Pro | Cys | Gly |
|  |  |  | 100 |  |  |  |  | 105 |  |  |  |  | 110 |  |  |
| Ile | Val | Pro | Ala | Gln | Thr | Val | Cys | Gly | Pro | Val | Tyr | Cys | Phe | Thr | Pro |
|  |  |  | 115 |  |  |  | 120 |  |  |  |  | 125 |  |  |  |
| Ser | Pro | Val | Val | Val | Gly | Thr | Thr | Asn | Lys | Leu | Gly | Ala | Pro | Thr | Tyr |
|  | 130 |  |  |  |  | 135 |  |  |  |  | 140 |  |  |  |  |
| Asn | Trp | Gly | Cys | Asn | Asp | Thr | Asp | Val | Phe | Val | Leu | Asn | Asn | Thr | Arg |
| 145 |  |  |  |  | 150 |  |  |  |  | 155 |  |  |  |  | 160 |
| Pro | Pro | Leu | Gly | Asn | Trp | Phe | Gly | Cys | Thr | Trp | Val | Asn | Ser | Ser | Gly |
|  |  |  |  | 165 |  |  |  |  | 170 |  |  |  | 175 |  |  |
| Phe | Thr | Lys | Val | Cys | Gly | Ala | Pro | Pro | Cys | Val | Ile | Gly | Gly | Ala | Gly |
|  |  |  | 180 |  |  |  |  | 185 |  |  |  |  | 190 |  |  |
| Asn | Asn | Thr | Leu | Tyr | Cys | Pro | Thr | Asp | Cys | Phe | Arg | Lys | His | Pro | Glu |
|  |  | 195 |  |  |  |  | 200 |  |  |  |  | 205 |  |  |  |
| Ala | Thr | Tyr | Ser | Arg | Cys | Gly | Ser | Gly | Pro | Trp | Ile | Thr | Pro | Arg | Cys |
|  | 210 |  |  |  |  | 215 |  |  |  |  | 220 |  |  |  |  |
| Leu | Val | Gly | Tyr | Pro | Tyr | Arg | Leu | Trp | His | Tyr | Pro | Cys | Thr | Val | Asn |
| 225 |  |  |  |  | 230 |  |  |  |  | 235 |  |  |  |  | 240 |
| Tyr | Thr | Leu | Phe | Lys | Val | Arg | Met | Tyr | Val | Gly | Gly | Val | Glu | His | Arg |
|  |  |  |  | 245 |  |  |  |  | 250 |  |  |  |  | 255 |  |
| Leu | Gln | Val | Ala | Cys | Asn | Trp | Thr | Arg | Gly | Glu | Arg | Cys | Asn | Leu | Asp |
|  |  |  | 260 |  |  |  |  | 265 |  |  |  |  | 270 |  |  |
| Asp | Arg | Asp | Arg | Ser | Glu | Leu | Ser | Pro | Leu | Leu | Leu | Ser | Thr | Thr | Gln |
|  |  | 275 |  |  |  |  | 280 |  |  |  |  | 285 |  |  |  |
| Trp | Gln | Val | Leu | Pro | Cys | Ser | Phe | Thr | Thr | Leu | Pro | Ala | Leu | Thr | Thr |
|  | 290 |  |  |  |  | 295 |  |  |  |  | 300 |  |  |  |  |
| Gly | Leu | Ile | His | Leu | His | Gln | Asn | Ile | Val | Asp | Val | Gln | Tyr | Leu | Tyr |
| 305 |  |  |  |  | 310 |  |  |  |  | 315 |  |  |  |  | 320 |
| Gly | Val | Gly | Ser | Ser | Ile | Val | Ser | Trp | Ala | Ile | Lys | Trp | Glu | Tyr | Val |
|  |  |  |  | 325 |  |  |  |  | 330 |  |  |  |  | 335 |  |
| Ile | Leu | Leu | Phe | Leu | Leu | Leu | Ala | Asp | Ala | Arg | Val | Cys | Ser | Cys | Leu |
|  |  |  | 340 |  |  |  |  | 345 |  |  |  |  | 350 |  |  |
| Trp |  |  |  |  |  |  |  |  |  |  |  |  |  |  |  |

( 2 ) INFORMATION FOR SEQ ID NO:32:

( i ) SEQUENCE CHARACTERISTICS:
        ( A ) LENGTH: 353 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

| Thr | Thr | Tyr | Thr | Thr | Gly | Gly | Asn | Ala | Ala | Arg | Thr | Thr | Gln | Ala | Leu |
|---|---|---|---|---|---|---|---|---|---|---|---|---|---|---|---|
| 1 |  |  |  | 5 |  |  |  |  | 10 |  |  |  |  | 15 |  |
| Thr | Ser | Phe | Phe | Ser | Pro | Gly | Ala | Lys | Gln | Asp | Ile | Gln | Leu | Ile | Asn |
|  |  |  | 20 |  |  |  |  | 25 |  |  |  |  | 30 |  |  |

```
Thr  Asn  Gly  Ser  Trp  His  Ile  Asn  Arg  Thr  Ala  Leu  Asn  Cys  Asn  Gly
          35                  40                       45

Ser  Leu  Asp  Thr  Gly  Trp  Val  Ala  Gly  Leu  Phe  Tyr  Tyr  His  Lys  Phe
          50                  55                       60

Asn  Ser  Ser  Gly  Cys  Pro  Glu  Arg  Met  Ala  Ser  Cys  Arg  Pro  Leu  Ala
65                       70                  75                            80

Asp  Phe  Gln  Gln  Gly  Trp  Gly  Pro  Ile  Ser  Tyr  Ala  Asn  Gly  Ser  Gly
                    85                       90                       95

Pro  Glu  His  Arg  Pro  Tyr  Cys  Trp  His  Tyr  Pro  Pro  Lys  Pro  Cys  Gly
               100                      105                 110

Ile  Val  Pro  Ala  Gln  Asn  Val  Cys  Gly  Pro  Val  Tyr  Cys  Phe  Thr  Pro
               115                 120                      125

Ser  Pro  Val  Val  Val  Gly  Thr  Thr  Asn  Lys  Leu  Gly  Ala  Pro  Thr  Tyr
     130                      135                      140

Asn  Trp  Gly  Ser  Asn  Glu  Thr  Asp  Val  Phe  Val  Leu  Asn  Asn  Thr  Arg
145                      150                      155                      160

Pro  Pro  Leu  Gly  Asn  Trp  Phe  Gly  Cys  Thr  Trp  Met  Asn  Ser  Ser  Gly
                    165                      170                      175

Phe  Thr  Lys  Val  Cys  Gly  Ala  Pro  Pro  Cys  Val  Ile  Gly  Gly  Val  Gly
               180                      185                      190

Asn  Asn  Thr  Leu  Gln  Cys  Pro  Thr  Asp  Cys  Phe  Arg  Lys  His  Pro  Asp
               195                      200                      205

Ala  Thr  Tyr  Ser  Arg  Cys  Ala  Ala  Gly  Pro  Trp  Ile  Thr  Pro  Arg  Cys
     210                      215                      220

Leu  Val  His  Tyr  Pro  Tyr  Arg  Leu  Trp  His  Tyr  Pro  Cys  Thr  Val  Asn
225                      230                      235                      240

Tyr  Thr  Ile  Val  Gln  Ile  Arg  Met  Tyr  Val  Gly  Gly  Val  Asp  His  Arg
                    245                      250                      255

Leu  Glu  Val  Ala  Cys  Asn  Trp  Thr  Arg  Gly  Glu  Arg  Cys  Asp  Leu  Asp
               260                      265                      270

Asp  Arg  Asp  Arg  Ser  Glu  Leu  Arg  Leu  Leu  Leu  Ser  Thr  Thr  Gln
          275                      280                      285

Trp  Gln  Val  Leu  Pro  Cys  Ser  Phe  Thr  Thr  Leu  Pro  Ala  Leu  Thr  Thr
     290                      295                      300

Gly  Leu  Ile  His  Leu  His  Gln  Asn  Ile  Val  Asp  Val  Gln  Tyr  Leu  Tyr
305                      310                      315                      320

Gly  Val  Gly  Ser  Ser  Ile  Val  Ser  Trp  Ala  Ile  Lys  Trp  Glu  Tyr  Val
                    325                      330                      335

Ile  Leu  Leu  Phe  Leu  Leu  Leu  Ala  Asn  Ala  Arg  Ile  Cys  Ser  Cys  Leu
               340                      345                      350

Trp
```

(2) INFORMATION FOR SEQ ID NO:33:

(i) SEQUENCE CHARACTERISTICS:
　　　　(A) LENGTH: 32 amino acids
　　　　(B) TYPE: amino acid
　　　　(C) STRANDEDNESS: single
　　　　(D) TOPOLOGY: linear (ii) MOLECULE TYPE: protein (xi) SEQUENCE DESCRIPTION: SEQ ID NO:33:

```
Glu  Thr  Tyr  Thr  Ser  Gly  Gly  Asn  Ala  Gly  His  Thr  Met  Thr  Gly  Ile
1                        5                        10                       15

Val  Arg  Phe  Phe  Ala  Pro  Gly  Pro  Lys  Gln  Asn  Val  His  Leu  Ile  Asn
               20                       25                       30
```

( 2 ) INFORMATION FOR SEQ ID NO:34:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Glu  Thr  Thr  Val  Thr  Gly  Gly  Ser  Ala  Ala  His  Gly  Ala  Leu  Gly  Ile
 1                   5                        10                      15

Ala  Ser  Leu  Phe  Asn  Cys  Gly  Ala  Arg  Cys  Asn  Ile  Cys  Leu  Ile  Asn
               20                        25                      30

Thr
```

( 2 ) INFORMATION FOR SEQ ID NO:35:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

```
His  Thr  Arg  Val  Thr  Gly  Gly  Val  Gln  Gly  His  Val  Thr  Ser  Thr  Leu
 1                   5                        10                      15

Thr  Ser  Leu  Phe  Arg  Pro  Gly  Ala  Ser  Gln  Lys  Ile  Gln  Leu  Val  Asn
               20                        25                      30
```

( 2 ) INFORMATION FOR SEQ ID NO:36:

( i ) SEQUENCE CHARACTERISTICS:
        ( A ) LENGTH: 3011 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Met  Ser  Thr  Asn  Pro  Lys  Pro  Gln  Lys  Lys  Asn  Lys  Arg  Asn  Thr  Asn
 1                   5                        10                      15

Arg  Arg  Pro  Gln  Asp  Val  Lys  Phe  Pro  Gly  Gly  Gly  Gln  Ile  Val  Gly
               20                        25                      30

Gly  Val  Tyr  Leu  Leu  Pro  Arg  Arg  Gly  Pro  Arg  Leu  Gly  Val  Arg  Ala
               35                        40                      45

Thr  Arg  Lys  Thr  Ser  Glu  Arg  Ser  Gln  Pro  Arg  Gly  Arg  Arg  Gln  Pro
      50                        55                      60

Ile  Pro  Lys  Ala  Arg  Arg  Pro  Glu  Gly  Arg  Thr  Trp  Ala  Gln  Pro  Gly
 65                       70                       75                      80

Tyr  Pro  Trp  Pro  Leu  Tyr  Gly  Asn  Glu  Gly  Cys  Gly  Trp  Ala  Gly  Trp
               85                        90                      95

Leu  Leu  Ser  Pro  Arg  Gly  Ser  Arg  Pro  Ser  Trp  Gly  Pro  Thr  Asp  Pro
              100                       105                     110

Arg  Arg  Arg  Ser  Arg  Asn  Leu  Gly  Lys  Val  Ile  Asp  Thr  Leu  Thr  Cys
              115                       120                     125

Gly  Phe  Ala  Asp  Leu  Met  Gly  Tyr  Ile  Pro  Leu  Val  Gly  Ala  Pro  Leu
              130                       135                     140
```

```
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
```

-continued

|   |   |   |   |   |   |   |   |   |   |   |   |   |   |   |
|---|---|---|---|---|---|---|---|---|---|---|---|---|---|---|
|   |   |   |   | 565 |   |   |   | 570 |   |   |   | 575 |   |   |
| Asn | Thr | Leu | His 580 | Cys | Pro | Thr | Asp 585 | Cys | Phe | Arg | Lys | His 590 | Pro | Asp | Ala |
| Thr | Tyr | Ser | Arg 595 | Cys | Gly | Ser | Gly 600 | Pro | Trp | Ile | Thr | Pro 605 | Arg | Cys | Leu |
| Val | Asp 610 | Tyr | Pro | Tyr | Arg | Leu 615 | Trp | His | Tyr | Pro | Cys 620 | Thr | Ile | Asn | Tyr |
| Thr 625 | Ile | Phe | Lys | Ile | Arg 630 | Met | Tyr | Val | Gly | Gly 635 | Val | Glu | His | Arg | Leu 640 |
| Glu | Ala | Ala | Cys | Asn 645 | Trp | Thr | Arg | Gly | Glu 650 | Arg | Cys | Asp | Leu | Glu 655 | Asp |
| Arg | Asp | Arg | Ser 660 | Glu | Leu | Ser | Pro 665 | Leu | Leu | Thr | Thr | Thr 670 | Gln | Trp |
| Gln | Val | Leu 675 | Pro | Cys | Ser | Phe | Thr 680 | Thr | Leu | Pro | Ala | Leu 685 | Ser | Thr | Gly |
| Leu | Ile | His 690 | Leu | His | Gln | Asn 695 | Ile | Val | Asp | Val | Gln 700 | Tyr | Leu | Tyr | Gly |
| Val 705 | Gly | Ser | Ser | Ile | Ala 710 | Ser | Trp | Ala | Ile | Lys 715 | Trp | Glu | Tyr | Val | Val 720 |
| Leu | Leu | Phe | Leu | Leu 725 | Leu | Ala | Asp | Ala | Arg 730 | Val | Cys | Ser | Cys | Leu 735 | Trp |
| Met | Met | Leu | Leu 740 | Ile | Ser | Gln | Ala | Glu 745 | Ala | Ala | Leu | Glu | Asn 750 | Leu | Val |
| Ile | Leu | Asn | Ala | Ala 755 | Ser | Leu | Ala | Gly 760 | Thr | His | Gly | Leu 765 | Val | Ser | Phe |
| Leu | Val 770 | Phe | Phe | Cys | Phe | Ala 775 | Trp | Tyr | Leu | Lys | Gly 780 | Lys | Trp | Val | Pro |
| Gly 785 | Ala | Val | Tyr | Thr | Phe 790 | Tyr | Gly | Met | Trp | Pro 795 | Leu | Leu | Leu | Leu | Leu 800 |
| Leu | Ala | Leu | Pro | Gln 805 | Arg | Ala | Tyr | Ala | Leu 810 | Asp | Thr | Glu | Val | Ala 815 | Ala |
| Ser | Cys | Gly | Gly 820 | Val | Val | Leu | Val | Gly 825 | Leu | Met | Ala | Leu | Thr 830 | Leu | Ser |
| Pro | Tyr | Tyr 835 | Lys | Arg | Tyr | Ile | Ser 840 | Trp | Cys | Leu | Trp | Trp 845 | Leu | Gln | Tyr |
| Phe | Leu 850 | Thr | Arg | Val | Glu | Ala 855 | Gln | Leu | His | Val | Trp 860 | Ile | Pro | Pro | Leu |
| Asn 865 | Val | Arg | Gly | Gly | Arg 870 | Asp | Ala | Val | Ile | Leu 875 | Leu | Met | Cys | Ala | Val 880 |
| His | Pro | Thr | Leu | Val 885 | Phe | Asp | Ile | Thr | Lys 890 | Leu | Leu | Leu | Ala | Val 895 | Phe |
| Gly | Pro | Leu | Trp 900 | Ile | Leu | Gln | Ala | Ser 905 | Leu | Leu | Lys | Val | Pro 910 | Tyr | Phe |
| Val | Arg | Val 915 | Gln | Gly | Leu | Leu | Arg 920 | Phe | Cys | Ala | Leu | Ala 925 | Arg | Lys | Met |
| Ile | Gly 930 | Gly | His | Tyr | Val | Gln 935 | Met | Val | Ile | Ile | Lys 940 | Leu | Gly | Ala | Leu |
| Thr 945 | Gly | Thr | Tyr | Val | Tyr 950 | Asn | His | Leu | Thr | Pro 955 | Leu | Arg | Asp | Trp | Ala 960 |
| His | Asn | Gly | Leu | Arg 965 | Asp | Leu | Ala | Val | Ala 970 | Val | Glu | Pro | Val | Val 975 | Phe |
| Ser | Gln | Met | Glu 980 | Thr | Lys | Leu | Ile | Thr 985 | Trp | Gly | Ala | Asp | Thr 990 | Ala | Ala |

Cys Gly Asp Ile Ile Asn Gly Leu Pro Val Ser Ala Arg Arg Gly Arg
            995                 1000                1005

Glu Ile Leu Leu Gly Pro Ala Asp Gly Met Val Ser Lys Gly Trp Arg
1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
            1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
            1075                1080                1085

Thr Ile Ala Ser Pro Lys Gly Pro Val Ile Gln Met Tyr Thr Asn Val
            1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
            1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
            1155                1160                1165

Leu Leu Cys Pro Ala Gly His Ala Val Gly Ile Phe Arg Ala Ala Val
            1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
            1205                1210                1215

Pro Val Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
            1315                1320                1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
1410                1415                1420

```
Val  Ile  Pro  Thr  Ser  Gly  Asp  Val  Val  Val  Ala  Thr  Asp  Ala  Leu
1425                1430                1435                          1440

Met  Thr  Gly  Tyr  Thr  Gly  Asp  Phe  Asp  Ser  Val  Ile  Asp  Cys  Asn  Thr
               1445                1450                     1455

Cys  Val  Thr  Gln  Thr  Val  Asp  Phe  Ser  Leu  Asp  Pro  Thr  Phe  Thr  Ile
               1460                1465                     1470

Glu  Thr  Ile  Thr  Leu  Pro  Gln  Asp  Ala  Val  Ser  Arg  Thr  Gln  Arg  Arg
               1475                1480                     1485

Gly  Arg  Thr  Gly  Arg  Gly  Lys  Pro  Gly  Ile  Tyr  Arg  Phe  Val  Ala  Pro
1490                1495                1500

Gly  Glu  Arg  Pro  Ser  Gly  Met  Phe  Asp  Ser  Ser  Val  Leu  Cys  Glu  Cys
1505                1510                1515                          1520

Tyr  Asp  Ala  Gly  Cys  Ala  Trp  Tyr  Glu  Leu  Thr  Pro  Ala  Glu  Thr  Thr
               1525                1530                     1535

Val  Arg  Leu  Arg  Ala  Tyr  Met  Asn  Thr  Pro  Gly  Leu  Pro  Val  Cys  Gln
               1540                1545                     1550

Asp  His  Leu  Glu  Phe  Trp  Glu  Gly  Val  Phe  Thr  Gly  Leu  Thr  His  Ile
               1555                1560                     1565

Asp  Ala  His  Phe  Leu  Ser  Gln  Thr  Lys  Gln  Ser  Gly  Glu  Asn  Leu  Pro
1570                1575                1580

Tyr  Leu  Val  Ala  Tyr  Gln  Ala  Thr  Val  Cys  Ala  Arg  Ala  Gln  Ala  Pro
1585                1590                1595                          1600

Pro  Pro  Ser  Trp  Asp  Gln  Met  Trp  Lys  Cys  Leu  Ile  Arg  Leu  Lys  Pro
               1605                1610                     1615

Thr  Leu  His  Gly  Pro  Thr  Pro  Leu  Leu  Tyr  Arg  Leu  Gly  Ala  Val  Gln
               1620                1625                     1630

Asn  Glu  Ile  Thr  Leu  Thr  His  Pro  Val  Thr  Lys  Tyr  Ile  Met  Thr  Cys
               1635                1640                     1645

Met  Ser  Ala  Asp  Leu  Glu  Val  Val  Thr  Ser  Thr  Trp  Val  Leu  Val  Gly
               1650                1655                     1660

Gly  Val  Leu  Ala  Ala  Leu  Ala  Ala  Tyr  Cys  Leu  Ser  Thr  Gly  Cys  Val
1665                1670                1675                          1680

Val  Ile  Val  Gly  Arg  Val  Val  Leu  Ser  Gly  Lys  Pro  Ala  Ile  Ile  Pro
               1685                1690                     1695

Asp  Arg  Glu  Val  Leu  Tyr  Arg  Glu  Phe  Asp  Glu  Met  Glu  Glu  Cys  Ser
               1700                1705                     1710

Gln  His  Leu  Pro  Tyr  Ile  Glu  Gln  Gly  Met  Met  Leu  Ala  Glu  Gln  Phe
               1715                1720                     1725

Lys  Gln  Lys  Ala  Leu  Gly  Leu  Leu  Gln  Thr  Ala  Ser  Arg  Gln  Ala  Glu
               1730                1735                     1740

Val  Ile  Ala  Pro  Ala  Val  Gln  Thr  Asn  Trp  Gln  Lys  Leu  Glu  Thr  Phe
1745                1750                1755                          1760

Trp  Ala  Lys  His  Met  Trp  Asn  Phe  Ile  Ser  Gly  Ile  Gln  Tyr  Leu  Ala
               1765                1770                     1775

Gly  Leu  Ser  Thr  Leu  Pro  Gly  Asn  Pro  Ala  Ile  Ala  Ser  Leu  Met  Ala
               1780                1785                     1790

Phe  Thr  Ala  Ala  Val  Thr  Ser  Pro  Leu  Thr  Thr  Ser  Gln  Thr  Leu  Leu
               1795                1800                     1805

Phe  Asn  Ile  Leu  Gly  Gly  Trp  Val  Ala  Ala  Gln  Leu  Ala  Ala  Pro  Gly
               1810                1815                     1820

Ala  Ala  Thr  Ala  Phe  Val  Gly  Ala  Gly  Leu  Ala  Gly  Ala  Ala  Ile  Gly
1825                1830                1835                          1840

Ser  Val  Gly  Leu  Gly  Lys  Val  Leu  Ile  Asp  Ile  Leu  Ala  Gly  Tyr  Gly
```

-continued

```
                    1845                          1850                          1855
Ala  Gly  Val  Ala  Gly  Ala  Leu  Val  Ala  Phe  Lys  Ile  Met  Ser  Gly  Glu
              1860                         1865                         1870
Val  Pro  Ser  Thr  Glu  Asp  Leu  Val  Asn  Leu  Leu  Pro  Ala  Ile  Leu  Ser
              1875                         1880                         1885
Pro  Gly  Ala  Leu  Val  Val  Gly  Val  Val  Cys  Ala  Ala  Ile  Leu  Arg  Arg
              1890                         1895                         1900
His  Val  Gly  Pro  Gly  Glu  Gly  Ala  Val  Gln  Trp  Met  Asn  Arg  Leu  Ile
1905                      1910                         1915                    1920
Ala  Phe  Ala  Ser  Arg  Gly  Asn  His  Val  Ser  Pro  Thr  His  Tyr  Val  Pro
              1925                         1930                         1935
Glu  Ser  Asp  Ala  Ala  Ala  Arg  Val  Thr  Ala  Ile  Leu  Ser  Ser  Leu  Thr
              1940                         1945                         1950
Val  Thr  Gln  Leu  Leu  Arg  Arg  Leu  His  Gln  Trp  Ile  Ser  Ser  Glu  Cys
              1955                         1960                         1965
Thr  Thr  Pro  Cys  Ser  Gly  Ser  Trp  Leu  Arg  Asp  Ile  Trp  Asp  Trp  Ile
              1970                         1975                         1980
Cys  Glu  Val  Leu  Ser  Asp  Phe  Lys  Thr  Trp  Leu  Lys  Ala  Lys  Leu  Met
1985                      1990                         1995                    2000
Pro  Gln  Leu  Pro  Gly  Ile  Pro  Phe  Val  Ser  Cys  Gln  Arg  Gly  Tyr  Lys
              2005                         2010                         2015
Gly  Val  Trp  Arg  Val  Asp  Gly  Ile  Met  His  Thr  Arg  Cys  His  Cys  Gly
              2020                         2025                         2030
Ala  Glu  Ile  Thr  Gly  His  Val  Lys  Asn  Gly  Thr  Met  Arg  Ile  Val  Gly
              2035                         2040                         2045
Pro  Arg  Thr  Cys  Arg  Asn  Met  Trp  Ser  Gly  Thr  Phe  Pro  Ile  Asn  Ala
              2050                         2055                         2060
Tyr  Thr  Thr  Gly  Pro  Cys  Thr  Pro  Leu  Pro  Ala  Pro  Asn  Tyr  Thr  Phe
2065                      2070                         2075                    2080
Ala  Leu  Trp  Arg  Val  Ser  Ala  Glu  Glu  Tyr  Val  Glu  Ile  Arg  Gln  Val
              2085                         2090                         2095
Gly  Asp  Phe  His  Tyr  Val  Thr  Gly  Met  Thr  Thr  Asp  Asn  Leu  Lys  Cys
              2100                         2105                         2110
Pro  Cys  Gln  Val  Pro  Ser  Pro  Glu  Phe  Phe  Thr  Glu  Leu  Asp  Gly  Val
              2115                         2120                         2125
Arg  Leu  His  Arg  Phe  Ala  Pro  Pro  Cys  Lys  Pro  Leu  Leu  Arg  Glu  Glu
              2130                         2135                         2140
Val  Ser  Phe  Arg  Val  Gly  Leu  His  Glu  Tyr  Pro  Val  Gly  Ser  Gln  Leu
2145                      2150                         2155                    2160
Pro  Cys  Glu  Pro  Glu  Pro  Asp  Val  Ala  Val  Leu  Thr  Ser  Met  Leu  Thr
              2165                         2170                         2175
Asp  Pro  Ser  His  Ile  Thr  Ala  Glu  Ala  Ala  Gly  Arg  Arg  Leu  Ala  Arg
              2180                         2185                         2190
Gly  Ser  Pro  Pro  Ser  Val  Ala  Ser  Ser  Ser  Ala  Ser  Gln  Leu  Ser  Ala
              2195                         2200                         2205
Pro  Ser  Leu  Lys  Ala  Thr  Cys  Thr  Ala  Asn  His  Asp  Ser  Pro  Asp  Ala
              2210                         2215                         2220
Glu  Leu  Ile  Glu  Ala  Asn  Leu  Leu  Trp  Arg  Gln  Glu  Met  Gly  Gly  Asn
2225                      2230                         2235                    2240
Ile  Thr  Arg  Val  Glu  Ser  Glu  Asn  Lys  Val  Val  Ile  Leu  Asp  Ser  Phe
              2245                         2250                         2255
Asp  Pro  Leu  Val  Ala  Glu  Glu  Asp  Glu  Arg  Glu  Ile  Ser  Val  Pro  Ala
              2260                         2265                         2270
```

```
Glu  Ile  Leu  Arg  Lys  Ser  Arg  Arg  Phe  Ala  Gln  Ala  Leu  Pro  Val  Trp
     2275                2280                               2285

Ala  Arg  Pro  Asp  Tyr  Asn  Pro  Pro  Leu  Val  Glu  Thr  Trp  Lys  Lys  Pro
     2290                2295                               2300

Asp  Tyr  Glu  Pro  Pro  Val  Val  His  Gly  Cys  Pro  Leu  Pro  Pro  Pro  Lys
2305                2310                     2315                          2320

Ser  Pro  Pro  Val  Pro  Pro  Pro  Arg  Lys  Lys  Arg  Thr  Val  Val  Leu  Thr
                    2325                     2330                     2335

Glu  Ser  Thr  Leu  Ser  Thr  Ala  Leu  Ala  Glu  Leu  Ala  Thr  Arg  Ser  Phe
                    2340                     2345                     2350

Gly  Ser  Ser  Ser  Thr  Ser  Gly  Ile  Thr  Gly  Asp  Asn  Thr  Thr  Thr  Ser
                    2355                     2360                     2365

Ser  Glu  Pro  Ala  Pro  Ser  Gly  Cys  Pro  Pro  Asp  Ser  Asp  Ala  Glu  Ser
                    2370                     2375                     2380

Tyr  Ser  Ser  Met  Pro  Pro  Leu  Glu  Gly  Glu  Pro  Gly  Asp  Pro  Asp  Leu
2385                     2390                     2395                     2400

Ser  Asp  Gly  Ser  Trp  Ser  Thr  Val  Ser  Ser  Glu  Ala  Asn  Ala  Glu  Asp
                    2405                     2410                     2415

Val  Val  Cys  Cys  Ser  Met  Ser  Tyr  Ser  Trp  Thr  Gly  Ala  Leu  Val  Thr
                    2420                     2425                     2430

Pro  Cys  Ala  Ala  Glu  Glu  Gln  Lys  Leu  Pro  Ile  Asn  Ala  Leu  Ser  Asn
                    2435                     2440                     2445

Ser  Leu  Leu  Arg  His  His  Asn  Leu  Val  Tyr  Ser  Thr  Thr  Ser  Arg  Ser
     2450                     2455                     2460

Ala  Cys  Gln  Arg  Gln  Lys  Lys  Val  Thr  Phe  Asp  Arg  Leu  Gln  Val  Leu
2465                     2470                     2475                     2480

Asp  Ser  His  Tyr  Gln  Asp  Val  Leu  Lys  Glu  Val  Lys  Ala  Ala  Ala  Ser
                    2485                     2490                     2495

Lys  Val  Lys  Ala  Asn  Leu  Leu  Ser  Val  Glu  Glu  Ala  Cys  Ser  Leu  Thr
                    2500                     2505                     2510

Pro  Pro  His  Ser  Ala  Lys  Ser  Lys  Phe  Gly  Tyr  Gly  Ala  Lys  Asp  Val
                    2515                     2520                     2525

Arg  Cys  His  Ala  Arg  Lys  Ala  Val  Thr  His  Ile  Asn  Ser  Val  Trp  Lys
                    2530                     2535                     2540

Asp  Leu  Leu  Glu  Asp  Asn  Val  Thr  Pro  Ile  Asp  Thr  Thr  Ile  Met  Ala
2545                     2550                     2555                     2560

Lys  Asn  Glu  Val  Phe  Cys  Val  Gln  Pro  Glu  Lys  Gly  Gly  Arg  Lys  Pro
                    2565                     2570                     2575

Ala  Arg  Leu  Ile  Val  Phe  Pro  Asp  Leu  Gly  Val  Arg  Val  Cys  Glu  Lys
                    2580                     2585                     2590

Met  Ala  Leu  Tyr  Asp  Val  Val  Thr  Lys  Leu  Pro  Leu  Ala  Val  Met  Gly
     2595                     2600                     2605

Ser  Ser  Tyr  Gly  Phe  Gln  Tyr  Ser  Pro  Gly  Gln  Arg  Val  Glu  Phe  Leu
     2610                     2615                     2620

Val  Gln  Ala  Trp  Lys  Ser  Lys  Lys  Thr  Pro  Met  Gly  Phe  Ser  Tyr  Asp
2625                     2630                     2635                     2640

Thr  Arg  Cys  Phe  Asp  Ser  Thr  Val  Thr  Glu  Ser  Asp  Ile  Arg  Thr  Glu
                    2645                     2650                     2655

Glu  Ala  Ile  Tyr  Gln  Cys  Cys  Asp  Leu  Asp  Pro  Gln  Ala  Arg  Val  Ala
                    2660                     2665                     2670

Ile  Lys  Ser  Leu  Thr  Glu  Arg  Leu  Tyr  Val  Gly  Gly  Pro  Leu  Thr  Asn
                    2675                     2680                     2685

Ser  Arg  Gly  Glu  Asn  Cys  Gly  Tyr  Arg  Arg  Cys  Arg  Ala  Ser  Gly  Val
     2690                     2695                     2700
```

```
Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asp
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ala Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Ile
            2980                2985                2990

Trp Phe Cys Leu Leu Leu Leu Ala Ala Gly Val Gly Ile Tyr Leu Leu
        2995                3000                3005

Pro Asn Arg
    3010
```

( 2 ) INFORMATION FOR SEQ ID NO:37:

( i ) SEQUENCE CHARACTERISTICS:
        ( A ) LENGTH: 192 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

```
Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Ala
            20                  25                  30
```

```
Pro Gly Cys Val Pro Cys Val Arg Glu Gly Asn Ala Ser Arg Cys Trp
        35                  40                  45
Val Ala Met Thr Pro Thr Val Ala Ala Arg Asp Gly Arg Leu Pro Thr
    50                  55                  60
Thr Gln Leu Arg Arg His Ile Asp Leu Leu Val Gly Ser Ala Thr Leu
65                      70                  75                  80
Cys Ser Ala Leu Tyr Val Gly Asp Leu Cys Gly Ser Ile Phe Leu Val
                85                  90                  95
Gly Gln Leu Phe Thr Phe Ser Pro Arg Arg His Trp Thr Thr Gln Gly
            100                 105                 110
Cys Asn Cys Ser Ile Tyr Pro Gly His Ile Thr Gly His Arg Met Ala
        115                 120                 125
Trp Asp Met Met Met Asn Trp Ser Pro Thr Thr Ala Leu Val Val Ala
    130                 135                 140
Gln Leu Leu Arg Ile Pro Gln Ala Ile Leu Asp Met Ile Ala Gly Ala
145                 150                 155                 160
His Trp Gly Val Leu Ala Gly Ile Ala Tyr Phe Ser Met Val Gly Asn
                165                 170                 175
Trp Ala Lys Val Leu Val Val Leu Leu Leu Phe Ala Gly Val Asp Ala
                180                 185                 190
```

(2) INFORMATION FOR SEQ ID NO:38:

(i) SEQUENCE CHARACTERISTICS:
      (A) LENGTH: 192 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:38:

```
Tyr Gln Val Arg Asn Ser Thr Gly Leu Tyr His Val Thr Asn Asp Cys
1               5                   10                  15
Pro Asn Ser Ser Ile Val Tyr Glu Ala Ala Asp Ala Ile Leu His Thr
                20                  25                  30
Pro Gly Cys Val Pro Cys Val Arg Glu Gly Asn Ala Ser Arg Cys Trp
        35                  40                  45
Val Ala Met Thr Pro Thr Val Ala Thr Arg Asp Gly Lys Leu Pro Ala
    50                  55                  60
Thr Gln Leu Arg Arg His Ile Asp Leu Leu Val Gly Ser Ala Thr Leu
65                      70                  75                  80
Cys Ser Ala Leu Tyr Val Gly Asp Leu Cys Gly Ser Val Phe Leu Val
                85                  90                  95
Gly Gln Leu Phe Thr Phe Ser Pro Arg Arg His Trp Thr Thr Gln Gly
            100                 105                 110
Cys Asn Cys Ser Ile Tyr Pro Gly His Ile Thr Gly His Arg Met Ala
        115                 120                 125
Trp Asp Met Met Met Asn Trp Ser Pro Thr Thr Ala Leu Val Met Ala
    130                 135                 140
Gln Leu Leu Arg Ile Pro Gln Ala Ile Leu Asp Met Ile Ala Gly Ala
145                 150                 155                 160
His Trp Gly Val Leu Ala Gly Ile Ala Tyr Phe Ser Met Val Gly Asn
                165                 170                 175
Trp Ala Lys Val Leu Val Val Leu Leu Leu Phe Ala Gly Val Asp Ala
                180                 185                 190
```

( 2 ) INFORMATION FOR SEQ ID NO:39:

( i ) SEQUENCE CHARACTERISTICS:
        ( A ) LENGTH: 192 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:39:

```
Tyr Glu Val Arg Asn Val Ser Gly Ile Tyr His Val Thr Asn Asp Cys
 1               5                  10                  15
Ser Asn Ser Ser Ile Val Tyr Glu Ala Ala Asp Met Ile Met His Thr
                20                  25                  30
Pro Gly Cys Val Pro Cys Val Arg Glu Ser Asn Phe Ser Arg Cys Trp
            35                  40                  45
Val Ala Leu Thr Pro Thr Leu Ala Ala Arg Asn Ser Ser Ile Pro Thr
        50                  55                  60
Thr Thr Ile Arg Arg His Val Asp Leu Leu Val Gly Ala Ala Ala Leu
65                  70                  75                  80
Cys Ser Ala Met Tyr Val Gly Asp Leu Cys Gly Ser Val Phe Leu Val
                85                  90                  95
Ser Gln Leu Phe Thr Phe Ser Pro Arg Arg Tyr Glu Thr Val Gln Asp
                100                 105                 110
Cys Asn Cys Ser Ile Tyr Pro Gly His Val Ser Gly His Arg Met Ala
            115                 120                 125
Trp Asp Met Met Met Asn Trp Ser Pro Thr Thr Ala Leu Val Val Ser
    130                 135                 140
Gln Leu Leu Arg Ile Pro Gln Ala Val Val Asp Met Val Ala Gly Ala
145                 150                 155                 160
His Trp Gly Val Leu Ala Gly Leu Ala Tyr Tyr Ser Met Val Gly Asn
                165                 170                 175
Trp Ala Lys Val Leu Ile Val Met Leu Leu Phe Ala Gly Val Asp Gly
            180                 185                 190
```

( 2 ) INFORMATION FOR SEQ ID NO:40:

( i ) SEQUENCE CHARACTERISTICS:
        ( A ) LENGTH: 192 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

```
His Gln Val Arg Asn Ser Thr Gly Leu Tyr His Val Thr Asn Asp Cys
 1               5                  10                  15
Pro Asn Ser Ser Ile Val Tyr Glu Ala Ala Asp Ala Ile Leu His Thr
                20                  25                  30
Pro Gly Cys Val Pro Cys Val His Glu Gly Asn Val Ser Arg Cys Trp
            35                  40                  45
Val Ala Val Thr Pro Thr Val Ala Thr Arg Asp Gly Lys Leu Pro Thr
        50                  55                  60
Thr Gln Leu Arg Arg His Ile Asp Leu Leu Val Gly Ser Ala Thr Leu
65                  70                  75                  80
Cys Ser Ala Leu Tyr Val Gly Asp Leu Cys Gly Ser Val Phe Leu Val
                85                  90                  95
Gly Gln Leu Phe Thr Phe Ser Pro Arg Arg His Trp Thr Thr Gln Gly
```

|     |     |     | 100 |     |     |     | 105 |     |     |     | 110 |     |     |     |
| --- | --- | --- | --- | --- | --- | --- | --- | --- | --- | --- | --- | --- | --- | --- |
| Cys | Asn | Cys | Ser | Ile | Tyr | Pro | Gly | His | Ile | Thr | Gly | His | Arg | Met | Ala |
|     |     | 115 |     |     |     |     | 120 |     |     |     |     | 125 |     |     |     |
| Trp | Asp | Met | Met | Met | Asn | Trp | Ser | Pro | Thr | Ala | Ala | Leu | Val | Met | Ala |
|     | 130 |     |     |     |     | 135 |     |     |     |     | 140 |     |     |     |     |
| Gln | Leu | Leu | Arg | Ile | Pro | Gln | Ala | Ile | Met | Asp | Met | Ile | Ala | Gly | Ala |
| 145 |     |     |     |     | 150 |     |     |     |     | 155 |     |     |     |     | 160 |
| His | Trp | Gly | Val | Leu | Ala | Gly | Ile | Ala | Tyr | Phe | Ser | Met | Val | Gly | Asn |
|     |     |     |     | 165 |     |     |     |     | 170 |     |     |     |     | 175 |     |
| Trp | Ala | Lys | Val | Leu | Val | Val | Leu | Leu | Leu | Phe | Ala | Gly | Val | Asp | Ala |
|     |     |     | 180 |     |     |     |     | 185 |     |     |     |     | 190 |     |     |

( 2 ) INFORMATION FOR SEQ ID NO:41:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:41:

| Tyr | Gln | Val | Arg | Asn | Ser | Thr | Gly | Leu | Tyr | His | Val | Thr | Asn | Asp | Cys |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Pro | Asn | Ser | Ser | Ile | Val | Tyr | Glu | Ala | His | Asp | Ala | Ile | Leu | His | Thr |
|     |     |     | 20  |     |     |     |     | 25  |     |     |     |     | 30  |     |     |
| Pro | Gly | Cys | Val | Pro | Cys | Val | Arg | Glu | Gly | Asn | Val | Ser | Arg | Cys | Trp |
|     |     |     | 35  |     |     |     |     | 40  |     |     |     |     | 45  |     |     |
| Val | Ala | Met | Thr | Pro | Thr | Val | Ala | Thr | Arg | Asp | Gly | Lys | Leu | Pro | Ala |
|     | 50  |     |     |     |     | 55  |     |     |     |     | 60  |     |     |     |     |
| Thr | Gln | Leu | Arg | Arg | His | Ile | Asp | Leu | Leu | Val | Gly | Ser | Ala | Thr | Leu |
| 65  |     |     |     |     | 70  |     |     |     |     | 75  |     |     |     |     | 80  |
| Cys | Ser | Ala | Leu | Tyr | Val | Gly | Asp | Leu | Cys | Gly | Ser | Val | Phe | Leu | Ile |
|     |     |     |     | 85  |     |     |     |     | 90  |     |     |     |     | 95  |     |
| Gly | Gln | Leu | Phe | Thr | Phe | Ser | Pro | Arg | Arg | His | Trp | Thr | Thr | Gln | Gly |
|     |     |     | 100 |     |     |     |     | 105 |     |     |     |     | 110 |     |     |
| Cys | Asn | Cys | Ser | Ile | Tyr | Pro | Gly | His | Ile | Thr | Gly | His | Arg | Met | Ala |
|     |     | 115 |     |     |     |     | 120 |     |     |     |     | 125 |     |     |     |
| Trp | Asp | Met | Met | Met | Asn | Trp | Ser | Pro | Thr | Ala | Ala | Leu | Val | Met | Ala |
|     | 130 |     |     |     |     | 135 |     |     |     |     | 140 |     |     |     |     |
| Gln | Leu | Leu | Arg | Ile | Pro | Gln | Ala | Ile | Leu | Asp | Met | Ile | Ala | Gly | Ala |
| 145 |     |     |     |     | 150 |     |     |     |     | 155 |     |     |     |     | 160 |
| His | Trp | Gly | Val | Leu | Ala | Gly | Ile | Ala | Tyr | Phe | Ser | Met | Val | Gly | Asn |
|     |     |     |     | 165 |     |     |     |     | 170 |     |     |     |     | 175 |     |
| Trp | Ala | Lys | Val | Leu | Val | Val | Leu | Leu | Leu | Phe | Ala | Gly | Val | Asp | Ala |
|     |     |     | 180 |     |     |     |     | 185 |     |     |     |     | 190 |     |     |

( 2 ) INFORMATION FOR SEQ ID NO:42:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:42:

| Tyr | Glu | Val | Arg | Asn | Val | Ser | Gly | Ile | Tyr | His | Val | Thr | Asn | Asp | Cys |
| --- | --- | --- | --- | --- | --- | --- | --- | --- | --- | --- | --- | --- | --- | --- | --- |

|   | 1 |   |   |   | 5 |   |   |   |   | 10 |   |   |   |   | 15 |
|---|---|---|---|---|---|---|---|---|---|---|---|---|---|---|---|
| Ser | Asn | Ser | Ser | Ile | Val | Tyr | Glu | Ala | Ala | Asp | Met | Ile | Met | His | Thr |
|   |   |   | 20 |   |   |   |   | 25 |   |   |   |   | 30 |   |   |
| Pro | Gly | Cys | Val | Pro | Cys | Val | Arg | Glu | Asp | Asn | Ser | Ser | Arg | Cys | Trp |
|   |   | 35 |   |   |   | 40 |   |   |   |   | 45 |   |   |   |   |
| Val | Ala | Leu | Thr | Pro | Thr | Leu | Ala | Ala | Arg | Asn | Ala | Ser | Val | Pro | Thr |
|   | 50 |   |   |   |   | 55 |   |   |   |   | 60 |   |   |   |   |
| Thr | Thr | Ile | Arg | Arg | His | Val | Asp | Leu | Leu | Val | Gly | Ala | Ala | Ala | Phe |
| 65 |   |   |   |   | 70 |   |   |   |   | 75 |   |   |   |   | 80 |
| Cys | Ser | Ala | Met | Tyr | Val | Gly | Asp | Leu | Cys | Gly | Ser | Val | Phe | Leu | Val |
|   |   |   |   | 85 |   |   |   |   | 90 |   |   |   |   | 95 |   |
| Ser | Gln | Leu | Phe | Thr | Phe | Ser | Pro | Arg | Arg | His | Glu | Thr | Val | Gln | Asp |
|   |   |   | 100 |   |   |   |   | 105 |   |   |   |   | 110 |   |   |
| Cys | Asn | Cys | Ser | Ile | Tyr | Pro | Gly | His | Leu | Ser | Gly | His | Arg | Met | Ala |
|   |   | 115 |   |   |   |   | 120 |   |   |   |   | 125 |   |   |   |
| Trp | Asp | Met | Met | Met | Asn | Trp | Ser | Pro | Thr | Thr | Ala | Leu | Val | Val | Ser |
|   | 130 |   |   |   |   | 135 |   |   |   |   | 140 |   |   |   |   |
| Gln | Leu | Leu | Arg | Ile | Pro | Gln | Ala | Val | Val | Asp | Met | Val | Ala | Gly | Ala |
| 145 |   |   |   |   | 150 |   |   |   |   | 155 |   |   |   |   | 160 |
| His | Trp | Gly | Val | Leu | Ala | Gly | Leu | Ala | Tyr | Tyr | Ser | Met | Val | Gly | Asn |
|   |   |   |   | 165 |   |   |   |   | 170 |   |   |   |   | 175 |   |
| Trp | Ala | Lys | Val | Leu | Ile | Val | Ala | Leu | Leu | Phe | Ala | Gly | Val | Asp | Gly |
|   |   |   | 180 |   |   |   |   | 185 |   |   |   |   | 190 |   |   |

(2) INFORMATION FOR SEQ ID NO:43:

(i) SEQUENCE CHARACTERISTICS:
(A) LENGTH: 192 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:43:

| Tyr | Glu | Val | His | Asn | Val | Ser | Gly | Ile | Tyr | His | Val | Thr | Asn | Asp | Cys |
|---|---|---|---|---|---|---|---|---|---|---|---|---|---|---|---|
| 1 |   |   |   | 5 |   |   |   |   | 10 |   |   |   |   | 15 |   |
| Ser | Asn | Ala | Ser | Ile | Val | Tyr | Glu | Ala | Ala | Asp | Leu | Ile | Met | His | Thr |
|   |   |   | 20 |   |   |   |   | 25 |   |   |   |   | 30 |   |   |
| Pro | Gly | Cys | Val | Pro | Cys | Val | Arg | Glu | Gly | Asn | Ser | Ser | Arg | Cys | Trp |
|   |   | 35 |   |   |   | 40 |   |   |   |   | 45 |   |   |   |   |
| Val | Ala | Leu | Thr | Pro | Thr | Leu | Ala | Ala | Arg | Asn | Val | Thr | Ile | Pro | Thr |
|   | 50 |   |   |   |   | 55 |   |   |   |   | 60 |   |   |   |   |
| Thr | Thr | Ile | Arg | Arg | His | Val | Asp | Leu | Leu | Val | Gly | Ala | Ala | Ala | Phe |
| 65 |   |   |   |   | 70 |   |   |   |   | 75 |   |   |   |   | 80 |
| Cys | Ser | Ala | Met | Tyr | Val | Gly | Asp | Leu | Cys | Gly | Ser | Val | Phe | Leu | Val |
|   |   |   |   | 85 |   |   |   |   | 90 |   |   |   |   | 95 |   |
| Ser | Gln | Leu | Phe | Thr | Phe | Ser | Pro | Arg | Arg | His | Val | Thr | Leu | Gln | Asp |
|   |   |   | 100 |   |   |   |   | 105 |   |   |   |   | 110 |   |   |
| Cys | Asn | Cys | Ser | Ile | Tyr | Pro | Gly | His | Val | Ser | Gly | His | Arg | Met | Ala |
|   |   | 115 |   |   |   |   | 120 |   |   |   |   | 125 |   |   |   |
| Trp | Asp | Met | Met | Met | Asn | Trp | Ser | Pro | Thr | Thr | Ala | Leu | Val | Val | Ser |
|   | 130 |   |   |   |   | 135 |   |   |   |   | 140 |   |   |   |   |
| Gln | Leu | Leu | Arg | Ile | Pro | Gln | Ala | Val | Val | Asp | Met | Val | Ala | Gly | Ala |
| 145 |   |   |   |   | 150 |   |   |   |   | 155 |   |   |   |   | 160 |
| His | Trp | Gly | Val | Leu | Ala | Gly | Leu | Ala | Tyr | Tyr | Ser | Met | Val | Gly | Asn |
|   |   |   |   | 165 |   |   |   |   | 170 |   |   |   |   | 175 |   |

Trp Ala Lys Val Leu Ile Val Met Leu Leu Phe Ala Gly Val Asp Gly
            180                 185                 190

(2) INFORMATION FOR SEQ ID NO:44:

(i) SEQUENCE CHARACTERISTICS:
       (A) LENGTH: 192 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:44:

Tyr Gln Val Arg Asn Ser Ser Gly Ile Tyr His Val Thr Asn Asp Cys
1               5                   10                  15

Pro Asn Ser Ser Ile Val Tyr Glu Thr Ala Asp Thr Ile Leu His Ser
            20                  25                  30

Pro Gly Cys Val Pro Cys Val Arg Glu Gly Asn Ala Ser Lys Cys Trp
            35                  40                  45

Val Pro Val Ala Pro Thr Val Ala Thr Arg Asp Gly Asn Leu Pro Ala
        50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
                100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Met Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190

(2) INFORMATION FOR SEQ ID NO:45:

(i) SEQUENCE CHARACTERISTICS:
       (A) LENGTH: 192 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:45:

Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Ala
            20                  25                  30

Pro Gly Cys Val Pro Cys Val Arg Glu Asp Asn Val Ser Arg Cys Trp
            35                  40                  45

Val Ala Val Thr Pro Thr Val Ala Thr Lys Asp Gly Lys Leu Pro Thr
        50                  55                  60

Thr Gln Leu Arg Arg His Ile Asp Leu Leu Val Gly Ser Ala Thr Leu
65                  70                  75                  80

|  |  |  |  |  |  |  |  |  |  |  |  |  |  |
|---|---|---|---|---|---|---|---|---|---|---|---|---|---|
| Cys | Ser | Ala | Leu | Tyr 85 | Val | Gly | Asp | Leu | Cys 90 | Gly | Ser | Ile | Phe | Leu 95 | Val |
| Gly | Gln | Leu | Phe 100 | Thr | Phe | Ser | Pro | Arg 105 | Arg | His | Trp | Thr | Thr 110 | Gln | Asp |
| Cys | Asn | Cys 115 | Ser | Ile | Tyr | Pro | Gly 120 | His | Ile | Thr | Gly | His 125 | Arg | Met | Ala |
| Trp | Asp 130 | Met | Met | Met | Asn | Trp 135 | Ser | Pro | Thr | Ala | Ala 140 | Leu | Val | Val | Ala |
| Gln 145 | Leu | Leu | Arg | Ile | Pro 150 | Gln | Ala | Ile | Leu | Asp 155 | Met | Ile | Ala | Gly | Ala 160 |
| His | Trp | Gly | Val | Leu 165 | Ala | Gly | Met | Ala | Tyr 170 | Phe | Ser | Met | Val | Gly 175 | Asn |
| Trp | Ala | Lys | Val 180 | Leu | Val | Val | Leu | Leu 185 | Leu | Phe | Ala | Gly | Val 190 | Asp | Ala |

IMMUNOREACTIVE POLYPEPTIDE COMPOSITIONS

This application is a divisional, of application Ser. No. 08/231,368, filed Apr. 19, 1994, which is a continuation of application Ser. No. 07/759,575 filed Sep. 13, 1991.

TECHNICAL FIELD

This invention relates generally to immunoreactive polypeptide compositions, methods of using the compositions in immunological applications, and materials and methods for making the compositions.

BACKGROUND

The hepatitis C virus has been recently identified as the major causative agent of post-transfusion Non-A, Non-B hepatitis (NANHB), as well as a significant cause of community-acquired NANBH. Materials and methods for obtaining the viral genomic sequences are known. See, e.g. PCT Publication Nos. WO89/04669, WO90/11089 & WO90/14436.

Molecular characterization of the HCV genome indicates that it is a RNA molecule of positive polarity containing approximately 10,000 nucleotides that encodes a polyprotein of about 3011 amino acids. Several lines of evidence suggest that HCV has a similar genetic organization to the viruses of the family Flaviviridae, which includes the flavi- and pestivirus. Like its pesti- and flaviviral relatives, HCV appears to encode a large polyprotein precursor from which individual viral proteins (both structural and non-structural) are processed.

RNA-containing viruses can have relatively high rates of spontaneous mutation, i.e., reportedly on the order of $10^{-3}$ to $10^{-4}$ per incorporated nucleotide. Therefore, since heterogeneity and fluidity of genotype are common in RNA viruses, there may be multiple viral isolates, which may be virulent or avirulent, within the HCV species.

A number of different isolates of HCV have now been identified. The sequences of these isolates demonstrate the limited heterogeneity characteristic of RNA viruses.

Isolate HCV J1.1 is described in Kubo, Y. et al. (1989), Japan. Nucl. Acids Res. 17:10367–10372; Takeuchi, K. et al. (1990), Gene 91:287–291; Takeuchi et al. (1990), J. Gen. Virol. 71:3027–3033; Takeuchi et al. (1990), Nucl. Acids Res. 18:4626.

The complete coding sequences plus the 5'- and 3'-terminal sequences of two independent isolates, "HCV-J" and "BK", are described by Kato et al. and Takamizawa et al, respectively. (Kato et al. (1990), Proc. Natl. Acad. Sci. USA 87:9524–9528; Takamizawa et al (1991), J. Virol. ,65:1105–1113.)

Other publications describing HCV isolates are the following;

"HCV-1": Choo et al (1990), Brit. Med. Bull. 46:423–441; Choo et al. (1991), Proc. Natl. Acad. Sci. USA 88:2451–2455; Han et al. (1991), Proc. Natl. Acad. Sci. USA 88:1711–1715; European Patent Publication No. 318,216.

"HC-J1" and "HC-J4": Okamoto et al. (1991), Japan J. Exp. Med. 60:167–177.

"HCT 18", "HCT 23", "Th", "HCT 27", "EC1" and "EC10": Weiner et al. (1991), Virol. 180:842–848.

"Pt-1", "HCV-K1" and "HCV-K2": Enomoto et al, There are two major types of hepatitis C virus in Japan. Division of Gastroenterology, Department of Internal Medicine, Kanazawa Medical University, Japan.

Clones "A", "C", "D" & "E": Tsukiyama-Kohara et al., A second group of hepatitis virus, in *Virus Genes.*

A typical approach to diagnostic and vaccine strategy is to focus on conserved viral domains. This approach, however, suffers from the disadvantage of ignoring important epitopes that may lie in variable domains.

It is an object of this invention to provide polypeptide compositions that are immunologically cross-reactive with multiple HCV isolates, particularly with respect to heterogeneous domains of the virus.

SUMMARY OF THE INVENTION

It has been discovered that a number of important HCV epitopes vary among viral isolates, and that these epitopes can be mapped to particular domains. This discovery allows for a strategy of producing immunologically cross-reactive polypeptide compositions that focuses on variable (rather than conserved) domains.

Accordingly, one embodiment of the present invention is an immunoreactive composition comprising polypeptides wherein the polypeptides comprise the amino acid sequence of an epitope within a first variable domain of HCV, and at least two heterogeneous amino acid sequences from the first variable domain of distinct HCV isolates are present in the composition.

Another embodiment of the invention is an immunoreactive composition comprising a plurality of antigen sets, wherein (a) each antigen set consists of a plurality of substantially identical polypeptides comprising the amino acid sequence of an epitope within a first variable domain of an HCV isolate, and (b) the amino acid sequence of the epitope of one set is heterogeneous with respect to the amino acid sequence of the analogous sequence of at least one other set.

Another embodiment of the invention is an immunoreactive composition comprising a plurality of polypeptides wherein each polypeptide has the formula

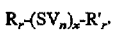

wherein

R and R' are amino acid sequences of about 1–2000 amino acids, and are the same or different;

r and r' are 0 or 1, and are the same or different;

V is an amino acid sequence comprising the sequence of an HCV variable domain, wherein the variable domain comprises at least one epitope;

S in an integer $\geq 1$, representing a selected variable domain; and n is an integer $\geq 1$, representing a selected HCV isolate heterogeneous at a given SV with respect to at least one other isolate having a different value for n, and n being independently selected for each x;

x is an integer $\geq 1$; and with the proviso that amino acid sequences are present in the composition representing a combination selected from the group consisting of (i) $1V_1$ and $1V_2$, (ii) $1V_1$ and $2V_2$, and (iii) $1V_1$ and $2V_1$.

Yet another embodiment of the invention is a method for preparing an immunogenic pharmaceutical composition HCV comprising:

(a) providing an immunoreactive composition as described above;

(b) providing a suitable excipient; and (c) mixing the immunoreactive composition of (a) with the excipient of (b) in a proportion that provides an immunogenic response upon administration to a mammal.

Still another embodiment of the invention is a method for producing anti-HCV antibodies comprising administering to a mammal an effective amount of an immunoreactive composition as described above.

Yet another embodiment of the invention is a method of detecting antibodies to HCV within a biological sample comprising:

(a) providing a biological sample suspected of containing antibodies to HCV;

(b) providing an immunoreactive composition described above;

(c) reacting the biological sample of (a) with the immunoreactive composition of (b) under conditions which allow the formation of antigen-antibody complexes; and (d) detecting the formation of antigen-antibody complexes formed between the immunoreactive composition of (a) and the antibodies of the biological sample of (b), if any.

Another embodiment of the invention is a kit for detecting antibodies to HCV within a biological sample comprising an immunoreactive composition as described above packaged in a suitable container.

BRIEF DESCRIPTION OF THE FIGURES

FIG. 2 shows a comparison of the deduced amino acid sequences of the E1 protein encoded by group I and group II HCV isolates. (SEQ ID NOS:37–45)

FIG. 3 shows a comparison of the amino acid sequences of the putative E2/NS1 region of HCV isolates. (SEQ ID NOS:14–24)

FIG. 8A shows the deduced amino acid sequences of isolates HCV J1.1 and J1.2 from amino acids 384 to 647. (SEQ ID NOS:29–30) FIG. 8B shows the deduced amino acid sequences of isolates HCT27 and HCVE1 from amino acids 384 to 651. (SEQ ID NOS:31–32)

FIG. 9 shows the entire polyprotein sequence of isolate HCV-1. (SEQ ID NO:36)

MODES OF PRACTICING THE INVENTION

The practice of the present invention will employ, unless otherwise indicated, conventional techniques of molecular biology, microbiology, recombinant DNA, and immunology, which are within the skill of the art. Such techniques are explained fully in the literature. See e.g., Maniatis, Fitsch & Sambrook, MOLECULAR CLONING; A LABORATORY MANUAL (2nd ed. 1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986); IMMUNOASSAY: A PRACTICAL GUIDE (D. W. Chan ed. 1987). All patents, patent applications, and publications mentioned herein, both above and below, are incorporated by reference herein.

Figure 1:
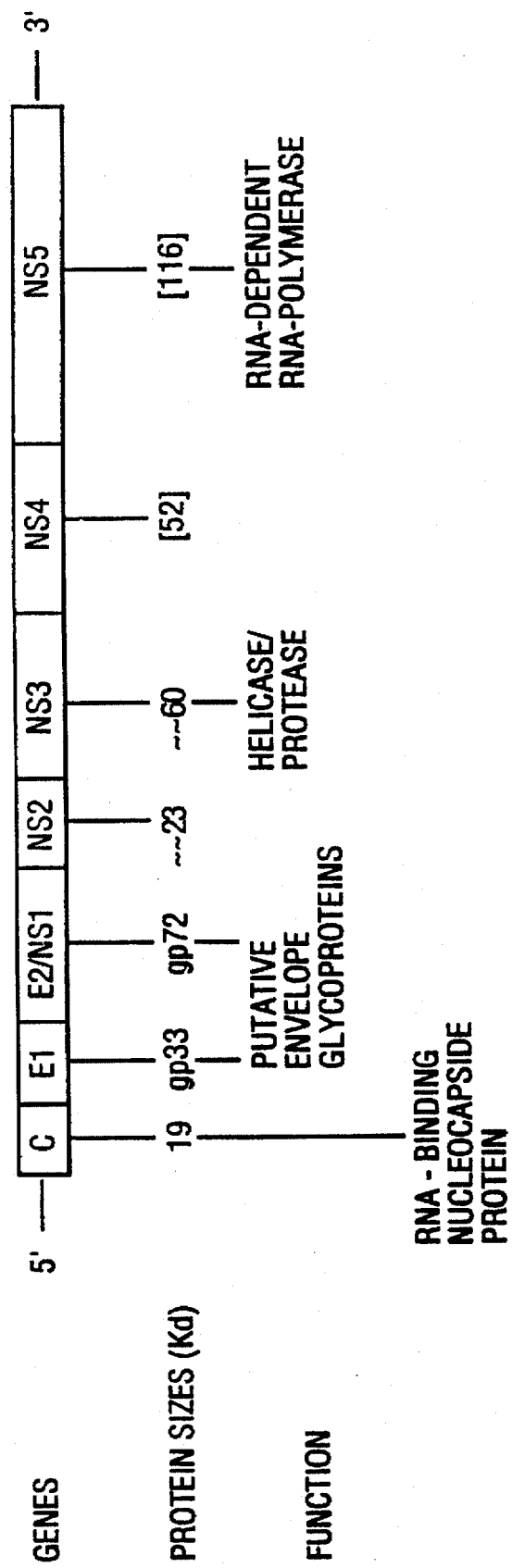
FIG. 1 schematically shows the genetic organization of the HCV genome.

HCV is a new member of the Family Flaviviridae which includes the pestiviruses (Hog Cholera Virus and Bovine Viral Diarrhea Virus) and the Flaviviruses, examples of which are Dengue and Yellow Fever Virus. A scheme of the genetic organization of HCV is shown in FIG. 1. Similar to the flavi- and pestiviruses, HCV appears to encode a basic polypeptide domain ("C") at the N-terminus of the viral polyprotein followed by two glycoprotein domains ("E1", "E2/NS1"), upstream of the nonstructural genes NS2 through NS5. The amino acid coordinates of the putative protein domains are shown in Table 1.

TABLE 1

| The Putative Protein Domains in HCV | |
|---|---|
| a.a. coordinates (approximate) | Protein |
| 1–191 | C |
| 192–383 | E1 |
| 384–750 | E2/NS1 |
| 751–1006 | NS2 |
| 1007–1488 | NS3 |
| 1489–1959 | NS4 |
| 1960–3011 | NS5 |

As discussed above, a number of HCV isolates have been identified. Comparative sequence analysis of complete and partial HCV sequences indicates that based upon homology at the nucleotide and amino acid levels, HCV isolates can be broadly sub-divided into at least three basic groups (Table 2). See Houghton et al., (1991) Hepatology 14:381–388. However, only partial sequence is available for the isolates in group III. Therefore, when the sequences of these isolates are more defined, one or more of these isolates may deserve separation into a different group, including a potential fourth group. Table 3 shows the sequence homologies between individual viral proteins of different HCV isolates as deduced from their nucleotide sequences. It can be seen that the proteins of the same virus group exhibit greater sequence similarity than the same proteins encoded by different virus groups (Table 3). One exception to this is the nucleocapsid protein that is highly conserved among all group I and II viral isolates sequences to date. (In Table 3, the symbol N/A signifies that the sequences were not available for comparison.) For purposes of the present invention, therefore, group I isolates can be defined as those isolates having their viral proteins, particularly E1 and E2/NS1 proteins, about 90% homologous or more at the amino acid level to the isolates classified as group I herein. Group II is defined in an analogous manner. Future groups can likewise be defined in terms of viral protein homology to a prototype isolate. Subgroups can also be defined by homology in limited proteins, such as the E1, E2/NS1 or NS2 proteins, or by simply higher levels of homology.

TABLE 2

Classification of hepatitis C viral genome RNA sequences into three basic groups.

| HCV I | HCV II | HCV III |
|---|---|---|
| HCV-1 | HCV-J1.1 | Clones A, C, D & E |
| HC-J1 | HC-J4 | HCV-K2 (a & b) |
| HCT 18 | HCV-J | |
| HCT 23 | BK | |
| Th | HCV-K1 | |
| HCT 27 | | |
| EC1 | | |
| Pt-1 | | |

TABLE 3

Amino Acid Homologies (%) Between Viral Proteins Encoded by Different HCV Isolates

| HCV Group | C | E1 | E2/NS1 | NS2 | NS3 | NS4 | NS5 |
|---|---|---|---|---|---|---|---|
| I compared to | | | | | | | |
| I | 98–100 | 94–100 | N/A | N/A | N/A | N/A | 99–100 |
| II | 97–98 | 77–79 | 78–81 | 75–77 | 91–92 | 90–93 | 84–88 |
| III | N/A | N/A | N/A | N/A | 86 | 76–80 | 71–74 |
| II compared to | | | | | | | |
| II | 98–100 | 92–100 | 89–100 | 93–100 | 94–100 | 97–100 | 95–100 |
| III | N/A | N/A | N/A | N/A | 84 | 76 | 74–75 |
| III compared to | | | | | | | |
| III | N/A | N/A | N/A | N/A | N/A | 91–100 | 89–100 |

It is noteworthy that the putative viral envelope proteins encoded by the E1 and E2/NS1 genes show substantial amino acid sequence variation between groups I and II. Only NS2 exhibits a greater degree of heterogeneity, while the C, NS3, NS4 and NS5 proteins all show greater sequence conservation between groups. The sequence variation observed in the putative virion envelope proteins between groups I and II reflects a characteristic segregation of amino acids between the two groups. An example of this is shown in FIG. 2 where the sequence of the E1 gene product is compared between viruses of groups I and II. The E1 amino acid sequences deduced from nucleotide sequences of HCV groups II and II are shown. In the figure, the horizontal bars indicate sequence identity with HCV-1. The asterisks indicate group-specific segregation of amino acids; the group-specific residues can be clearly identified. Group I sequences are HCV-1, HCT18, HCT23, HCT27, and HC-J1. Group II sequences are HC-J4, HCV-J, HCV J1.1, and BK. Such group-specific segregation of amino acids is also present in other gene products including gp72 encoded by the E2/NS1 gene. FIG. 3 shows the comparative amino acid sequence of the putative E2/NS1 region of HCV isolates which segregate as group I and group II. The latter protein also contains an N-terminal hypervariable region ("HV") of about 30 amino acids that shows large variation between nearly all isolates. See Weiner et al. (1991), supra., This region occurs between amino acids 384 to 414, Using the amino acid numbering system of HCV-1.

The putative HCV envelope glycoprotein E2/NS1 may correspond to the gp53(BVDV)/gp55 (Hog Cholera Virus) envelope polypeptide of the pestiviruses and the NS1 of the flaviviruses, both of which confer protective immunity in hosts vaccinated with these polypeptides.

Striking similarities between the hypervariable region ("HV") and HIV-1 gp120 V3 domains with respect to degree of sequence variation, the predictive effect of amino acid changes on putative antibody binding in addition to the lack of defined secondary structure suggest that the HV domain encodes neutralizing antibodies.

The immunogenicity of the domain is shown by antibody epitope mapping experiments, described in the Examples. The results of these studies suggest that in addition to the three major groups of HCV, HV specific sub-groups also exist.

Analysis of biological samples from individuals with HCV induced NANBH indicate that individuals may be carrying two or more HCV variants simultaneously. Two co-existing HV variants were found in the plasma of one individual, J1. In addition, partial sequencing of the gene of an individual with chronic NANBH, who had intermittent flares of hepatitis, revealed that the individual, Q, was infected with two HCV variants (Q1 or Q3). Each variant was associated with only one episode of the disease. An ELISA using a Q1 or Q3 specific peptide (amino acids 396–407) showed that Q developed an antibody response to the Q1 peptide but not the corresponding Q3 peptide, suggesting that Q's recrudescence of disease was due to the appearance of an HV variant. The presence of antibodies to the Q1 peptide but lack of humoral immune response to the Q3 peptide during the second episode of disease suggest that variation in the HV domain may result from the pressure of immune selection. Amino acids 396–407 appear to be subject to the greatest selective pressure in the HV domain. These findings support the thesis that high levels of chronicity associated with the disease might be due to an inadequate immunological host response to HCV infection and/or effective viral mechanisms of immunological evasion. Moreover, they point to the E2/NS1 HV region as a genetic region involved in a viral escape mechanism and/or an inadequate immunological response mechanism(s).

As discussed above, there are several variant regions within the HCV genome. One or more of these regions are most likely involved in a viral escape mechanism and/or an inadequate immunological response mechanism. Therefore, it is desirable to include in compositions for treatment of HCV polypeptides which would induce an immunogenic response to these variants.

In that the E1 and E2/NS1 regions of the genome encode putative envelope type polypeptides, these regions would be of particular interest with respect to immunogenicity. Thus, these regions are amongst those to which it would be particularly desirable to induce and/or increase an immune response to protect an individual against HCV infection, and to aid in the prevention of chronic recurrence of the disease in infected individuals. In addition, these regions would be amongst those from which it would be desirable to detect HCV variants which are arising during the course of infection, as well as super- or co-infection by two or more variants.

The present invention describes compositions and methods for treating individuals to prevent HCV infections, and particularly chronic HCV infections. In addition, it describes compositions and methods for detecting the presence of anti-HCV antibodies in biological samples. This latter method is particularly useful in identifying anti-HCV antibodies generated in response to immunologically distinct HCV epitopes. This method can also be used to study the evolution of multiple variants of HCV within an infected individual. In the discussion of the invention, the following definitions are applicable.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring.

As used herein, A is "substantially isolated" from B when the weight of A is at least about 70%, more preferably at least about 80%, and most preferably at least about 90% of the combined weights of A and B. The polypeptide compositions of the present invention are preferably substantially free of human or other primate tissue (including blood, serum, cell lysate, cell organelles, cellular proteins, etc.) and cell culture medium.

A "recombinant polynucleotide" intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, etc.), those containing alkylators, those with modified linkages (e.g., alpha anomeric nucleic acids, etc.), as well as unmodified forms of the polynucleotide.

"Recombinant host cells", "host cells", "cells", "cell lines", "cell cultures", and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc., that behaves as an autonomous unit of polynucleotide replication within a cell; i.e., capable of replication under its own control.

A "vector" is a replicon further comprising sequences providing replication and/or expression of the open reading frame.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences which govern secretion.

A "promoter" is a nucleotide sequence which is comprised of consensus sequences which allow the binding of RNA polymerase to the DNA template in a manner such that mRNA production initiates at the normal transcription initiation site for the adjacent structural gene.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

As used herein, "epitope" or "antigenic determinant" means an amino acid sequence that is immunoreactive. Generally an epitope consists of at least 3 to 5 amino acids, and more usually, consists of at least about 8, or even about 10 amino acids. As used herein, an epitope of a designated polypeptide denotes epitopes with the same amino acid sequence as the epitope in the designated polypeptide, and immunologic equivalents thereof.

An "antigen" is a polypeptide containing one or more epitopes.

"Immunogenic" means the ability to elicit a cellular and/or humoral immune response. An immunogenic response may be elicited by immunoreactive polypeptides alone, or may require the presence of a carrier in the presence or absence of an adjuvant.

"Immunoreactive" refers to (1) the ability to bind immunologically to an antibody and/or to a lymphocyte antigen receptor or (2) the ability to be immunogenic.

An "antibody" is any immunoglobulin, including antibodies and fragments thereof, that binds a specific epitope.

The term encompasses, inter alia, polyclonal, monoclonal, and chimeric antibodies. Examples of chimeric antibodies are discussed in U.S. Pat. Nos. 4,816,397 and 4,816,567.

An "antigen set" is defined as a composition consisting of a plurality of substantially identical polypeptides, wherein the polypeptides are comprised of an amino acid sequence of one defined epitope.

"Substantially identical polypeptides" means polypeptides that are identical with the exception of variation limited to the typical range of sequence or size variation attributable to the polypeptide's method of production; e.g., recombinant expression, chemical synthesis, tissue culture, etc. This variation does not alter the desired functional property of a composition of substantially identical polypeptides; e.g., the composition behaves immunologically as a composition of identical polypeptides. The variations may be due to, for example, alterations resulting from the secretory process during transport of the polypeptide, less than 100% efficiency in chemical synthesis, etc.

As used herein, a "variable domain" or "VD" of a viral protein is a domain that demonstrates a consistent pattern of amino acid variation between at least two HCV isolates or subpopulations. Preferably, the domain contains at least one epitope. Variable domains can vary from isolate to isolate by as little as 1 amino acid change. These isolates can be from the same or different HCV group(s) or subgroup(s). Variable domains can be readily identified through sequence composition among isolates, and examples of these techniques are described below. For the purposes of describing the present invention, variable domains will be defined with respect to the amino acid number of the polyprotein encoded by the genome of HCV-1 as shown in FIG. 9, with the initiator methionine being designated position 1. The corresponding variable domain in another HCV isolate is determined by aligning the two isolates sequences in a manner the brings the conserved domains outside any variable domain into maximum alignment. This can be performed with any of a number of computer software packages, such as ALIGN 1.0, available from the University of Virginia, Department of Biochemistry (Attn: Dr. William R. Pearson). See Pearson et al., (1988) Proc. Natl. Acad. Sci. USA 85:2444–2448. It is to be understood that the amino acid numbers given for a particular variable domain are somewhat subjective and a matter of choice. Thus, the beginning and end of variable domains should be understood to be approximate and to include overlapping domains or subdomains, unless otherwise indicated.

An epitope is the "immunologic equivalent" of another epitope in a designated polypeptide when it cross-reacts with antibodies which bind immunologically to the epitope in the designated polypeptide.

Epitopes typically are mapped to comprise at least about five amino acids, sometimes at least about 8 amino acids, and even about 10 or more amino acids.

The amino acid sequence comprising the HCV epitope may be linked to another polypeptide (e.g., a carrier protein), either by covalent attachment or by expressing a fused polynucleotide to form a fusion protein. If desired, one may insert or attach multiple repeats of the epitope, and/or incorporate a variety of epitopes. The carrier protein may be derived from any source, but will generally be a relatively large, immunogenic protein such as BSA, KLH, or the like. If desired, one may employ a substantially full-length HCV protein as the carrier, multiplying the number of immunogenic epitopes. Alternatively, the amino acid sequence from the HCV epitope may be linked at the amino terminus and/or carboxy terminus to a non-HCV amino acid sequence, thus the polypeptide would be a "fusion polypeptide". Analogous types of polypeptides may be constructed using epitopes from other designated viral proteins.

A "variant" of a designated polypeptide refers to a polypeptide in which the amino acid sequence of the designated polypeptide has been altered by the deletion, substitution, addition or rearrangement of one or more amino acids in the sequence. Methods by which variants occur (for example, by recombination) or are made (for example, by site directed mutagenesis) are known in the art.

"Transformation" refers to the insertion of an exogenous polynucleotide into a host cell, irrespective of the method used for the insertion, for example, direct uptake, transduction (including viral infection), f-mating or electroporation. The exogenous polynucleotide may be maintained as a non-integrated vector, for example, a plasmid or viral genome, or alternatively, may be integrated into the host genome.

An "individual" refers to a vertebrate, particularly a member of a mammalian species, and includes but is not limited to rodents (e.g., mice, rats, hamsters, guinea pigs), rabbits, goats, pigs, cattle, sheep, and primates (e.g., chimpanzees, African Green Monkeys, baboons, orangutans, and humans).

As used herein, "treatment" refers to any of (i) the prevention of infection or reinfection, as in a traditional vaccine, (ii) the reduction or elimination of symptoms, and (iii) the substantial or complete elimination of the virus. Treatment may be effected prophylactically (prior to infection) or therapeutically (following infection).

The term "effective amount" refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary from application. For vaccine applications or in the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, biopsies and also samples of in vitro cell culture constituents (including but not limited to conditioned medium resulting from the growth of cells in cell culture medium, e.g., Mab producing myeloma cells, recombinant cells, and cell components).

The immunoreactive polypeptide compositions of the present invention comprise a mixture of isolate- or group-specific epitopes from at least one HCV VD. Thus, there will be present at least two heterogeneous amino acid sequences each defining an epitope found in distinct HCV isolates located in the same or substantially same physical location in an HCV protein; i.e. each sequence maps to the same location within the HCV genome/polypeptide. Since the sequences are heterogeneous, the location is referred to as a variable domain (VD).

To better understand the invention, first the individual amino acid sequences that make up the compositions of the invention will be explained. Then the plurality of such sequences which are found in the compositions of the present invention will be discussed.

The amino acid sequence that characterizes the polypeptides of the present invention have a basic structure as follows:

$$L_y\text{-}Z\text{-}L'_{y'} \quad \quad \text{(I)}$$

Z represents the amino acid sequence from a region of a protein from a selected HCV isolate, where the region comprises at least one variable domain and the variable domain comprises at least one epitope. L and L' are non-HCV amino acid sequences or HCV amino acid sequences that do not contain a variable domain, and which can be the same or different. y and y' are 0 or 1 and can be the same or different. Thus, formula I represents an amino acid sequence comprising the sequence of an HCV VD, wherein the VD comprises an epitope.

As discussed above, the epitope(s) in Z will usually comprise a minimum of about 5 amino acids, more typically a minimum of about 8 amino acids, and even more typically a minimum of about 10 amino acids.

The variable domain of Z can comprise more than one epitope. The variable domain of Z is at least as big as the combined sequences of the epitopes present, thus making it typically a minimum of about 5 amino acids when a single epitope is present. Since epitopes can overlap, the minimum amino acid sequence for combined epitopes in the variable domain may be less than the sum of the individual epitopes' sequences.

Z is the amino acid sequence of an HCV isolate comprising the above-described VD. Thus, the minimum size of Z is the minimum size of the VD. Z can comprise more HCV amino acid sequence than just the VD, and can further comprise more than one VD. The maximum size of Z is not critical, but obviously cannot exceed the length of the entire HCV polyprotein. Typically, however, Z will be the sequence of an entire HCV protein (particularly E1, E2/NS1, NS2, NS3, NS4 and NS5) or, even more typically, a fragment of such an HCV protein. Thus, Z will preferably range from a minimum of about 5 amino acids (more preferably about 8 or about 10 amino acids minimum) to a maximum of about 1100 amino acids (more preferably a maximum of about 500, more preferably a maximum of about 400 or even more preferably a maximum of about 200 amino acids maximum). More usually, the polypeptide of formula I and/or Z, when prepared by, e.g., chemical synthesis, is a maximum of about 50 amino acids, more typically a maximum of about 40 amino acids, and even more typically a maximum of about 30 amino acids.

The non-HCV amino acid sequences, L and L', if present, can constitute any of a number types of such sequences. For example, L and L' can represent non-HCV sequences to which Z is fused to facilitate recombinant expression (e.g., beta-galactosidase, superoxide dismutase, invertase, alpha-factor, TPA leader, etc.), as discussed below. Alternatively, L and L' can represent epitopes of other pathogens, such as hepatitis B virus, *Bordetella pertussis*, tetanus toxoid, diphtheria, etc., to provide compositions that are immunoreactive relative to a number these other pathogens. L and L' can be amino acid sequences that facilitate attachment to solid supports during peptide synthesis, immunoassay supports, vaccine carrier proteins, etc. In fact, L and L' can even comprise one or more superfluous amino acids with no functional advantage. There is no critical maximum size for L or L', the length being generally governed by the desired function. Typically, L and L' will each be a maximum of about 2000 amino acids, more typically a maximum of about 1000 amino acids. The majority of L and L' sequences with useful properties will be a maximum of about 500 amino acids. It is desirable, of course, to select L and L' so as to not block the immunoreactivity of Z.

The composition of polypeptides provided according to the present invention are characterized by the presence (in an effective amount for immunoreactivity) within the composition of at least two amino acid sequences defined as follows by formulas II and III, respectively:

$$L_y\text{-}Z_1\text{-}L'_{y'} \quad \quad \text{(II)}$$

$$L_y\text{-}Z_2\text{-}L'_{y'} \quad \quad \text{(III)}$$

L, L', y and y' are defined as above, as well as independently defined for each of formulas II and III. $Z_1$ and $Z_2$ are each HCV amino acid sequences as defined for Z above encompassing the same variable domain (i.e., physical location), but derived from different HCV isolates having between them at least one heterogeneous epitope in the common variable domain of $Z_1$ and $Z_2$. As an illustrative example, an amino acid sequence according to formula II could have as $Z_1$ a fragment the hypervariable domain spanning amino acids 384–414 of isolate HCV-1 (or more particularly 396–407 or 396–408), while $Z_2$ is the analogous fragment from isolate HCV-J1.1. These two isolates are heterogeneous in this domain, the amino acid sequences of the epitopes varying significantly.

It is to be understood that the compositions of the present invention may comprise more than just two discrete amino acid sequences according to formula I, and that the Z sequences may be divided into groups encompassing different variable domains. For example, a composition according to the present invention could comprise a group of HCV sequences (with amino acid sequences according to formula I) encompassing the hypervariable domain at amino acids 384–411 from isolates HCV-1, HCV-J1.1, HC-J1, HC-J4, etc. The composition could also comprise an additional group of HCV sequences (within amino acid sequences according to formula I) encompassing the variable domain at amino acids 215–255 also from isolates HCV-1, HCV-J1.1, HC-J1, HC-J4, etc. Within the context of the compositions of the present invention, therefore, the sequence of formula I can be further defined as follows:

$$sV_n \quad \quad \text{(IV)}$$

V represents an amino acid sequence comprising the sequence of an HCV variable domain, wherein the variable domain comprises at least one epitope; i.e., formula I. S and n are integers of 1 or greater. S represents a particular variable domain, and n represents a particular isolate. For example, S=1 could represent the variable domain at amino acids 384–411; S=2 could represent the variable domain at amino acids 215–255; and n=1, 2, 3 and 4 could represent isolates HCV-1, HCV-J1.1, HC-J1 and HC-J4, respectively. Thus, the two groups of sequences discussed above could be represented by:

Group 1: $1V_1$, $1V_2$, $1V_3$ & $1V_4$

Group 2: $2V_1$, $2V_2$, $2V_3$ & $2V_4$

There are at least two distinct sequences of formula IV in the compositions according to the present invention; i.e., the composition contains two different sequences according to formula IV where the values for S and or n are different. For example, at least $1V_1$ and $1V_2$ are present, or at least $1V_1$ and $2V_2$ are present, or at least $1V_1$ and $2V_1$ are present.

The distinct sequences falling within formula IV are present in the composition either on the same or different polypeptide molecules. Using the minimum combination of $1V_1$ and $1V_2$ to illustrate, these two sequences could be present in the same polypeptide molecule (e.g., $1V_1$–$1V_2$) or in separate molecules. This feature of the compositions of the present invention can be described as compositions of polypeptides as follows:

$$R_r\text{-}(SV_n)_x\text{-}R'_{r'} \qquad (V)$$

wherein S, V and n are as defined above; R and R' are amino acid sequences of about 1–2000 amino acids, and are the same or different; r and r' are 0 or 1, and are the same or different; x is an integer $\geq 1$; n is independently selected for each x; and with the proviso that amino acid sequences are present in the composition representing a combination selected from the group consisting of (i) $1V_1$ and $1V_2$, (ii) $1V_1$ and $2V_2$, and (iii) $1V_1$ and $2V_1$. In embodiments where the distinct sequences of formula IV are in different polypeptides, x can be 1, although it can still be >1 if desired; e.g., a mixture of polypeptides $1V_1$–$1V_2$ and $1V_1$–$2V_2$. When x is 1, r and r' are preferably both 0 to avoid redundancy with $L_y$ and $L'_{y'}$, since V can be described by in a preferred embodiment by formula I. When x is >1, the combined lengths of R and the adjacent L, and of R' and the adjacent L', are preferably no more than the typical maximum lengths described above for L and L'.

The selection of the HCV amino acid sequences included within the distinct V sequences of the compositions will depend upon the intended application of the sequences and is within the skill of the art in view of the present disclosure. First, it should be appreciated that the HCV epitopes of concern to the present invention can be broken down into two types. The first type of epitopes are those that are "group-specific"; i.e., the corresponding epitopes in all or substantially all isolates within an HCV isolate group are immunologically cross-reactive with each other, but not with the corresponding epitopes of substantially all the isolates of another group. Preferably, the epitopes in a group-specific class are substantially conserved within the group, but not between or among the groups. The second type of epitopes are those that are "isolate-specific"; i.e., the epitope is immunologically cross-reactive with substantially identical isolates, and is not cross-reactive with all or substantially all distinct isolates.

These group- and isolate-specific epitopes can be readily identified in view of the present disclosure. First, the sequences of several HCV isolates is compared, as described herein, and areas of sequence heterogeneity identified. The pattern of heterogeneity usually indicates group or isolate specificity. If an identified area is known to comprise one or more epitopes, then a sequence of sufficient size to include the desired epitope(s) is selected to as an variable domain that may be included in the compositions of the present invention. If the immunoreactivity of a given heterogeneous area is not known, peptides representing the sequences found in that area of the various HCV isolates can be prepared and screened. Screening can include, but is not limited too, immunoassays with various sources of anti-HCV antibody (e.g., patient serum, neutralizing Mabs, etc.) or generation of antibody and testing the ability of such antibody to neutralize virus in vitro. Alternatively, the loci of epitopes identified in a screening protocol, such as that described below, can be examined for heterogeneity among various isolates and the immunological properties of corresponding heterogeneous sequences screened.

For vaccine applications, it is believed that variable domains from the E1 and/or E2/NS1 domains will be of particular interest. In particular, an E1 variable domain within amino acids 215–255 (see FIG. 2), and an E2/NS1 variable domain within amino acids 384–414 (see FIG. 3), have been identified as being important immunoreactive domains. The preliminary evidence suggests that one or both of these domains may be loci of heterogeneity responsible for escape mutants, leading to chronic HCV infections. Thus, polypeptide compositions as described above where the variable domain(s) in V are one or both of these variable domains are particularly preferred. Furthermore, the polypeptide compositions of the present invention, while particularly concerned with the generally linear epitopes in the variable domains, may also include conformational epitopes. For example, the composition can be comprised of a mixture of recombinant E1 and/or E2/NS1 proteins (exhibiting the variable domains of different isolates) expressed in a recombinant system (e.g., insect or mammalian cells) that maintains conformational epitopes either inside or outside the variable domain. Alternatively, an E1 and/or E2/NS1 subunit antigen from a single isolate that maintains conformational epitopes can be combined with a polypeptide composition according to the present invention (e.g., a mixture of synthetic polypeptides or denatured recombinant polypeptides). In another preferred application for vaccines, the polypeptide compositions described herein are combined with other HCV subunit antigens, such as those described in commonly owned U.S. Ser. No. 07/758880, entitled "Hepatitis C Virus Asialoglycoproteins" (Attorney Docket No. 0154.002) by Robert O. Ralston, Frank Marcus, Kent B. Thudium, Barbara Gervase, and John Hall, filed on even date herewith, and incorporated herein by reference.

For diagnostic application, it may be useful to employ the compositions of the present invention as antigens, thereby improving the ability to detect antibody to distinct HCV isolates. Typically the polypeptide mixtures can used directly in a homogeneous or heterogeneous immunoassay format, the latter preferably comprising immobilizing the polypeptide on a solid substrate (e.g., microtiter plate wells, plastic beads, nitrocellulose, etc.). See, e.g., PCT Pub. No. WO90/11089; EPO Pub. No. 360,088; IMMUNOASSAY: A PRACTICAL GUIDE, supra. Alternatively, each substantially identical polypeptide that makes up the polypeptide composition of the present invention could be immobilized on the same support at discrete loci, thereby providing information as to which isolate or group the antibody has been generated. This may be particularly important in diagnostics if various isolates cause hepatitis, cancer or other diseases with different clinical prognoses. A preferred format is the Chiron RIBA™ strip immunoassay format, described in commonly owned U.S. Ser. No. 07/138,894 and U.S. Ser. No. 07/456,637, the disclosures of which are incorporated herein by reference.

Polypeptides useful in the manufacture of the compositions of the present invention can be made recombinantly, synthetically or in tissue culture. Recombinant polypeptides comprised of the truncated HCV sequences or full-length HCV proteins can be made up entirely of HCV sequences (one or more epitopes, either contiguous or noncontiguous), or sequences in a fusion protein. In fusion proteins, useful heterologous sequences include sequences that provide for secretion from a recombinant host, enhance the immunological reactivity of the HCV epitope(s), or facilitate the coupling of the polypeptide to a support or a vaccine carrier. See, e.g., EPO Pub. No. 116,201; U.S. Pat. No. 4,722840; EPO Pub. No. 259,149; U.S. Pat. No. 4,629,783, the disclosures of which are incorporated herein by reference.

Full length as well as polypeptides comprised of truncated HCV sequences, and mutants thereof, may be prepared by chemical synthesis. Methods of preparing polypeptides by chemical synthesis are known in the art. They may also be prepared by recombinant technology. A DNA sequence encoding HCV-1, as well as DNA sequences of variable regions from other HCV isolates have been described and/or referenced herein. The availability of these sequences permits the construction of polynucleotides encoding immunoreactive regions of HCV polypeptides.

Polynucleotides encoding the desired polypeptide comprised of one or more of the immunoreactive HCV epitope from a variable domain of HCV may be chemically synthesized or isolated, and inserted into an expression vector. The vectors may or may not contain portions of fusion sequences such as beta-Galactosidase or superoxide dismutase (SOD). Methods and vectors which are useful for the production of polypeptides which contain fusion sequences of SOD are described in European Patent Office Publication number 0196056, published Oct. 1, 1986.

The DNA encoding the desired polypeptide, whether in fused or mature form and whether or not containing a signal sequence to permit secretion, may be ligated into expression vectors suitable for any convenient host. The hosts are then transformed with the expression vector. Both eukaryotic and prokaryotic host systems are presently used in forming recombinant polypeptides, and a summary of some of the more common control systems and host cell lines is presented infra. The host cells are incubated under conditions which allow expression of the desired polypeptide. The polypeptide is then isolated from lysed cells or from the culture medium and purified to the extent needed for its intended use.

The general techniques used in extracting the HCV genome from a virus, preparing and probing DNA libraries, sequencing clones, constructing expression vectors, transforming cells, performing immunological assays such as radioimmunoassays and ELISA assays, for growing cells in culture, and the like, are known in the art. (See, e.g., the references cited in the "Background" section, above, as well as the references cited at the beginning of this ("Modes of Practicing the Invention" section above.

Transformation of the vector containing the desired sequence into the appropriate host may be by any known method for introducing polynucleotides into a host cell, including, for example, packaging the polynucleotide in a virus and transducing the host cell with the virus, or by direct uptake of the polynucleotide. The transformation procedure used depends upon the host to be transformed. Bacterial transformation by direct uptake generally employs treatment with calcium or rubidium chloride (Cohen (1972), Proc. Natl. Acad. Sci. USA 69:2110. Yeast transformation by direct uptake may be carried out using the method of Hinnen et al. (1978), J. Adv. Enzyme Reg.7:1929. Mammalian transformations by direct uptake may be conducted using the calcium phosphate precipitation method of Graham and Van der Eb (1978), Virology 52:546, or the various known modifications thereof. Other methods for the introduction of recombinant polynucleotides into cells, particularly into mammalian cells, which are known in the art include dextran mediated transfection, calcium phosphate mediated transfection, polybrene mediated transfection, protoplast fusion, electroporation, encapsulation of the polynucleotide(s) in liposomes, and direct microinjection of the polynucleotides into nuclei.

In order to obtain expression of desired coding sequences, host cells are transformed with polynucleotides (which may be expression vectors), which are comprised of control sequences operably linked to the desired coding sequences. The control sequences are compatible with the designated host. Among prokaryotic hosts, $E.$ $coli$ is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. Promoter sequences may be naturally occurring, for example, the $\beta$-lactamase (penicillinase) (Weissman (1981), "The cloning of interferon and other mistakes" in $Interferon$ 3 (ed. I. Gresser), lactose (lac) (Chang et al. (1977), Nature 198:1056) and tryptophan (trp) (Goeddel et al. (1980), Nucl. Acids Res. 8:4057), and lambda-derived $P_L$ promoter system and N gene ribosome binding site (Shimatake et al. (1981), Nature 292:128). In addition, synthetic promoters which do not occur in nature also function as bacterial promoters. For example, transcription activation sequences of one promoter may be joined with the operon sequences of another promoter, creating a synthetic hybrid promoter (e.g., the tac promoter, which is derived from sequences of the trp and lac promoters (De Boer et al. (1983), Proc. Natl. Acad. Sci. USA 80:21). The foregoing systems are particularly compatible with $E.$ $coli$; if desired, other prokaryotic hosts such as strains of Bacillus or Pseudomonas may be used, with corresponding control sequences.

Eukaryotic hosts include yeast and mammalian cells in culture systems. $Saccharomyces$ $cerevisiae$ and $Saccharomyces$ $carlsbergensis$ are the most commonly used yeast hosts, and are convenient fungal hosts. Yeast compatible vectors generally carry markers which permit selection of successful transformants by conferring prototropy to auxotrophic mutants or resistance to heavy metals on wild-type strains. Yeast compatible vectors may employ the 2 micron origin of replication (Broach et al. (1983), Meth. Enz. 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al. (1968), J. Adv. Enzyme Reg. 7:149); for example, alcohol dehydrogenase (ADH) (E.P.O. Publication No. 284044), enolase, glucokinase, glucose-6-phosphate isomerase, glyceraldehyde-3-phosphate dehydrogenase (GAP or GAPDH), hexokinase, phosphofructokinase, 3-glycerophosphate mutase, and pyruvate kinase (PyK) (E.P.O. Publication No. 329203). The yeast PHO5 gene, encoding acid phosphatase, also provides useful promoter sequences. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, or PEO5 genes, combined with the transcriptional activation region of a glycolytic enzyme gene such as GAP or PyK (E.P.O. Publication No. 164556). Furthermore, a yeast promoter can include naturally occurring promoters of non-yeast origin that have the ability to bind yeast RNA polymerase for the appropriate initiation of transcription.

Other control elements which may be included in the yeast expression vector are terminators (e.g., from GAPDH, and from the enolase gene (Holland (1981), J. Biol. Chem. 256:1385), and leader sequences. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (E.P.O. Publication No. 12,873) and the α-factor gene (U.S. Pat. No. 4,588,684). Alternatively, leaders of non-yeast origin, such as an interferon leader, also provide for secretion in yeast (E.P.O. Publication No. 60057). A preferred class of secretion leaders are those that employ a fragment of the yeast α-factor gene, which contains both a "pre" signal sequence, and a "pro" region. The types of α-factor fragments that can be employed include the full-length pre-pro α-factor leader, as well as truncated α-factor leaders (U.S. Pat. Nos. 4,546,083 and 4,870,008; E.P.O. Publication No. 324274. Additional leaders employing an α-factor leader fragment that provides for secretion include hybrid α-factor leaders made with a pre-sequence of a first yeast, but a pro-region from a second yeast α-factor. (See, e.g., P.C.T. WO 89/02463).

Expression vectors, either extrachromosomal replicons or integrating vectors, have been developed for transformation into many yeasts. For example, expression vectors have been developed for *Candida albicans* (Kurtz et al. (1986), Mol. Cell Biol. 6:142), *Candida maltosa* (Kunze et al. (1985) J. Basic Microbiol. 25:141), *Hanzenula polymorpha* (Gleeson et al. (1986), J. Gen. Microbiol. 132:3459), *Kluyveromyces fragilis* (Das et al. (1984), J. Bacteriol. 158:1165), *Kluyveromyces lactis* (De Louvencourt et al. (1983), J. Bacteriol. 154:737), *Pichia guillerimondii*, (Kunze et al. (1985), supra), *Pichia pastoris* (Cregg et al. (1985), Mol. Cell. Biol. 5:3376; U.S. Pat. Nos. 4,837,148 and 4,929,555)), *Schizosaccharomyces pombe* (Beach and Nurse (1981), Nature 300:706), and *Yarrowia lipolytica* (Davidow et al. (1985), Curt. Genet. 10:39).

Mammalian cell lines available as hosts for expression are known in the art and include many immortalized cell lines available from the American Type Culture Collection (ATCC), including, for example, HeLa cells, Chinese hamster ovary (CHO) cells, baby hamster kidney (BHK) cells, COS monkey cells, and a number of other cell lines. Suitable promoters for mammalian cells are also known in the art and include viral promoters such as that from Simian Virus 40 (SV40), Rous sarcoma virus (RSV), adenovirus (ADV) and bovine papilloma virus (BPV) (See, Sambrook (1989) for examples of suitable promoters). Mammalian cells may also require terminator sequences and poly A addition sequences; enhancer sequences which increase expression may also be included, and sequences which cause amplification of the gene may also be desirable. These sequences are known in the art.

Vectors suitable for replication in mammalian cells are known in the art, and may include viral replicons, or sequences which ensure integration of the appropriate sequences encoding the desired polypeptides into the host genome.

A vector which is used to express foreign DNA and which may be used in vaccine preparation is Vaccinia virus. In this case, the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett et al (1984) in "DNA Cloning", Vol. II. IRL Press, p.191, Chakrabarti et al. (1985), Mol. Cell Biol. 5:3403; Moss (1987) in "Gene Transfer Vectors for Mammalian Cells" (Miller and Calos, eds., p. 10). Expression of the desired polypeptides comprised of immunoreactive regions then occurs in cells or individuals which are infected and/or immunized with the live recombinant vaccinia virus.

Other systems for expression of polypeptides include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedron gene promoter to drive expression of heterologous genes. Currently the most commonly used transfer vector for introducing foreign genes into AcNPV is pac373. Many other vectors, known to those of skill in the art, have also been designed for improved expression. These include, for example, pVL985 (which alters the polyhedron start codon from ATG to ATT, and which introduces a BamHI cloning site 32 basepairs downstream from the ATT; See Luckow and Summers (1989), Virology 17:31. Good expression of nonfused foreign proteins usually requires foreign genes that ideally have a short leader sequence containing suitable translation initiation signals preceding an ATG start signal. The plasmid also contains the polyhedron polyadenylation signal and the ampicillin-resistance (amp) gene and origin of replication for selection and propagation in *E. coli.*

Methods for the introduction of heterologous DNA into the desired site in the baculovirus are known in the art. (See Summers and Smith, Texas Agricultural Experiment Station Bulletin No. 1555; Ju et al. (1987), in "Gene Transfer Vectors for Mammalian Cells (Miller and Calos, eds.); Smith et al. (1983), Mol. & Cell. Biol. 3:2156; and Luckow and Summers (1989), supra). For example, the insertion can be into a gene such as the polyhedron gene, by homologous recombination; insertion can also be into a restriction enzyme site engineered into the desired baculovirus gene. The inserted sequences may be those which encode all or varying segments of the desired HCV polypeptides including at least one epitope from a variable domain.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate and vertebrate cells. Examples of the signal sequences from vertebrate cells which are effective in invertebrate cells are known in the art, for example, the human interleukin 2 signal ($IL2_s$) which is a signal for transport out if the cell, is recognized and properly removed in insect cells.

It is often desirable that the polypeptides prepared using the above host cells and vectors be fusion polypeptides. As with non-fusion polypeptides, fusion polypeptides may remain intracellular after expression. Alternatively, fusion proteins can also be secreted from the cell into the growth medium if they are comprised of a leader sequence fragment. Preferably, there are processing sites between the leader fragment and the remainder of the foreign gene that can be cleaved either in vivo or in vitro.

In cases where the composition is to be used for treatment of HCV, it is desirable that the composition be immunogenic. In instances wherein the synthesized polypeptide is correctly configured so as to provide the correct epitope, but is too small to be immunogenic, the polypeptide may be linked to a suitable carrier. A number of techniques for obtaining such linkage are known in the art, including the formation of disulfide linkages using N-succinimidyl-3-(2-pyridylthio)propionate (SPDP) and succinimidyl 4-(N-maleimidomethyl)cyclohexane-1-carboxylate (SMCC) (if the peptide lacks a sulfhydryl group, this can be provided by addition of a cysteine residue.) These reagents create a disulfide linkage between themselves and peptide cysteine resides on one protein and an amide linkage through the ε-amino on a lysine, or other free amino group in other amino acids. A variety of such disulfide/amide-forming agents are known. See, for example, Immun. Rev. (1982) 62:185. Other bifunctional coupling agents for a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl) cyclohexane-1-carboxylic acid, and the like. The carboxyl groups can be activated by combining them with succinimide or 1-hydroxyl-2-nitro-4-sulfonic acid, sodium salt. Additional methods of coupling antigens employ the rotavirus/"binding peptide" system described in EPO Publication No. 259,149. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides such as latex functionalized sepharose, agarose, cellulose, cellulose beads and the like; polymeric amino acids, such as polyglutamic acid, polylysine, and the like; amino acid copolymers; and inactive virus particles (see infra.). Especially useful protein substrates are serum albumins, keyhole limpet hemocyanin, immunoglobulin molecules, thyroglobulin, ovalbumin, tetanus toxoid, and other proteins well known to those of skill in the art.

The immunogenicity of the epitopes of the HCV variable domains, particularly of E1 and E2/NS1, may also be enhanced by preparing them in eukaryotic systems fused with or assembled with particle-forming proteins such as, for example, that associated with hepatitis B surface antigen. See, e.g., U.S. Pat. No. 4,722,840. Constructs wherein the polypeptide containing the HCV epitope from a variable domain is linked directly to the particle-forming protein coding sequences produces hybrids which are immunogenic with respect to the HCV epitope. In addition, all of the vectors prepared include epitopes specific to HBV, having various degrees of immunogenicity, such as, for example, the pre-S peptide. Thus, particles constructed from particle forming protein which include HCV sequences are immunogenic with respect to HCV and HBV.

Hepatitis surface antigen (HBSAg) has been shown to be formed and assembled into particles in *S. cerevisiae* (Valenzuela et al. (1982), Nature 298:344, as well as in, for example, mammalian cells (Valenzuela et al. (1984), in "Hepatitis B", Millman I. et al., ed.). The formation of such particles has been shown to enhance the immunogenicity of the monomer subunit. The constructs may also include the immunodominant epitope of HBSAg, comprising the 55 amino acids of the presurface (pre-S) region. Neurath et al. (1984). Constructs of the pre-S-HBSAg particle expressible in yeast are disclosed in E.P.O. Publication No. 174,444; hybrids including heterologous viral sequences for yeast expression are disclosed in E.P.O. Publication No. 175,261. These constructs may also be expressed in mammalian cells such as CHO cells using an SV40-dihydrofolate reductase vector (Michelle et al. (1984)).

In addition, portions of the particle-forming protein coding sequence may be replaced with codons encoding an epitope from an HCV variable domain. In this replacement, regions which are not required to mediate the aggregation of the units to form immunogenic particles in yeast or mammals can be deleted, thus eliminating additional HBV antigenic sites from competition with the HCV epitope(s).

The preparation of vaccines which contain an immunogenic polypeptide(s) as an active ingredient(s) is known to one skilled in the art. Typically, such vaccines are prepared as injectables, either as liquid solutions or suspensions; solid forms suitable for solution in, or suspension in, liquid prior to injection may also be prepared. the preparation may also be emulsified, or the polypeptide(s) encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include, but are not limited to: aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE, and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an HCV epitope from a variable domain, the antibodies resulting from administration of this polypeptide in vaccines which are also comprised of the various adjuvants.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

In addition to the above, it is also possible to prepare live vaccines of attenuated microorganisms which express recombinant polypeptides of the HCV antigen sets. Suitable attenuated microorganisms are known in the art and include, for example, viruses (e.g., vaccinia virus) as well as bacteria.

The vaccines are administered in a manner compatible with the dosage formulation, and in such amount as will be prophylactically and/or therapeutically effective. The quantity to be administered, which is generally in the range of 5 μg to 250 μg of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each individual.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and/or reenforce the immune response, for example, at 1–4 months for a second dose, and if needed, a subsequent dose(s) after several months. The dosage regimen will also, at lest in part, be determined by the need of the individual and be dependent upon the judgment of the practitioner.

In addition, the vaccine containing the antigen sets comprised of HCV polypeptides described above, may be administered in conjunction with other immunoregulatory agents, for example, immune globulins.

The compositions of the present invention can be administered to individuals to generate polyclonal antibodies (purified or isolated from serum using conventional techniques) which can then be used in a number of applications. For example, the polyclonal antibodies can be used to passively immunize an individual, or as immunochemical reagents.

In another embodiment of the invention, the above-described immunoreactive compositions comprised of a plurality of HCV antigen sets are used to detect anti-HCV antibodies within biological samples, including for example, blood or serum samples. Design of the immunoassays is subject to a great deal of variation, and a variety of these are known in the art. However, the immunoassay will use antigen sets wherein each antigen set consists of a plurality of substantially identical polypeptides comprising the amino acid sequence of an epitope within a first variable domain of an HCV isolate, and the amino acid sequence of one set is heterogeneous with respect to the amino acid sequence of at least one other set. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention containing HCV epitopes from variable domains, in suitable containers, along with the remaining reagents and materials (for example, suitable buffers, salt solutions, etc) required for the conduct of the assay, as well as a suitable set of assay instructions.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLES

In the Examples the following materials and methods were used.

Patient Samples and RNA Extraction

Asymptomatic HCV carriers HCT 18 and HCV J1 and chronically infected HCV patient Th have been previously described in Weiner et al. (1991) Virol. 180:842–848. Patient Q was diagnosed with chronic active hepatitis based on a liver biopsy and was placed on alfa-2b interferon therapy (3 million units, thrice weekly) for six months. RNA from 0.2 ml of plasma was extracted according to the method of Chomcynski and Sacchi, (1987) Anal. Biochem. 162:156–159, using RNAzol™ B reagent (Cinna/Biotecx Laboratories) containing 10 μg/ml MS2 carrier RNA (Boehringer Mannheim, 165–948) as indicated by the manufacturer. RNA was resuspended in 200 μl of diethyl pyrocarbonate treated distilled water and reprecipitated in a final concentration of 0.2M sodium acetate and two and one half volumes of 100% ethanol (−20° C.).

cDNA and Polymerase Chain Reactions

All reactions were performed according to Weiner et al. (1990) Lancet 335:1–5. M13 sequencing was performed according to Messing et al. (1983), Methods in Enzymology 101:20–37. The consensus sequence of at least four cloned inserts are presented with the exception of the HCV J1.2 E2/NS1 sequence which was derived from two clones.

Cloning and sequencing of HCT 18 and Th was as reported in Weiner et al. (1991), supra. Nested PCR primers used to clone the amino terminal and carboxy proximal segments of E2/NS1 in patient Q were:

PCR I

X(E2)14 GGTGCTCACTGGGGAGTCCT(SEQ ID NO:1)(1367–1386)S

X(E2)18J CATTGCAGTTCAGGGCCGTGCTA(SEQ ID NO:2)(1608–1588)A,

PCR II

X(E2)4 TCCATGGTGGGGAACTGGGC(SEQ ID NO:3)(1406–1425)S

X(E2)19J TGCCAACTGCCATTGGTGTT(SEQ ID NO:4)(1582–1562)A;

PCR I

X(E2)14 (above)S

J1rc12 TAACGGGCTGAGCTCGGA(SEQ ID NO:5) (2313–2296)A

PCR II

US(E2)5 CAATTGGTTCGGTTGTACC(SEQ ID NO:6) (1960–1978)S

J1rc13 CGTCCAGTTGCAGGCAGCTTC(SEQ ID NO:7)(2260–2240)A.

PCR primers used to clone the HCV J1 E2/NS1 gene were:
PCR I

J1(E2)14 (above)S

J1(E2)rc30** CAGGGCAGTATCTGCCACTC(SEQ ID NO:8)(2349–2330)A

J1IZ-2* TGAGACGGACGTGCTGCTCCT(SEQ ID NO:9)(1960–1978)S

J1(E2)rc32** TTTGATGTACCAGGCGGCGCA(SEQ ID NO:10)(2658–2636)A

PCR II-E2384.5*
GGATCCGCTAGCCATACCCGCGTGACGGGGGGG GTGCAA(SEQ ID NO:11)(1469–1495)S

DSCON1JBX*
GGATCCTCTAGATTACTCTTCTCACCTATCCCTGT CCTCCAAGTC(SEQ ID NO:12)

ACA(2272–2301)A

J1IZ-1* CAACTGGTTCGGCTGTACA(SEQ ID NO:13) (1915–1935)S

J1(E2)rc31** (2566–2546)A.

*, nt sequence from Takeuchi et al., (1990) Nucl. Acids Res. 18:4626; **, nt sequence from Kato et. al., (1989) Proc. Jpn. Acad. 65B:219–223. Sense (S) or antisense (A) PCR primers are given in the 5' to 3' orientation according nucleotide numbers in reference.

Synthesis of Biotinylated Peptides

The overlapping octapeptides for the hypervariable regions of three strains of HCV were synthesized on clearable-linker, derivatized, polyethylene pins essentially as described by (Maeji et al., (1990) J. Immunol. Methods 134:23–33, was coupled to the N-terminus of each peptide. Finally, biotin was coupled to the N-terminus using 150 μl of a dimethylformamide solution containing 40 mM biotin, 40 mM 1-hydroxybenzotriazole (HOBt), 40 mM benzotriazole-1-yl-oxy-tris-pyrrlidino-phosphonium hexafluorophosphate (PyBOP, NOVABIOCHEM) and 60 mM N-methylmorpholine (NMM) reacting overnight at 20° C.

After biotinylation, the peptides were side-chain deprotected, washed and the peptide from each pin was cleaved in 200 μl of 0.1M phosphate buffer (pH 7.2). Microtitre plates containing the cleaved peptide solutions were stored at −20° C. until needed.

ELISA Testing of Biotinylated Peptides

Polystyrene plates (Nunc immuno plate maxisorb F96) were coated with streptavidin by incubating overnight at 4° C. with 0.1 ml/well of a 5 μg/ml solution of streptavidin (Sigma Cat. No. S4762) in 0.1M carbonate buffer at pH 9.6. After removal of the streptavidin solution, the wells were washed four times with a 0.1% solution of Tween 20 in PBS. Nonspecific binding was blocked by incubating each well with 0.2 ml of 2% BSA in PBS for 1 h at 20° C. The wells were again washed four times with PBS/Tween 20. Plates were air-dried and stored at 4° C. until required. The streptavidin in each well was coupled to cleaved peptides by incubation with 100 μl of a 1:100 dilution of cleaved peptide solution with 0.1% BSA in PBS containing 0.1% sodium azide for 1 h at 20° C. After incubation, the plate was washed four times with PBS/Tween 20. Each well was incubated with 100 μl of a suitable dilution of serum (diluted with 2% BSA in PBS containing 0.1% sodium azide) for 1 h at 20° C. or overnight at 4° C. followed by four washes with PBS/Tween 20. Bound antibody was detected by reaction for 1 h at 20° C. in 0.1 ml conjugate. This consisted of 0.25 ml/l (a saturating level) of horseradish peroxidase-labeled goat anti-rabbit IgG (H+L) (Kirkegaard and Perry Labs, Gaithersburg, Md.) in CASS (0.1% sheep serum, 0.1% Tween 20, 0.1% sodium caseinate diluted in 0.1M PBS, pH 7.2). The wells were washed 2 times with PBS/Tween 20 followed by two washes with PBS only. The presence of enzyme was detected by reaction for 45 min at 20° C. with 0.1 ml of a freshly-prepared solution containing 50 mg of ammonium 2,2'-azino-bis[3-ethylbenzothiazoline-6-sulphonate (ABTS, Boehringer Mannheim Cat. no. 122661) and 0.03 ml of 35% (w/w) hydrogen peroxide solution in 100 ml of 0.1M phosphate/0.08M citrate buffer, pH 4.0. Color development was measured in a Titertek Multiscan MC plate reader in the dual wavelength mode at 405 nm against a reference wavelength of 492 nm.

Computer Generated Antigenicity Profile

Antigenicity profiles for the HCV E2/NS1 protein and HIV-1 gp120 hypervariable region V3 (aa 303–338) were derived from a computer program based on the degree of sequence variability as originally proposed by Kabat [Sequences of proteins of immunological interest. U.S. Department of Health and Human Services, Public Health Service, National Institutes of Health (1983)] for the identification of the hypervariable loops of immunoglobulins multiplied by the average of the individual probability that antibody binding is retained for each possible pair-wise amino acid. Probabilities for retention of antibody binding associated with a given amino acid change were the values experimentally determined by assessing the effects on antibody binding of all possible amino acid substitutions for 103 characterized linear epitopes. Geysen et al., (1988) J. Mol. Rec. 1:32–41. This algorithm thus weights the variability index to give more significance to amino acid changes likely to have a significant effect on antibody binding, i.e., compensates for conservative amino acid changes. Fifteen HCV sequences [HCV-1, Q3.2, HCT 23, EC10, HC-J1, HCVE1, TH, HCT 27, Q1.2, HCT18, HC-J4, HCV J1.2/HCV J1.1, HCV J, HCV BK], were used to determine the antigenicity profile for HCV. The HIV-1 V3 profile was obtained by averaging 242 individual profiles of 15 sequences selected at random from the numerically greater data base of unique HIV-1 sequences. LaRosa et al., (1990) Science 249:932–935 & correction in science (1991) p. 811. The amino acid sequences of some of these isolates between aa 384 and 420 are shown in FIG. 3.

Computer Generated Secondary Structure Predictions

The α-helix, β-sheet and β-turn secondary structure probabilities for the amino-terminal region (384–420) were determined using an algorithm, which assigns the probabilities for each of the three above secondary structural motifs to each residue. The coefficients used in the algorithm were obtained for all pair-wise combinations of residues of the structural data base. Levitt and Greer, (1977) J. Mol. Biol. 114:181–293. The prediction parameters obtained from these coefficients were fitted to the observed outcome when the algorithm was applied back on the database to obtain probabilities that a given residue would be found in one of the three defined secondary structural motifs.

Example 1

Figure 4A:
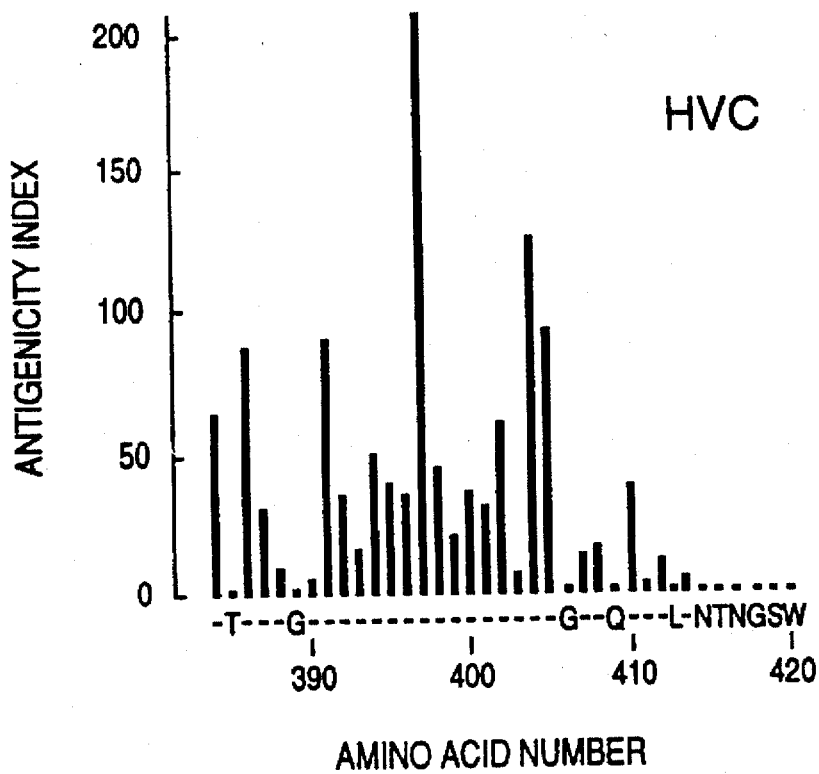
FIG. 4 are graphs showing the antigenicity profiles for the amino-terminal region of the putative HCV E2/NS1 protein (amino acids 384–420), and the gp 120 V3 hypervariable-region of HIV-1.
Figure 4B:
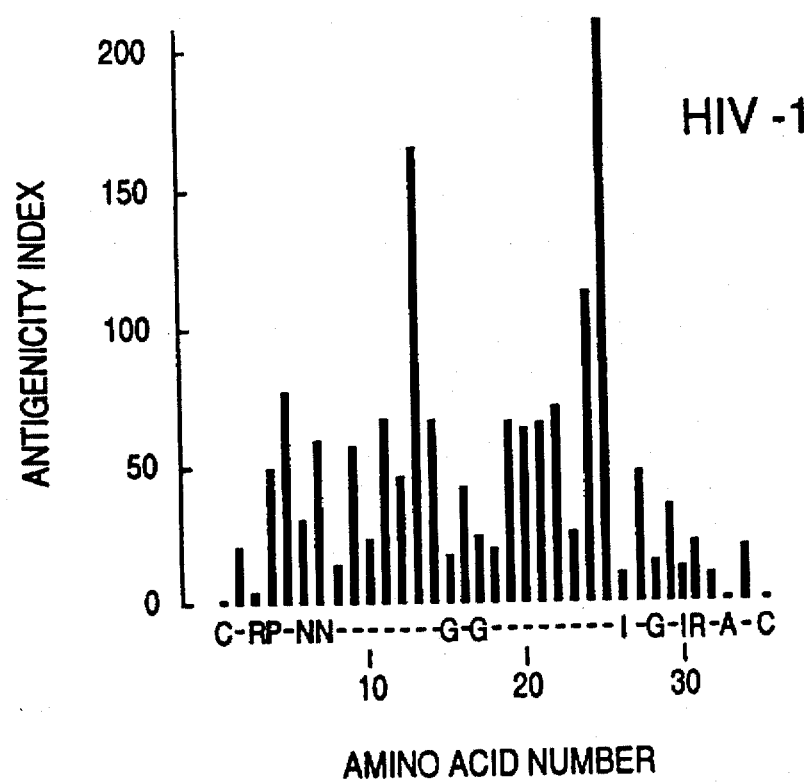
Figure 5A:
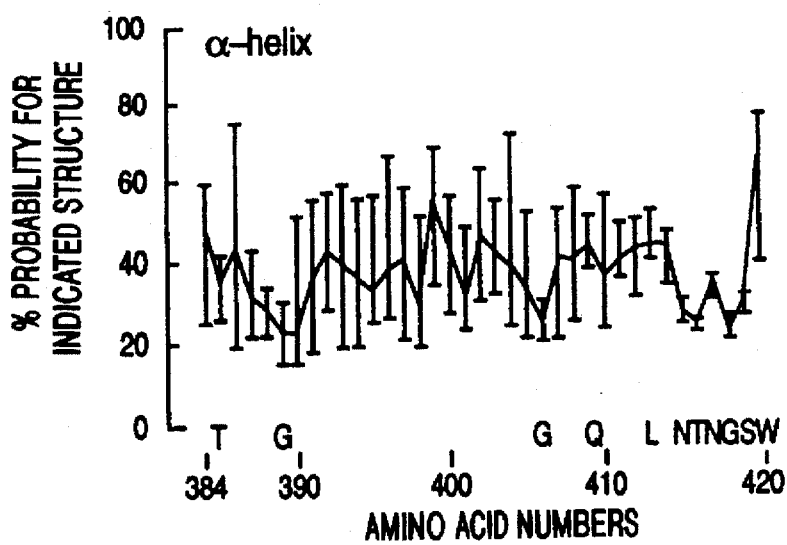
FIG. 5 shows a series of graphs which give the percentage probabilities that a given residue from the amino-terminal region of HCV E2/NS1 protein (amino acids 384 to 420) will be found in either alpha-helix, beta-sheet or beta-turn secondary structural motif.
Figure 5B:
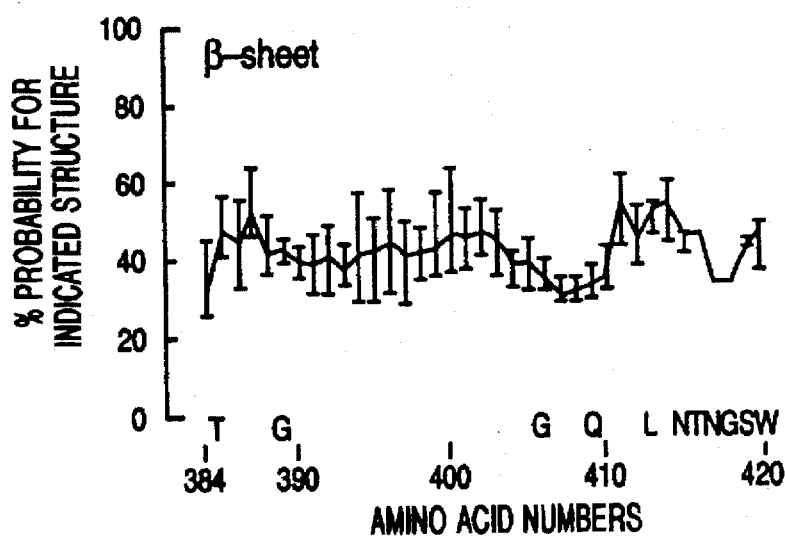
Figure 5C:
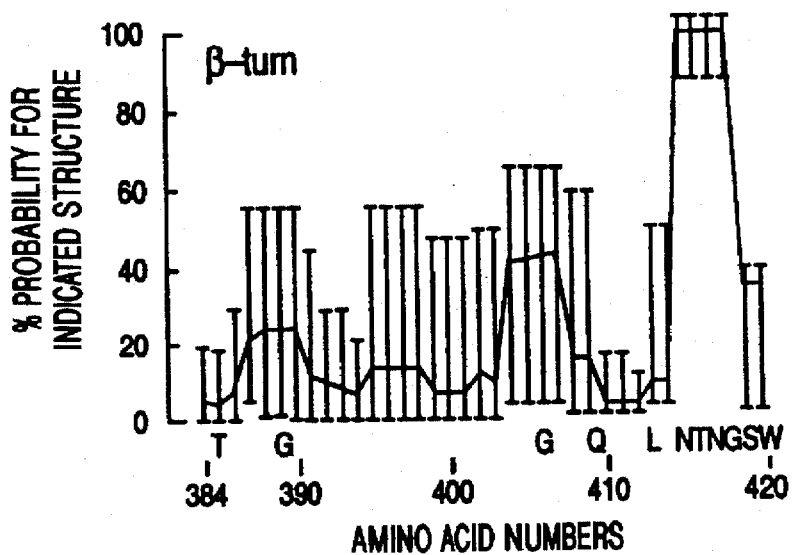

Comparison of Secondary Structure and Amino Acid Sequence Variation in the HCV E2/NS1 HV and HIV-1 gp120 Domains The amino acid sequences from fifteen HCV and HIV-1 isolates were compared with respect to the number of positions at which amino acid sequence heterogeneities were observed in the HCV E2 HV or HIV-1 gp120 V3 domains (FIGS. 4, A and B, respectively). Amino acid heterogeneities occurred in 25 of 30 amino acid positions in the E2 HV region and 23 of 35 amino acid positions in the HIV-1 gp120 V3 domain. Dashes on the x-axis of FIGS. 4 A and B represent amino acid positions where variable amino acid residues occur and invariant amino acids are given in the single letter amino acid code. The antigenicity profiles shown in FIG. 4 indicate that, similar to the V3 loop of the HIV-1 gp120 protein (FIG. 4B), a block of amino acid residues in the HCV E2 (amino acids 384–414 in FIG. 4A) was identified whose variation had a predicted adverse affect on antibody binding. The data in FIG. 4 indicate that the HCV E2 domain resembles the HIV-1 gp120 V3 domain, which is known to encode virus neutralizing epitopes, in both the degree and predicted significance of observed amino acid variation and suggests that the E2 HV domain may have a similar function as the gp120 V3 domain.

Linear epitopes are more likely associated with less structured regions of proteins, in particular, the ends of proteins or with extended surface loops. A computer analysis was used to predict the probability that an individual residue is associated with a defined secondary structural motif for 15 E2 HV amino acid sequences between residues 384 to 420. FIG. 4 shows that the region between the E2 amino-terminal residue 384 and the strongly predicted, highly conserved beta-turn (residues 415–418) is relatively unstructured as indicated by less than 50 percent probability of alpha-helix, beta-sheet or beta-turn character. Lack of strongly predictive structure in the E2 HV domain is consistent with the tolerance for extensive sequence variation found between isolates and is in contrast with highly structured regions which contribute to tertiary folding of the protein. The HCV E2 EV domain appears to be even less structured than the V3, principal neutralizing domain of HIV-1 gp120, which has been reported to contain a beta strand-type II beta turn-beta strand-alpha helix motif and may have greater structural constraints on amino acid variability than the HCV E2 HV domain. Taken together, the evidence suggests that the E2 HV domain appears to have features characteristic of protein domains which contain likely sites of linear neutralizing epitopes.

Example 2

Epitope Mapping of the HCV E2/NS1 HV Domain

Figure 6A:
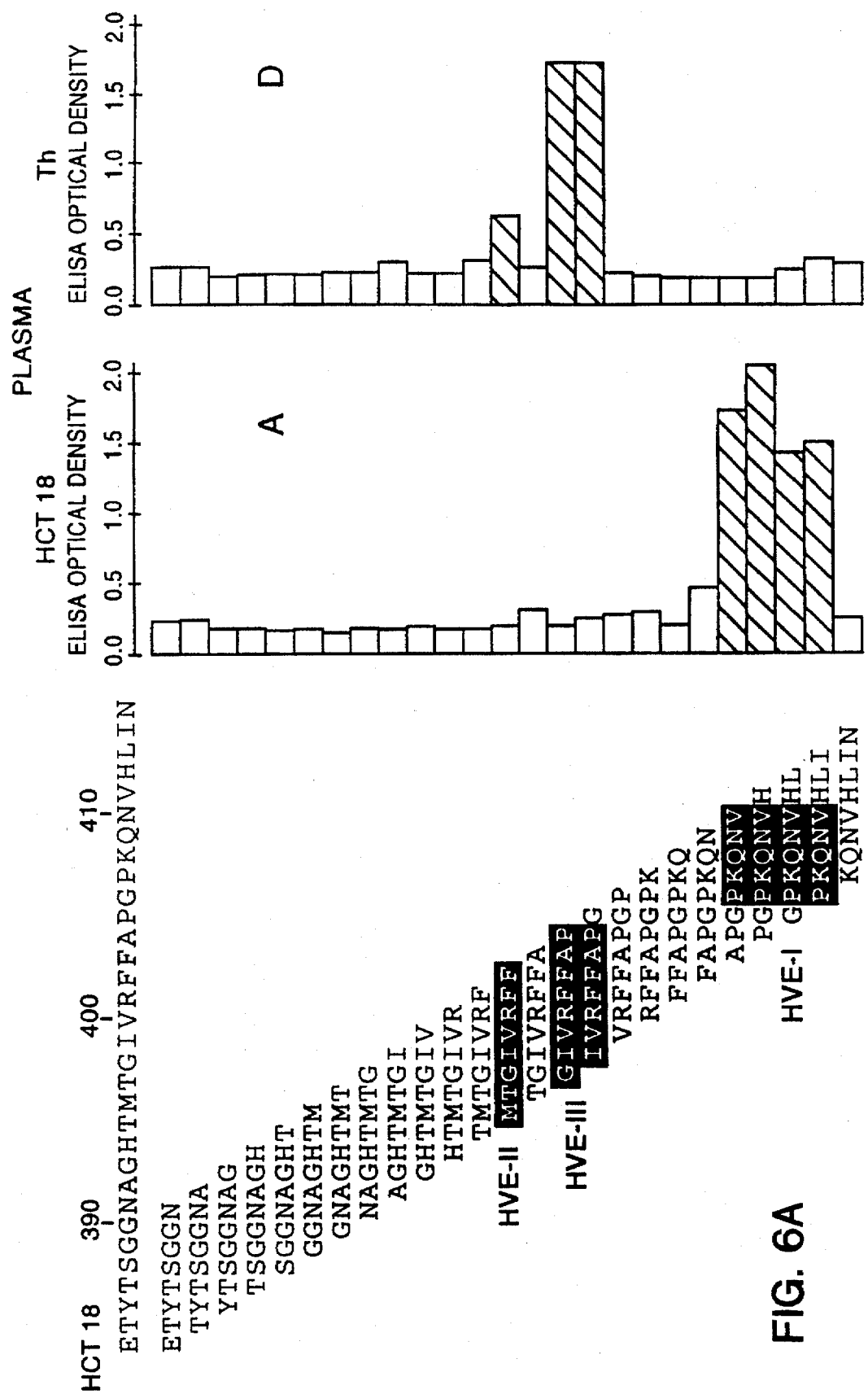
FIG. 6 are bar graphs showing the reactivity of antibodies in the plasma from HCV 18 (panels A–C) or Th (Panels D–f) with overlapping biotinylated 8mer peptides derived from amino acids 384 to 415 or 416 of HCV isolates HCT 18 (A,D), Th (B,E) and HCV J1 (C,F), respectively. (SEQ ID NOS:33–35)
Figure 6B:
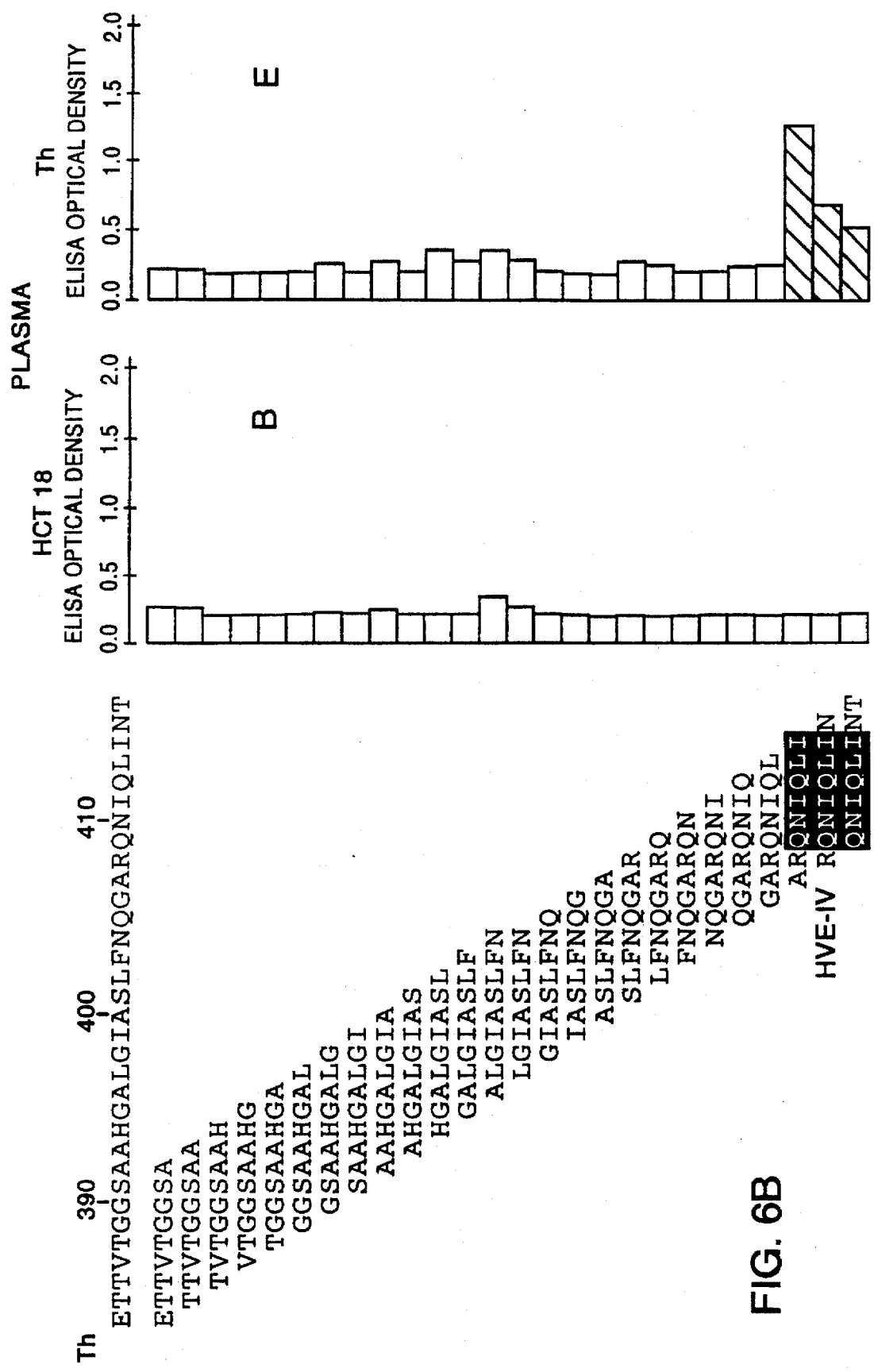
Figure 6C:
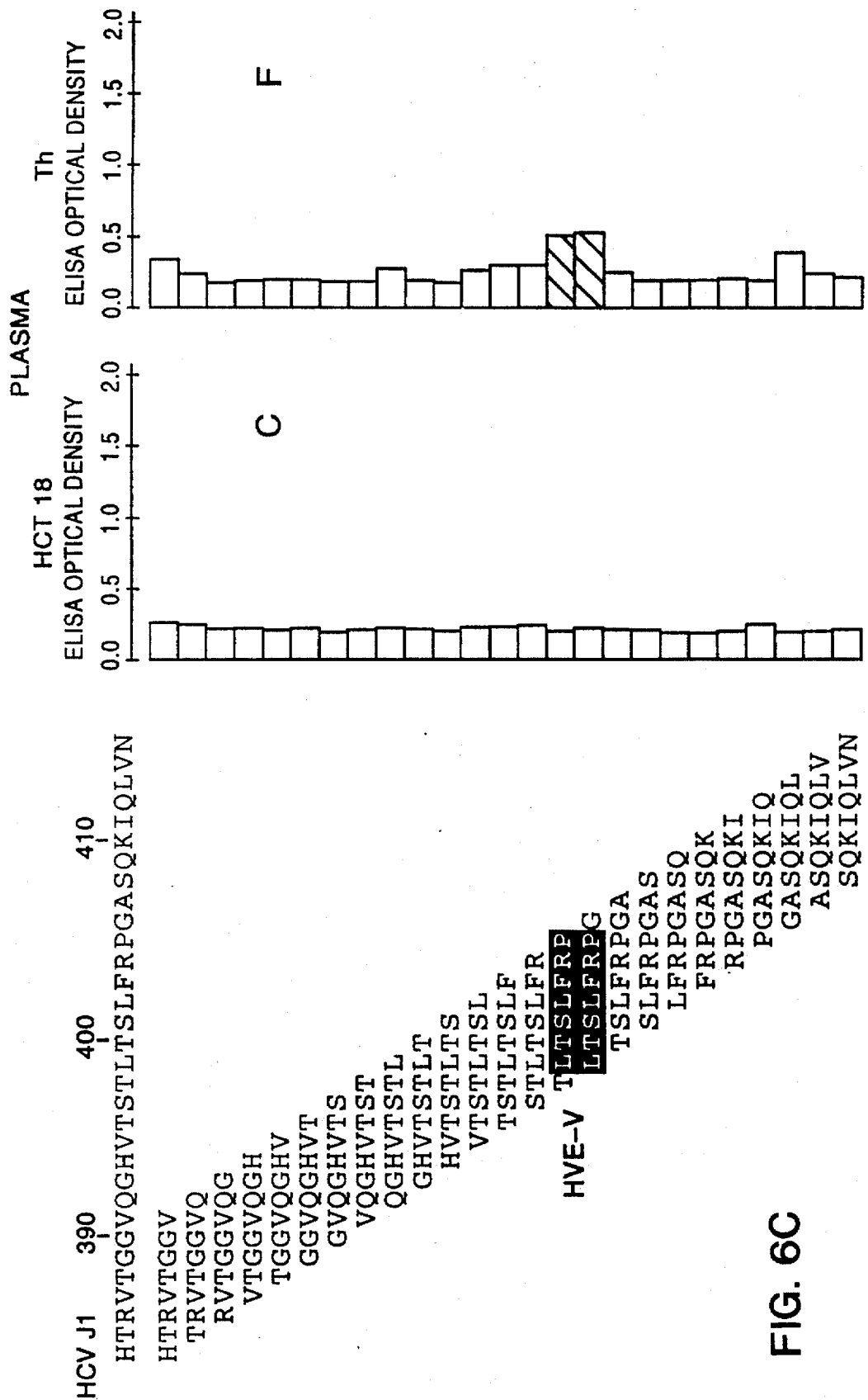

Overlapping biotinylated 8-mer peptides corresponding to and extending past the E2/NS1 HV domain (amino acids 384 to 416) of HCT 18 (A,D), Th (B,E) and HCV J1 (C,F) were bound to plates coated with streptavidin and reacted with plasma from either HCT 18 (A–C) or Th (D–F). The results are shown in FIG. 6 for HCV isolates HCT 18 (FIGS. 6A and 6D), Th (FIGS. 6B and 6E), and HCV J1 (FIGS. 6C and 6F). HCT 18 plasma was diluted 1:200 and Th plasma was diluted 1:500. HVE-1, -2, -3, -4 and -5, represent isolate specific epitopes.

As seen from FIG. 6, HCT 18 plasma identified a linear epitope ($^{407}$PKQNV$^{411}$) when tested with peptides derived from the HCT18 sequence (HVE-I in FIG. 6A), but failed to react with peptides corresponding to the HV domain of two different strains Th and HCV J1 (FIGS. 6B and 6C). In contrast, Th plasma identified linear epitope HVE-IV in the HV domain of Th ($^{409}$QNIQLI$^{414}$, FIG. 6E), and also epitopes in strain HCT 18 ($^{399}$IVRFFAP$^{405}$, FIG. 6D) and HCV J1. Th, an IV drug user, may have been exposed to multiple strains of HCV.

Both Th and HCT 18 plasma each reacted with an epitope (amino acids 413–419) common to all three isolates (data not shown) when used in an ELISA with pin synthesized overlapping 8mer peptides from each isolate.

In order to validate antibody binding specificity, antibodies bound to biotinylated peptides containing amino acids 403–407 were eluated and used to block the reactivity of HCT 18 plasma with pins containing overlapping 8-mers for the HCT 18 HV domain. These data indicate that 1) the E2/NS1 HV domain is immunogenic, 2) there are multiple epitopes which map to this region, and 3) a subset of epitopes (EVE-1, -2, -3, -4 or -5 in FIG. 6) in the HV domain are isolate specific.

Example 3

Determination that Variant E2/NS1 HV Domains can be Associated with Flares of Hepatitis To investigate the possibility of finding HCV variants associated with the intermittent flares of hepatitis often found in chronic HCV infections, we partially sequenced the E2/NS1 gene from a patient, Q, with chronic hepatitis during two distinct episodes of hepatitis approximately two years apart (Q1 and Q3, respectively). The second episode of hepatitis occurred 1.5 years after the termination of interferon treatment.

Figure 7:
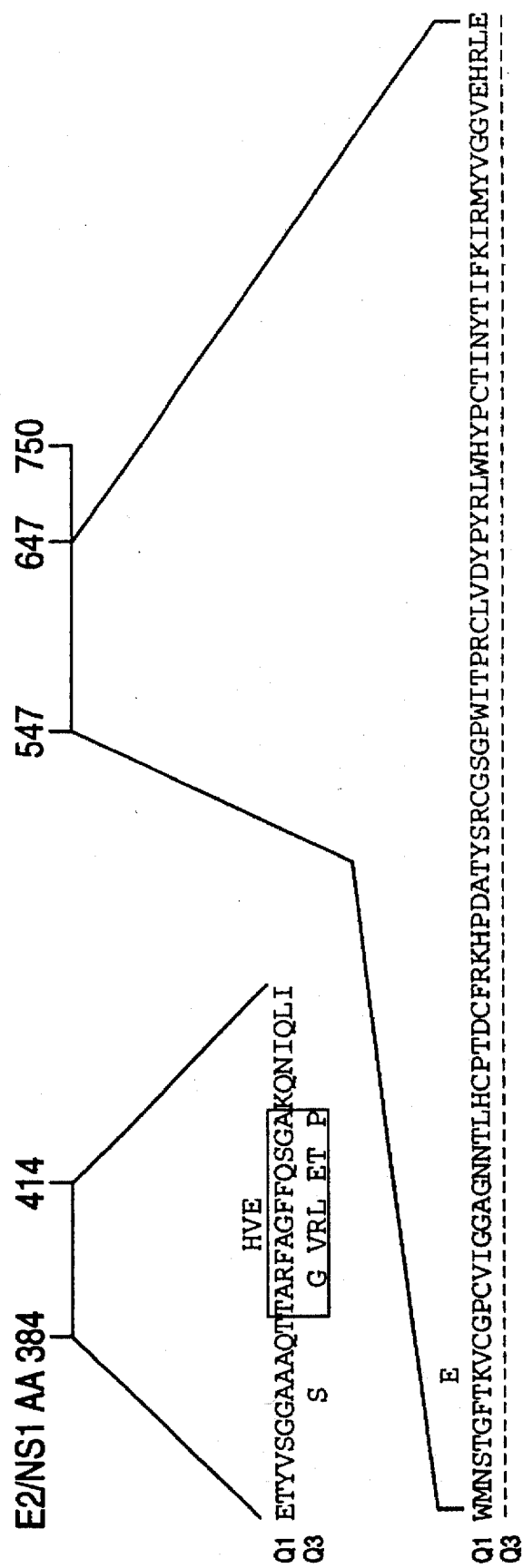
FIG. 7 shows the deduced amino acid sequences of two regions of the E2/NS1 polypeptide, amino acids 384–414 and 547–647, given for the Q1 and Q3 isolates. (SEQ ID NOS:25–28)

The differences in the deduced amino acid sequence of the Q1 and Q3 E2/NS1 HV region was strikingly different only between amino acids 391–408 with seven of eight changes occurring between amino acid 398 and 407 (FIG. 7). FIG. 7 shows the deduced amino acid sequences of two regions of the E2/NS1 polypeptide, amino acids 384–414 and 547–647, for the Q1 and Q3 isolates. The amino acid (E) above the Q1 sequence was found in one of four Q1 clones. The boxed amino acids represent the location of the Q1 or Q3 HVE 12mer peptide. Amino acid sequence differences found between Q1 and Q3 are printed in bold type.

Only one amino acid heterogeneity was observed between amino acids 547 and 647 of the Q1 and Q3 E2/NS1 polypeptides (FIG. 7).

To examine the effect of the amino acid substitutions observed in the Q1 and Q3 E2 HV domains on antibody binding, we synthesized a Q1 and Q3 specific 12-mer peptide from amino acids 396 to 407 (HVE Q1 or Q3 in FIG. 7B) and separately reacted the Q1 and Q3 plasma with each peptide in an ELISA. Table 4 shows that antibodies in both the Q1 and Q3 plasma reacted with the Q1 peptide but not with the Q3 peptide. Statistical analysis (Student's Test) indicated that the binding of the Q1/Q3 plasma to the Q1 peptide was significantly above background binding of those plasma to a panel of 12 randomly chosen control peptides (P<0.001), while binding of either the Q1 or Q3 plasma to the Q3 peptide was not statistically significant. The data indicate that although patient Q developed antibodies to the HCV Q1 HV domain, which were still detectable two years later at the Q3 time point, no detectable humoral response had developed to the Q3 E2 HV variant which was predominant during the second episode of hepatitis.

TABLE 4

| Elisa Results on 12-mer Peptides | | | | |
|---|---|---|---|---|
| | TARFAG-FFQSGA Q1 seq | | TAGFVR-LFETGP Q3 seq | |
| Plasma | Mean | sd | Mean | sd |
| Q1 | 1.158 | 0.134 | 0.691 | 0.123 |
| Q3 | 1.022 | 0.123 | 0.693 | 0.036 |

Example 4

Detection of Coexisting E2/NS1 Genes with Distinct E2/NS1 HV Domains in HCV Infected Individuals FIG. 8A shows the amino acid sequences deduced from two isolates of HCV J1 (J1.1 & J1.2) which were cloned from one plasma sample of the Japanese volunteer blood donor HCV J1. Kubo et al., (1989) Nucl. Acids Res. 17:10367–10372. Of the 23 total amino acid changes between HCV J1.1 and HCV J1.2, 9 differences indicated by bold type are clustered in the 30 amino acid E2/NS1 HV domain. Five of the 9 amino acid substitutions in the E2/NS1 HV domain represent nonconservative amino acid changes. Since HCV J1 is the only group II HCV genome which has been cloned in our laboratory, it is unlikely that these differences are due to cross contamination of the HCV J1 plasma. The HCV J1.2 sequence represents a minority sequence in HCV J1's blood since only two E2/NS1 HV variant sequences were identified from 7 cloned sequences which originated from two independent PCR reactions.

Interestingly, a comparison of the HCT27 and HCV E1 isolates (FIG. 8B), which were sequenced in different laboratories and derive from presumably unrelated individuals, showed that the number of amino acid differences in the E2/NS1 HV domain of these isolates were fewer than the number of differences observed between isolates from the same individual.

The above described results lead to the suggestion that the HCV genome is rapidly evolving in individuals and the population.

Industrial Utility

The immunoreactive compositions of the invention, have utility in the preparation of materials, for example, vaccines, which in turn may be used for the treatment of individuals against HCV infections, particularly chronic HCV infections. In addition, the compositions may be used to prepare materials for the detection of multiple variants of HCV in biological samples. For example, the immunoreactive compositions of the present invention can be used to generate polyclonal antibody compositions that recognize more than one HCV isolate, or as the antigen in an anti-HCV antibody immunoassay. The latter method can be used to screen blood products for possible HCV contamination. Polyclonal antiserum or antibodies can be used to for passive immunization of an individual.

What is claimed is:

1. An immunogenic polypeptide composition comprising at least two HCV amino acid sequences, each HCV sequence comprising at least one epitope within a variable domain of an HCV envelope protein, wherein the variable domain regions of the amino acid sequences are heterogeneous with each other, are derived from distinct HCV isolates, and each sequence being not longer than the full length envelope protein.

2. An immunogenic composition according to claim 1 comprising a plurality of antigen sets, wherein (a) each antigen set consists of a plurality of substantially identical sequences comprising at least one epitope within a variable domain of an HCV-envelope-polypeptide, and (b) the amino acid sequence of the epitope of one set is heterogeneous with respect to the amino acid sequence of at least one other set.

3. An immunogenic composition according to claim 1 wherein the distinct HCV isolates include an HCV group I isolate and an HCV group II isolate.

4. An immunogenic composition according to claim 1 wherein the variable domain is within the E2/NS1 protein.

5. An immunogenic composition according to claim 4 wherein the variable domain is encoded from about amino acid 384 to about amino acid 414 of the HCV polyprotein.

6. An immunogenic composition according to claim 1 wherein the variable domain is within the E1 protein.

7. An immunogenic composition according to claim 6 wherein the variable domain is encoded from about amino acid 215 to about acid 255 of the HCV polyprotein.

8. An immunogenic composition according to claim 1 wherein each amino acid sequence further comprises an epitope within a second variable domain of an HCV-envelope-polypeptide, wherein the second variable domain regions of the amino acid sequences are heterogenous with each other and are derived from distinct HCV isolates.

9. An immunogenic composition according to claim 8 wherein the first variable domain is within the E2/NS1 protein and the second variable domain is within the E1 protein.

* * * * *